(12) United States Patent
Hakamata et al.

(10) Patent No.: US 6,780,608 B1
(45) Date of Patent: Aug. 24, 2004

(54) HUMAN TYPE 3 RYANODINE RECEPTOR PROTEIN AND DNA MOLECULES CODING THEREFOR

(75) Inventors: Yasuhiro Hakamata, Shizuoka (JP); Seiichiro Nishimura, Minoo (JP); Edward Leon Barsoumian, Toyonaka (JP)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 09/424,783

(22) PCT Filed: May 18, 1998

(86) PCT No.: PCT/EP98/02926

§ 371 (c)(1),
(2), (4) Date: Dec. 1, 1999

(87) PCT Pub. No.: WO98/54212

PCT Pub. Date: Dec. 3, 1998

(30) Foreign Application Priority Data

May 28, 1997 (DE) .......................... 197 22 317

(51) Int. Cl.$^7$ ........................... C12P 21/06; C12N 1/20; C12N 15/74; C07K 1/00; C07H 21/04
(52) U.S. Cl. ................ 435/69.1; 435/252.3; 435/320.1; 435/325; 435/471; 435/7.1; 435/7.2; 530/350; 530/402; 536/23.5
(58) Field of Search ................................ 530/350, 402; 435/69.1, 70.1, 71.1, 71.2, 252.3, 320.1, 325, 471, 7.1, 7.2; 536/23.5

(56) References Cited

FOREIGN PATENT DOCUMENTS

WO    WO 91/04328 A1    4/1991

OTHER PUBLICATIONS

Nakashima Y, et al. FEBS Letters 417:157–162, 1997.*
Blumenthal, D.K., et al., "Identification of the calmodulin–binding domain of skeletal muscle myosin light chain kinase," *Proc. Natl. Acad. Sci. USA 82*:3187–3191 (1985).
García, J., and Beam, K.G., "Measurement of Calcium Transients and Slow Calcium current in Myotubes," *J. Gen. Physiol. 103*:107–123 (1994).
Gillard, E.F., et al., "A Substitution of Cysteine for Arginine 614 in the Ryanodine Receptor Is Potentially Causative of Human Malignant Hyperthermia," *Genomics 11*:751–755 (1991).
Goeddel, D.V., et al., "The structure of eight distinct cloned human leukocyte interferon cDNAs," *Nature 290*:20–26 (1981).
Hakamata, Y., et al., "Primary structure and distribution of a novel ryanodine receptor/calcium release channel from rabbit brain," *FEBS Lett. 312*: 229–235 (1992).

Hakamata, Y., et al., "Involvement of the brain type of ryanodine receptor in T–cell proliferation," *FEBS Lett. 352*: 206–210 (1994).
Kemp, B.E., and Pearson R.B., "Protein kinase recognition sequence motifs," *Trends Biochem. Sci. 15*:342–346 (1990).
Kozack M., "Compilation and analysis of sequences upstream from the translational start site in eukaryotic mRNAs," *Nucl. Acids Res. 12*:857–872 (1984).
MacLennan, D.H., and Phillips, M.S., "Malignant Hyperthermia," *Science 256*:789–794 (1992).
Maeda, A., et al., "Generation of Cell Transfectants Expressing Cardiac Calcium Ion Channel and Calcium Indicator Protein Aequorin," *Anal. Biochem. 242*: 31–39 (Nov. 1996).
McPherson, P.S., and Campbell, K.P., "Solubilization and Biochemical Characterization of the High Affininty ($^3$H)Ryanodine Receptor from Rabbit Brain Membranes," *J. Biol. Chem. 265*: 18454–18460 (1990).
Moncrief, N.D., et al., "Evolution of EF–Hand Calcium–Modulated Proteins," *J. Mol. Evol. 30*:522–562 (1990).
Nakai, J., et al., "Primary structure and functional expression from cDNA of the cardiac ryanodine receptor/calcium release channel," *FEBS Lett. 271*:169–177 (1990).
Nakai, J., et al., "Enhanced dihydropyridine receptor channel activity in the presence of ryanodine receptor," *Nature 380*:72–75 (Mar. 1996).
Niidome, T., et al., "Molecular cloning and characterization of a novel calcium channel from rabbit brain," *FEBS Lett. 308*:7–13 (1992).
Penner, R., et al., "Functional expression of the calcium release channel from skeletal muscle ryanodine receptor cDNA," *FEBS Lett. 259*:217–221 (1989).
Takeshima, H., et al., "Primary structure and expression from complementary DNA of skeletal muscle ryanodine receptor," *Nature 339*:439–445 (1989).
Weirenga, R.K., and Hol, W.G.J., "Predicted nucleotide––binding properties of p21 protein and its cancer–associated varient," *Nature 302*:842–844 (1983).
Zorzato, F., et al., "Molecular Cloning of cDNA Encoding Human and Rabbit Forms of the Ca$^{2+}$Release Channel (Ryanodine Receptor) of Skeletal Muscle Sarcoplasmic Reticulum," *J. Biol. Chem. 265*:2244–2256 (1990).

* cited by examiner

Primary Examiner—Robert Landsman
(74) *Attorney, Agent, or Firm*—Sterne, Kessler, Goldstein & Fox P.L.L.C.

(57) ABSTRACT

The invention relates to nucleic acids and protein of the human ryanodine receptor of type 3 (hRyR3), chimeric ryanodine receptors containing sections of the human receptor and processes for preparing these proteins. The invention further relates to the detection of ryanodine receptors in human tissues for diagnosing pathological conditions and methods of identifying activators or inhibitors of hRyR3.

17 Claims, 60 Drawing Sheets

FIGURE 1A

| | | | | | | |
|---|---|---|---|---|---|---|
| hBRR | MAEGGEGG | EDEIQFLRTE | DEVVLQCI | ATIHKEQRKF | CLAA | 1-40 |
| rBRR | MAEGGEGG | EDEIQFLRTE | DEVVLQCI | ATVHKEQRKF | CLAA | 1-40 |
| rSRR | MGDGGEG- | EDEVQFLRTD | DEVVLQCSA | TVLKEQLKL | CLAA | 1-39 |
| rCRR | MADGGEG- | EDEIQFLRTD | DEVVLQCT | ATIHKEQQKL | CLAA | 1-39 |

| | | | | | | |
|---|---|---|---|---|---|---|
| hBRR | EGLGNRLCF | LEPTSEAKYI | PPDLCVCN | FVLEQSLSVRALQ | | 41-80 |
| rBRR | EGLGNRLCF | LEPTSEAKFI | PPDLCVCN | FVLEQSLSVRALQ | | 41-80 |
| rSRR | EGFGNRLCF | LEPTSNAQNV | PPDLAICCE | TLEQSLSVRALQ | | 40-79 |
| rCRR | EGFGNRLCF | LESTSNSKNV | PPDLSICTF | VLEQSLSVRALQ | | 40-79 |

| | | | | | | |
|---|---|---|---|---|---|---|
| hBRR | EMLANTGENGGEG | --- | --- | AAQGGGHRTLLYGHA | | 81-108 |
| rBRR | EMLANTGENGGEG | --- | --- | AAQGGGHRTLLYGHA | | 81-108 |
| rSRR | EMLANTVEAGVE- | --- | --- | SSQGGGHRTLLYGHA | | 80-106 |
| rCRR | EMLANTVEKS-- | EGQVDVEKWKFMMKTA | QGGGHRTLLYGHA | | | 80-118 |

FIGURE 1B

| | | | | |
|---|---|---|---|---|
| hBRR | VLLRHSFSGMYLTCLTTSRSQTDKLAFDVGLREHATGEAC | 109-148 |
| rBRR | ILLRHSFSGMYLTCLTTSRSQTDKLAFDVGLREHATGEAC | 109-148 |
| rSRR | ILLRHAHSRMYLSCLTTSRSMTDKLAFDVGLQEDATGEAC | 107-146 |
| rCRR | ILLRHSYSGMYLCCLSTSRSSTDKLAFDVGLQEDTTGEAC | 119-158 |
| hBRR | WWTIHPASKQRSEGEKVRIGDDLILVSVSSERYLHLSVSN | 149-188 |
| rBRR | WWTIHPASKQRSEGEKVRIGDDLILVSVSSERYLHLSISN | 149-188 |
| rSRR | WWTMHPASKQRSEGEKVRVGDDLILVSVSSERYLHLSTAS | 147-186 |
| rCRR | WWTIHPASKQRSEGEKVRVGDDLILVSVSSERYLHLSYGN | 159-198 |
| hBRR | GNIQVDASFMQTLWNVHPTCSGSSIEEGYLLGGHVVRLFH | 189-228 |
| rBRR | GNIQVDASFMQTLWNVHPTCSGSSIEEGYLLGGHVVRLFH | 189-228 |
| rSRR | GELQVDASFMQTLWNMNPICSCC--EEGYVTGGHVLRLFH | 187-224 |
| rCRR | GSLHVDAAEQQTLWSVAPISSGSEAAQGYLIGGDVLRLLH | 199-238 |

FIGURE 1C

| | | | | |
|---|---|---|---|---|
| hBRR | GH-DECLTIPSTDQNDSQHR | RIFYEAGGAGTR | ARSLWRVE | 229-267 |
| rBRR | GH-DECLTIPSTDQNDSQHR | RIFYEAGGAGTR | ARSLWRVE | 229-267 |
| rSRR | GHMDECLTISAAD-SDDQRR | LVYYEGGAVCT | HARSLWRLE | 225-263 |
| rCRR | GHMDECLIVPSGEHGEEQRR | TVHYEGGAVSV | HARSLWRLE | 239-278 |
| | | | | |
| hBRR | PLRISWSGSNIRWGQA | FRLRHLTTGHYLALTEDQGLILQD | | 268-307 |
| rBRR | PLRISWSGSNIRWGQA | FRLRHLTTGHYLALTEDQGLLLQD | | 267-307 |
| rSRR | PLRISWSGSHLRWGQP | LRIRHVTTGRYLALTEDQGLVVVD | | 264-303 |
| rCRR | TLRVAWSGSHIRWGQP | FRLRHVTTGKYLSLMEDKNLLLMD | | 279-318 |
| | | | | |
| hBRR | RAKSDTKSTAFSFRASKELKEKLDSSHKRDIEGMGVPEIK | | | 308-347 |
| rBRR | RGKADTKSTAFSFRPSKETKEKLDSSHKRDIEGMGVPEIK | | | 308-347 |
| rSRR | ACKAHTKATSFCFRVSKE---KLDTAPKRDVEGMGPPEIK | | | 304-340 |
| rCRR | KEKADVKSTAFTFRSSKE---KLDGGVRKEVDGMGTSEIK | | | 319-355 |

FIGURE 1D

| | | | |
|---|---|---|---|
| hBRR | YGDSVCFVQHIASGLWVTYKAQDAKTSRLGPLKRKVILHQ | 348-387 |
| rBRR | YGDSVCFVQHIASGLWVTYKAQDAKTSRLGPLKRKVILHQ | 348-387 |
| rSRR | YGESLCFVQHVASGLWLTYAAPDPKALRLGVLKKAILHQ | 341-380 |
| rCRR | YGDSICYIQHVDTIGLWLTYQSVDVKSVRMGSIQRKAIMHH | 356-395 |

| | | | |
|---|---|---|---|
| hBRR | EGHMDDGLTLQRCQREESQAARIIRNTTALFSQFVSG---- | 388-424 |
| rBRR | EGHMDDGLTLQRCQREESQAARIIRNTTALFSQFVSG---- | 388-424 |
| rSRR | EGHMDDALFLTRCQQEESQAARMIHSTAGLYNQFIKGLDS | 381-420 |
| rCRR | EGHMDDGLNLSRSQHEESRTARVIRSTVFLENREIRGLDA | 396-435 |

| | | | |
|---|---|---|---|
| hBRR | --NNRTAAPI----TLPIEEVLQTLQDLIAYFQPPEEEMR | 425-458 |
| rBRR | --NNRTAAPV----TLPIEEVLQTLHDLIAYFQPPEEEMQ | 425-458 |
| rSRR | FSGKPRGSGPPAGPALPIEAVILSLQDLIGYFEPPSEELQ | 421-460 |
| rCRR | LSKKAKASSV----DLPIESVSLISLQDLIGYFHPPDEHLE | 436-471 |

FIGURE 1E

```
hBRR  HEDKQNKLRS LKNRQNLFKE EGMLALVLNC IDRLNVYNSV  459-498
rBRR  HEDKQNKLRS LKNRQNLFKE EGMLALVLNC IDRLNIYNSV  459-498
rSRR  HEEKQSKLRS LRNRQSLFQE EGMLSLVLNC IDRLNVYTTA  461-500
rCRR  HEDKQNRLRA LKNRQNLFQE EGMINLVLEC IDRLHVYSSA  472-511 hBRR  AHFAGIAREE SGMAWKEILN LLYKLLAALI RGNRNNCAQF  499-538
rBRR  AHFAGIAREE SGMAWKEVLS LLYKLLAALI RGNRNTCAQF  499-538
rSRR  AHFAEYAGEE AAESWKEIVN LLYELLASLI RGNRANCALF  501-540
rCRR  AHFADVAGRE AGESWKSILN SLYELLAALI RGNRKNCAQF  512-551 hBRR  SNNLDWLISK LDRLESSSGI LEVLHCILTE SPEALNLIAE  539-578
rBRR  SNNLDWLISK LDRLESSSGI LEVLHCILIE SPEALNLIAE  539-578
rSRR  STNLDWVVSK LDRLEASSGI LEVLYCVLIE SPEVLNIIQE  541-580
rCRR  SGSLDWLISR LERLEASSGI LEVLHCVLVE SPEALNIIKE  552-591
```

FIGURE 1F

| | | | |
|---|---|---|---|
| hBRR | GHIKSIISLLDKHGRNHKVLD|ILCSLCL|CNGVAVRANQNL | 579-618 |
| rBRR | GHIKSIISLLDKHGRNHKVLDVLCSLCLCNGVAVRANQNL | 579-618 |
| rSRR | NHIKSIISLLDKHGRNHKVLDVLCSLCVCNGVAVRSNQDL | 581-620 |
| rCRR | GHIKSIISLLDKHGRNHKVLDVLCSLCVCHGVAVRSNQHL | 592-631 |
| hBRR | ICDNLLPRRNLLQTRLINDVTSIRPNIFLGVAEGSAQYK | 619-658 |
| rBRR | ICDNLLPRRNLLQTRLINDVTSIRPNIFLGVAEGSAQYK | 619-658 |
| rSRR | ITENLLPGRELLQTRLINYVTSIRPNIFVGRAEGSTQYG | 621-660 |
| rCRR | ICDNLLPGRDLLQTRLVNHVSSMRPNIFLGVSEGSAQYK | 632-671 |
| hBRR | KWYFELIIDQVDPFLTAEPTHLRVGWASSGYAPYPGGGE | 659-698 |
| rBRR | KWYFELIIDQVDPFLTAEPTHLRVGWASSGYAPYPGGGE | 659-698 |
| rSRR | KWYFEVMVDEVVPFLTAQATHLRVGWALTEGYSPYPGGGE | 661-700 |
| rCRR | KWYYELMVDHTEPFVTAEATHLRVGWASTEGYSPYPGGGE | 672-711 |

FIGURE 1G

| | | | | | |
|---|---|---|---|---|---|
| hBRR | GWGGNGVGDDLYSYGFDGLHLWSGRIPRAVASINQHLLRS | 699-738 |
| rBRR | GWGGNGVGDDLYSYGFDGLHLWSGRIPRAVASINQHLLKS | 699-738 |
| rSRR | GWGGNGVGDDLYSYGFDGLHLWTGHVARPVTSPGQHLLAP | 701-740 |
| rCRR | EWGGNGVGDDLFSYGFDGLHLWSGCIARTVSSPNQHLLRT | 712-751 |

| | | |
|---|---|---|
| hBRR | DDVGKLLPGPRGCPASHSASMGSPCRGCLENFNTDGLFFP | 739-778 |
| rBRR | DDVVSCCLD-LGVPSISFRINGQPVQGMFENFNTDGLFFP | 739-777 |
| rSRR | EDVVSCCLD-LSVPSISFRINGCPVQGVFEAFNLDGLFFP | 741-779 |
| rCRR | DDVISCCLD-LSAPSISFRINGQPVQGMFENENIDGLFFP | 752-790 |

| | | |
|---|---|---|
| hBRR | VMSFSAGVKVRFLMGGRHGEEFKFLPPSGYAPCYEALLPKE | 779-818 |
| rBRR | VMSFSAGVKVRFLMGGRHGEEFKFLPPSGYAPCYEALLPKE | 778-817 |
| rSRR | VVSFSAGVKVRFLLGGRHGEEFKFLPPPGYAPCHEAVLPRE | 780-819 |
| rCRR | VVSFSAGIKVRFLLGGRHGEEFKFLPPPGYAPCYEAVLPKE | 791-830 |

FIGURE 1H

```
hBRR  KMRLEPVKEYKRDADGIRDLLGTTQFLSQASFIPCPVDTS  819-858
rBRR  KMRLEPVKEYKRDAEGVRDLLGTTQFLSQASFIPCPIDTS  818-857
rSRR  RLRLEPIKEYRREGPRGPHLVGPSRCLSHTDFVPCPVDTV  820-859
rCRR  KLKVEHSREYKQERTYTRDLLGPTVSLTQAAFTPIPVDTS  831-870 hBRR  QVILPPHLEKIRDRLAENIHELWGMNKIELGWTFGKIRDD  859-898
rBRR  QVVLPPHLEKIRDRLAENIHELWGMNKIELGWTFGKMRDD  858-897
rSRR  QIVLPPHLERIREKLAENIHELWAITRIEQGWTYGPVRDD  860-899
rCRR  QIVLPPHLERIREKLAENIHELWVMNKIELGWQYGPVRDD  871-910 hBRR  NKRQHPCLVEFSKLPETEKNYNLQMSTETLKTLLTLGCHI  899-938
rBRR  NKRQHPCLVEFSKLPETEKNYNLQMSTETLKTLLALGCHI  898-937
rSRR  NKRLHPCLVNFHSLPEPERNYNLQMSGETLKTLLALGCHV  900-939
rCRR  NKRQHPCLVEFSKLPEQERNYNLQMSLETLKTLLALGCHV  911-950
```

FIGURE 1I

| | | | |
|---|---|---|---|
| hBRR | AHVNPAAEEDLKKVKLPKNYMMSNGYKPAPLDLSDVKLLP | 939-978 |
| rBRR | AHVNPAAEEDLKKVKLPKNYMMSNGYKPAPLDLSDVKLLP | 938-977 |
| rSRR | GMADEKAEDNLKKTKLPKTYMMSNGYKPAPLDLSHVRLTP | 940-979 |
| rCRR | GISDEHAEEKVKKMKLPKNYQLTSGYKPAPMDLSFIKLTP | 951-990 |
| | | |
| hBRR | PQEILVDKLAENAHNVWAKDRIKQGWTYGIQQDLKNKRNP | 979-1018 |
| rBRR | PQEILVDKLAENAHNVWAKDRIKQGWTYGIQQDLKNKRNP | 978-1017 |
| rSRR | AQTTLVDRLAENGHNVWARDRVAQGWSYSAVQDIPARRNP | 980-1019 |
| rCRR | SQEAMVDKLAENAHNVWARDRIRQGWTYGIQQDVKNRRNP | 991-1030 |
| | | |
| hBRR | RLVPYALLDERTKKSNRDSLREAVRTFVGYGYNIEPSDQE | 1019-1058 |
| rBRR | RLVPYALLDERTKKSNRDSLREAVRTFVGYGYNIEPSDQE | 1018-1057 |
| rSRR | RLVPYRLLDEATKRSNRDSLCQAVRTLLGYGYNIEPPDQE | 1020-1059 |
| rCRR | RLVPYTLLDDRTKKSNKDSLREAVRTLLGYGYNLEAPDQD | 1031-1070 |

FIGURE 1J

| | | | |
|---|---|---|---|
| hBRR | LADSA-VEKVSI-DKIRFFRVERSYPVRSGKWYFEFEVVT | 1059-1096 |
| rBRR | LADPA-VEKVSI-DKIRFFRVERSYAVRSGKWYFEFEVVT | 1058-1095 |
| rSRR | ---PSQVENQSRWDRVRIFRAEKSYTVQSGRWYFEFEAVT | 1060-1096 |
| rCRR | HAARAEVCSGTG-ERFIFRAEKTYAVKAGRWYFEFEAVT | 1071-1109 |

| hBRR | GGDMRVGWARPGCRPDVELGADDQAFVFEGNRGQRWHQGS | 1097-1136 |
| rBRR | GGDMRVGWARPGCRPDIELGPMTKPLCLKAAGASVGTKVV | 1096-1135 |
| rSRR | TGEMRVGWARPELRPDVELGADELAYVFNGHRGQRWHLGS | 1097-1136 |
| rCRR | SGDMRVGWSRPGCQPDQELGSDERAFAFDGFKAQRWHQGN | 1110-1149 |

| hBRR | GYFGRTWQPGDVVGCMINLDDASMIFTLNGELLITNKGSE | 1137-1176 |
| rBRR | GILGVPWQPGDVVGCMINLDDASMIFTLNGELLITNKGSE | 1136-1175 |
| rSRR | EPFGRPWQSGDVVGCMIDLTENTIIFTLNGEVLMSDSGSE | 1137-1176 |
| rCRR | EHYGRSWQAGDVVGCMVDMNEHTMMFTLNGEILLDDSGSE | 1150-1189 |

FIGURE 1K

```
hBRR  LAFADYEIENGFVPICCLGLSQIGRMNLGTDASTFKFYTM  1177-1216
rBRR  LAFADYEIENGFVPICSLGLSQIGRMNLGTDASTFKFYTM  1176-1215
rSRR  TAFREIEIGDGFLPVCSLGPGQVGHLNLGQDVSSLRFFAI  1177-1216
rCRR  LAFKDFDVGDFIPVCSLGVAQVGRMNFGKDVSTLKYFTI   1190-1229 hBRR  CGLQEGFEPFAVNMNRDVAMWFSKRLPTFVNVPKDHPHIE  1217-1256
rBRR  CGLQEGFEPFAVNMNRDVAMWFSKRLPTFVNVPKDHPHIE  1216-1255
rSRR  CGLQEGFEPFAINMQRPVTTWFSKSLPQFEPVPPEHPHYE  1217-1256
rCRR  CGLQEGYEPFAVNTNRDITMWLSKRLPQFLQVPSNHEHIE  1230-1269 hBRR  VMRIDGTMDSPPCLKVTHKTFGTQNSNADMIYCRLSMPVE  1257-1296
rBRR  VVRIDGTMDSPPCLKVTHKTFGTQNSNANMIYCRLSMPVE  1256-1295
rSRR  VARMDGTVDTPPCLRLAHRTWGSQNSLVEMLFLRLSLPVQ  1257-1296
rCRR  VTRIDGTIDSSPCLKVTQKSFGSQNSNTDIMFYRLSMPIE  1270-1309
```

FIGURE 1L

```
hBRR  CHSSFS----------------------------------------  1297-1302
rBRR  CHSSFS----------------------------------------  1296-1301
rSRR  FHQHFRCTAGATPLAPPGLQPPAEDEARAAEPDPDYENLR        1297-1336
rCRR  CAEVFSKTV-PGGLPGAGLFGPKNDLEDY-DADSDFEVLM        1310-1347 hBRR  ----------------------------------------------  1302-1302
rBRR  ----------------------------------------------  1301-1301
rSRR  RSAGGWGEAEGGKEGTAKEGTPGGTPQPGVEAQPVRAENE        1337-1376
rCRR  KTAHG--HLVPDRVDKDKETTKA-------EFNNH              1348-1373 hBRR  ----------------------------------HSPCLDS        1303-1309
rBRR  ----------------------------------HSPCLDS        1302-1308
rSRR  KDATTEKNK--KRGFLEKAKKAAMMTQPP-ATPALPRLPH        1377-1413
rCRR  KDYAQEKPSRLKQRFLLRR-----TKPDYSTSHSARLTE        1374-1407
```

FIGURE 1M

```
hBRR  EAF-QKRKQMEILSHTTTQCYYAIRIFGGQDPSCVWVGW       1310-1348
rBRR  EAF-QKRKQMEILSHTTTQCFYSIRIFAGQDPSCVWVGW       1309-1347
rSRR  DVVPADNRDDPEILNTTI-YYYSVRVFAGQEPSCVWVGW       1414-1452
rCRR  DVL-ADDRDDYDFLMQTSI-YYYSVRIEPGQEPANVWVGW      1408-1445 hBRR  VTPDYHLYSEKFDLNKNCTVTVTLGDERGRVHESVKRSNC      1349-1388
rBRR  VTPDYHLYSEKFDLNKNCTVTVTLGDERGRVHESVKRSNC      1348-1387
rSRR  VTPDYHQHDMNFDLSKVRAVTVTMGDEQGNVHSSLKCSNC      1453-1492
rCRR  ITSDFHQYDTGFDLDRVRTVTVTLGDEKGKVHESIKRSNC      1446-1485 hBRR  YMVWGGDIVASSQRSNRSNVDLEIGCLVDLAMGMLSFSAN      1389-1428
rBRR  YMVWGGDIVASSQRSISRSNVDLEIGCLVDLAMGMLSFSAN     1388-1427
rSRR  YMVWGGDFVSPGQQGRISHTDLVIGCLVDLATGLMTFTAN      1493-1532
rCRR  YMVCAGESMSPGQ-GRNNNG-LEIGCVVDAASGLLTFIAN      1486-1523
```

FIGURE 1N

| | | | | |
|---|---|---|---|---|
| hBRR | GKELGTCYQVEPNTKVFPAVFLQPTSTSLFQFELGKLKNA | 1429-1468 |
| rBRR | GKELGTCYQVEPNTKVFPAVFLQPTSTSLFQFELGKLKNA | 1428-1467 |
| rSRR | GKESNTFFQVEPNTKLFPAVFVLPTHQNVIQFELGKQKNI | 1533-1572 |
| rCRR | GKELSTYYQVEPSTKLFPAVFAQATSPNVFQFELGRIKNV | 1524-1563 |
| hBRR | MPLSAAIFRSEEENPVPQCPPRLDVQTIQPVLWSRMPNSF | 1469-1508 |
| rBRR | MPLSAAIFKSEEKNPVPQCPPRLDVQTIQPVLWSRMPNSF | 1468-1507 |
| rSRR | MPLSAAMFLSERKNPAPQCPPRLEVQMLMPVSWSRMPNHF | 1573-1612 |
| rCRR | MPLSAGLFKSEHKNPVPQCPPRLHVQFLSHVLWSRMPNQE | 1564-1603 |
| hBRR | LKVETERVSERHGWVVQCLEPLQMMALHIPEENRCVDILE | 1509-1548 |
| rBRR | LKVETERVSERHGWVVQCLEPLQMMALHIPEENRCVDILE | 1508-1547 |
| rSRR | LQVETRRAGERLGWAVQCQDPLTMMALHIPEENRCMDILE | 1613-1652 |
| rCRR | LKVDVSRISEQGWLVQCLDPLQFMSLHIPEENRSVDILE | 1604-1643 |

FIGURE 10

| | | | | | |
|---|---|---|---|---|---|
| hBRR | LCEQEDLMRFHYHTLRLYSAVCALGNSRVAYALCSHVDLS | 1549-1588 |
| rBRR | LCEQEDLMQFHYHTLRLYSAVCALGNSRVAYALCSHVDLS | 1548-1587 |
| rSRR | LSERLDLQRFHSHTLRLYRAVCALGNNRVAHALCSHVDQA | 1653-1692 |
| rCRR | LTEQEELLKEFHYHTLRLYSAVCALGNHRVAHALCSHVDEP | 1644-1683 |
| | | |
| hBRR | QLFYAIDNKYLPGLLRSGFYDLLISIHLASAKERKLMMKN | 1589-1628 |
| rBRR | QLFHAIDNKYLPGLLRSGFYDLLISIHLANAKERKLMMKN | 1588-1627 |
| rSRR | QLHALEDAHLPGPLRAGYYDLLISIHLESACRSRRSMLS | 1693-1732 |
| rCRR | QLLYAIENKYMPGLLRTGYYDLLIDIHLSSYATARLMMNN | 1684-1723 |
| | | |
| hBRR | EYIIPITSTTRNICLFP----DESKRHGLPGVGLRTCL | 1629-1662 |
| rBRR | EYIIPITSTTRNIRLYP----DESKKHGLPGVGPRTCL | 1628-1661 |
| rSRR | EYIVPLTPETRAITLFPPGRKGGNA-RRHGLPGVGVTTSL | 1733-1771 |
| rCRR | EFIVPMTEETKSITLFP----DENKKHGLPGIGLSTSL | 1724-1757 |

FIGURE 1P

| | | | | | |
|---|---|---|---|---|---|
| hBRR | KPGFRFSTPCFVV | ------ | TGEDHQKQ | SPEIPLES | LRTKA | 1663-1696 |
| rBRR | KPGFKFSTPCFVV | ------ | TNEERQKQ | SPEIPLEI | LKMKA | 1662-1695 |
| rSRR | RPPHHFSPPCFVAALPAAGVAEAPARLSPAIPLEA | LRDKA | 1772-1811 |
| rCRR | RPRMQFSSPSFVS | ------ | INNECYQYS | PEFPLDI | LKAKT | 1758-1791 |

| | | | | |
|---|---|---|---|---|
| hBRR | LSMLTEAVQCS | GAHIRDPVGGS | VEFQFVPVLKL | IGTLLVM | 1697-1736 |
| rBRR | LSMLTEAVQCS | GAHIRDPVGGS | VEFQFVPVLKL | VGTLLVM | 1696-1735 |
| rSRR | LRMLGEAVRDGG | QHARDPVGGS | VEFQFVPVLKL | VSTLLVM | 1812-1851 |
| rCRR | IQMLTEAVKEGS | LHARDPVGGTT | EFLFVPLIKL | FYTLLIM | 1792-1831 |

| | | | |
|---|---|---|---|
| hBRR | GVFDDDDVRQ | ILLIIDPSVFGEHSAG | --------- | 1737-1762 |
| rBRR | GVFCDDDVRQ | ILLIIDPSVFGEHSAD | --------- | 1736-1761 |
| rSRR | GIFGDEDVKQ | ILKMIEPEVFTEEEEEEEEEEEEED | 1852-1891 |
| rCRR | GIEHNEDLRH | ILQLIEPSVFKDAATP | --------- | 1832-1857 |

FIGURE 1Q

```
hBRR  TEEGAEKEEVTQVEEKAVE-AGEKAG------KEAPVKGLLQ  1763-1797
rBRR  TEEGAEKEEVSQVEEKAVE-AGEKTSKEARKEAPVRGLLQ    1762-1800
rSRR  EEEKEEDEEEEEKEDAEKE-----EEEAPEGEKEDLEEGLLQ  1892-1928
rCRR  EEEGDTLEEEPSVEDTKLEGAGEEEAKMGKR--PKEGLLQ    1858-1895 hBRR  TRLPESVKLQMCELLSYLCDCELQHRVEAIVAFGDIYVSK    1798-1837
rBRR  TRLPESVKLQMCELLSYLCDCELQHRVEAIVAFGDIYVSK    1801-1840
rSRR  MKLPESVKLQMCNLLEYFCDQELQHRVESLAAFAERYVDK    1929-1968
rCRR  MKLPEPVKLQMCLLLQYLCDCQVRHRIEAIVAFSDDFVAK    1896-1935 hBRR  LQANQKFRYNELMQALNMSAALTARKTKEFRSPPQEQINM    1838-1877
rBRR  LQANQKFRYNELMQALNMSAALTARKTREFRSPPQEQINM    1841-1880
rSRR  LQANQRSRYALLMRAFTMSAAETARRTREFRSPPQEQINM    1969-2008
rCRR  LQDNQRFRYNEVMQALNMSAALTARKTKEFRSPPQEQINM    1936-1975
```

FIGURE 1R

| | | | | | |
|---|---|---|---|---|---|
| hBRR | LLNFQ---LGE | NCPCPEEIRE | ELYDFHEDLL | HCGVPLEE | 1878-1914 |
| rBRR | LLNFQ---LGE | NCPCPEEIRE | ELYDFHEDLL | VHCGVPLEE | 1881-1917 |
| rSRR | LLHFKDEADEE | DCPLPEDIRQ | DLQDFHQDLL | AHCGIQLEG | 2009-2048 |
| rCRR | LLNFKD---DKS | ECPCPEEIRD | QLLDFHEDLM | THCGIELDE | 1976-2013 |
| | | | | | |
| hBRR | EEEEEDTS-- | -WTGKLCALVY | KIKGPPKPEKE | QPTEE---- | 1915-1949 |
| rBRR | EEEEEDTS-- | -WTGKLRTLVY | KIKGPPKPEKE | QPTEE---- | 1918-1952 |
| rSRR | EEEPEEET-S | LSSRLRSLLE | TVR-LVKKKEEK | PEEELPA | 2049-2086 |
| rCRR | DGSLDGNSDL | TIRGRLLSLVE | KVTYLKKQTEK | PVES---- | 2014-2050 |
| | | | | | |
| hBRR | EERCPTTLKE | LISQTMICWA | QEDQIQDSELV | RMMFNLLRR | 1950-1989 |
| rBRR | EERCPTTLKE | LISQTMIRWA | QEDQIQDAELV | RMMFNLLRR | 1953-1992 |
| rSRR | EEKKPQSLQE | LVSHMVVRWA | QEDYVQSPELV | RAMFSLLHR | 2087-2126 |
| rCRR | DSRKSSTLQQ | LISETMVRWA | QESVIEDPELV | RAMFVLLHR | 2051-2090 |

*FIGURE 1S*

```
hBRR  QYDSIGELLQALRKTYTISHTSVSDTINLLAALGQIRSLL  1990-2029
rBRR  QYDSIGELLQALRKTYTISHASVSDTINLLAALGQIRSLL  1993-2032
rSRR  QYDGLGELLRALPRAYTISPSSVEDTMSLLECLGQIRSLL  2127-2166
rCRR  QYDGIGGLVRALPKTYTINGVSVEDTINLLASLGQIRSLL  2091-2130 hBRR  SVRMGKEEELLMINGLGDIMNNKVFYQHPNLMRVLGMHET  2030-2069
rBRR  SVRMGREEELLMINGLGDIMNNKVFYQHPNLMRVLGMHET  2033-2072
rSRR  IVQMGPQEENLMIQSIGNIMNNKVFYQHPNLMRALGMHET  2167-2206
rCRR  SVRMGKEEEKLMIRGLGDIMNNKVFYQHPNLMRALGMHET  2131-2170 hBRR  VMEVMVNVLGT-EKSQIAFPKMVASCCRFLCYFCRISRQN  2070-2108
rBRR  VMEVMVNVLGT-EKSQIAFPKMVASCCRFLCYFCRISRQN  2073-2111
rSRR  VMEVMVNVLGGGETKEIRFPKMVTSCCRFLCYFCRISRQN  2207-2246
rCRR  VMEVMVNVLGGESKEITFPKMVANCCRFLCYFCRISRQN   2171-2210
```

FIGURE 1T

```
hBRR  QKAMFEHLSYLLENSSVGLASPSMRGSTPLDVAASSVMDN  2109-2148
rBRR  QKAMFEHLSYLLENSSVGLASPSMRGSTPLDVAASSVMDN  2112-2151
rSRR  QRSMFDHLSYLLENSGIGLG---MQGSTPLDVAAASVIDN  2247-2283
rCRR  QKAMFDHLSYLLENSSVGLASPAMRGSTPLDVAAASVMDN  2211-2250 hBRR  NELALSLEEPDLEKVVTYLAGCGLQSCPMLLAKGYPDVGW  2149-2188
rBRR  NELALGLEEPDLEKVVTYLAGCGLQSCPMLLAKGYPDVGW  2152-2191
rSRR  NELALALQEQDLEKVVSYLAGCGLQSCPMLLAKGYPDIGW  2284-2323
rCRR  NELALALREPDLEKVVRYLAGCGLQSCQMLVSKGYPDIGW  2251-2290 hBRR  NPIEGERYLSFLRFAVFVNSESVEENASVVVKLLIRRPEC  2189-2228
rBRR  NPIEGERYLSFLRFAVFVNSESVEENASVVVKLLIRRPEC  2192-2231
rSRR  NPCGGERYLDFLRFAVFVNGESVEENANVVVRLLIRKPEC  2324-2363
rCRR  NPVEGERYLDFLRFAVFCNGESVEENANVVVRLLIRRPEC  2291-2330
```

FIGURE 1U

```
hBRR  FGPALRGEGGNGLLAAMQGAIKISENPALDLPSQ-GYKRE  2229-2267
rBRR  FGPALRGEGGNGLLAAMQGAIKISESPALDLPSQ-GYKRE  2232-2270
rSRR  FGPALRGEGGSGLLAAIEEAIRISEDPARDGPGVRRDRRR  2364-2403
rCRR  FGPALRGEGGNGLLAAMEEAIKIAEDPSRDGPSPTSGSSK  2331-2370 hBRR  VSTEDDEEEIVHMGNAIMSFYSALIDLLGRCAPEMHLI    2268-2307
rBRR  VP-EDGEEEIVHMGNAIMSFYSALIDLLGRCAPEMHLI    2271-2309
rSRR  EHFGEEPPEENRVHLGHAIMSFYAALIDLLGRCAPEMHLI  2404-2443
rCRR  TL-DTEEEDDTIHMGNAIMTFYAALIDLLGRCAPEMHLI   2371-2409 hBRR  QTGKGEAIRIRSILRSLVPTEDLVGIISIPLKLPSLNKDG  2308-2347
rBRR  QTGKGEAIRIRSILRSLVPTEDLVGIISIPLKLPSLNKDG  2310-2349
rSRR  QAGKGEALRIRAILRSLVPLDDLVGIISLPLQIPTLGKDG  2444-2483
rCRR  HAGKGEAIRIRSILRSLIPLGDLVGVISIAFQMPTIAKDG  2410-2449
```

FIGURE 1V

| | | | |
|---|---|---|---|
| hBRR | SVSEPDMAGNFCPDHKAPMVLFLDRVYGIKDQTFLLHLE | 2348-2387 |
| rBRR | SVSEPDMAANFCPDHKAPMVLFLDRVYGIKDQTFLLHLE | 2350-2389 |
| rSRR | ALVQPKMSASFVPDHKASMVLFLDRVYGIENQDFLLHVLD | 2484-2523 |
| rCRR | NVVEPDMSAGFCPDHKAAMVLFLDRVYGIEVQDFLLHLLE | 2450-2489 |

| | | | |
|---|---|---|---|
| hBRR | VGFLPDLRASASLDTVSLSTTEAALALNRYICSAVLPLIT | 2388-2427 |
| rBRR | VGFLPDLRASASLDTVALSTTESALALNRYICSAVLPLIT | 2390-2429 |
| rSRR | VGFLPDMRAAASLDTATFSTTEMALALNRYLCLAVLPLIT | 2524-2563 |
| rCRR | VGFLPDLRAAASLDTAALSATDMALALNRYLCTAVLPLIT | 2490-2529 |

| | | | |
|---|---|---|---|
| hBRR | RCAPLFGGTEHCTSLIDSTLQTIYRLSKGRSLTKAQRDTI | 2428-2467 |
| rBRR | RCAPLFAGTEHYTSLIDSTLQTIYRLSKGRSLTKAQRDTI | 2430-2469 |
| rSRR | KCAPLFAGTEHRAIMVDSMLHTVYRLSRGRSLTKAQRDVI | 2564-2603 |
| rCRR | RCAPLFAGTEHHASLIDSLLHTVYRLSKGCSLTKAQRDSI | 2530-2569 |

FIGURE 1W

| | | | | |
|---|---|---|---|---|
| hBRR | EECLLAICNHLRPSML | QQLLRRLVFDVPQLNEYCKMPLKL | 2468-2507 |
| rBRR | EECLLAICNHLRPSML | QQLLRRLVFDVPQLNDYCKMPLKL | 2470-2509 |
| rSRR | EDCLMALCRYIRPSML | QHLLRRLVFDVPILNEFAKMPLKL | 2604-2643 |
| rCRR | EVCLLSICGQLRPSMM | QHLLRRLVFDVPLLNEHAKMPLKL | 2570-2609 |

| | | | | |
|---|---|---|---|---|
| hBRR | LTNHYEQCWKYYCLPSGWGSYGLAV | EEELHLTEKLFWGII | 2508-2547 |
| rBRR | LTNHFEQCWKYYCLPSGWGSYGLAV | EEELHLTEKLFWGIF | 2510-2549 |
| rSRR | LTNHYERCWKYYCLPTGWANFGVTS | EEELHLTRKLFWGIF | 2644-2683 |
| rCRR | LTNHYERCWKYYCLPGGWGNFGAAS | EEELHLSRKLFWGIF | 2610-2649 |

| | | | | |
|---|---|---|---|---|
| hBRR | DSLSHKKYDPDLFRMALPCLSAIAGALPPDYLDSRITATL | 2548-2587 |
| rBRR | DSLSHKKYDPDLFRMSLPCLSAIAGALPPDYLDTRITATL | 2550-2589 |
| rSRR | DSLAHKKYDQELYRMAMPCLCAIAGALPPDYVDASYSKA | 2684-2723 |
| rCRR | DALSQKKYEQELFKLALPCLSAVAGALPPDYMESNYVSMM | 2650-2689 |

FIGURE 1X

```
hBRR  EKQISVDADGNFDPKPINTMNFSLPEKLEYIVTKYAEHSH  2588-2627
rBRR  EKQVSVDADGNFDPKPINTINFSLPEKLEYIVTKYAEHSH  2590-2629
rSRR  EKKATVDAEGNFDPRPVETLNVIIPEKLDSFINKFAEYTH  2724-2763
rCRR  EKQSSMDSEGNENPQPVDTSNIIPEKLEYFINKYAEHSH  2690-2729 hBRR  DKWACDKSQSGWKYGISLDENVKTHPLIRPFKTLTEKEKE  2628-2667
rBRR  DKWACEKSQSGWKYGISLDENVKTHPLIRPFKTLTEKEKE  2630-2669
rSRR  EKWAFDKIQNNWSYGENVDEELKTHPMLRPYKTFSEKDKE  2764-2803
rCRR  DKWSMDKLANGWIYGEIYSDSSKIQPLMKPYKLLSEKEKE  2730-2769 hBRR  IYRWPARESLKTMLAVGWTVERTKEGEALVQQRENEKLRS  2668-2707
rBRR  IYRWPARESLKTMLAVGWTVERTKEGEALVQLRENEKLRS  2670-2709
rSRR  IYRWPIKESLKAMIAWEWTIEKAREGEE--ERTEKKKTRK  2804-2841
rCRR  IYRWPIKESLKTMLAWGWRIERTREGDS---MALYNRTRR  2770-2806
```

FIGURE 1Y

| | | | |
|---|---|---|---|
| hBRR | VSQANQ------GNSYSPAPLDLSNVVLSRELQGMVEVVAE | 2708-2742 |
| rBRR | VSQTSQ------GNSYNPAPLDLSNVVLSRELQGMVEVVAE | 2710-2744 |
| rSRR | ISQTAQ-TYDPREGYNPQPPDLSGVTLSRELQAMAEQLAE | 2842-2880 |
| rCRR | ISQTSQVSVDAAHGYSPRAIDMSNVTLSRDLHAMAEMMAE | 2807-2846 |
| | | |
| hBRR | NYHNIWAKKKLELESKGGGSHPLLVPYDTLTAKEKFKDR | 2743-2782 |
| rBRR | NYHNIWAKKKLELESKGGGSHPLLVPYDTLTAKEKFRDR | 2745-2784 |
| rSRR | NYHNTWGRKKQELEAKGGGTHPLLVPYDTLTAKEKARDR | 2881-2920 |
| rCRR | NYHNIWAKKKLELESKGGGNHPLLVPYDTLTAKEKAKDR | 2847-2886 |
| | | |
| hBRR | EKAQDLFKFLQVNGIIVSRGMKDMELDASSMEKRFGYKFL | 2783-2822 |
| rBRR | EKAQDLFKFLQVNGVIVSRGMKDMELDAFSMEKRFAYKFL | 2785-2824 |
| rSRR | EKAQELLKFLQMNGYAVTRGLKDMELDTSSIEKRFAFGFL | 2921-2960 |
| rCRR | EKAQDILKFLQINGYAVSRGFKDLELDTPSIEKRFAYSFL | 2887-2926 |

FIGURE 1Z

```
hBRR  KKILKYVDSAQEFIAHLEAIVSSGKTEKSPRDQEIKFFAK   2823-2862
rBRR  KKILKYVDSAQEFIAHLEAIVSSGKTEKSPHDQEIKFFAK   2825-2864
rSRR  QQLLRWMDISQEFIAHLEAVVSSGRVEKSPHEQEIKFFAK   2961-3000
rCRR  QQLIRYVDEAHQYILEFDG-SRSKGEHFPYEQEIKFFAK    2927-2965 hBRR  VLLPLVDQYFTSHCLYFLSSPLKPLSSSGYASHKEKEMVA   2863-2902
rBRR  VLLPLVDQYFTNHRLYFLSSPLKPLSSSGYASHKEKEMVA   2865-2904
rSRR  ILLPLINQYFTNHCLYFLSTPAKVLGSSGHASNKEKEMIT   3001-3040
rCRR  VVLPLIDQYEKNHRLYFLSAASRPLCSGGHASNKEKEMVT   2966-3005 hBRR  GLFCKLAALVRHRISLFGSDSTTMVSCLHILAQTLDTRTV   2903-2942
rBRR  SLFCKLAALVRHRISLFGSDSTTMVSCLHILAQTLDTRTV   2905-2944
rSRR  SLFCKLAALVRHRVSLFGTDAPAVVNCLHILARSLDARTV   3041-3080
rCRR  SLFCKLGVLVRHRISLFGNDATSIVNCLHILGQTLDARTV   3006-3045
```

FIGURE 1AA

```
hBRR  MKSGSELVKAGLRAFFENAAEDLEKTSENLKLGKFTHSRT  2943-2982
rBRR  MKSGSELVKAGLRAFFESAAEDLEKTSENLKLGKFTHSRT  2945-2984
rSRR  MKSGPEIVKAGLRSFFESASEDIEKMVENLRLGKVSQART  3081-3120
rCRR  MKTGLESVKSALRAFLDNAAEDLEKTMENLKQGQFTHTRN  3046-3085 hBRR  QIKGVSQNINYTTVALLPILTSIFEHVTQHQFGMDLLLGD  2983-3022
rBRR  QIKGVSQNINYTTVALLPILTSIFEHVAQHQFGVDLLLGD  2985-3024
rSRR  QVKGVGQNLTYTTVALLPVLTTLFQHIAQHQFGDDVILDD  3121-3160
rCRR  QPRGVTQIINYTTVALLPMLSSLFEHIGQHQFGEDLILED  3086-3125 hBRR  VQISCYHILCSLYSLGTGKNIYVERQRPALGECLASLAAA  3023-3062
rBRR  VQISCYRILCSLYSLGTGKNIYVERQRPALGECLASLAAA  3025-3064
rSRR  VQVSCYRTLCSIYSLGTTKNTYVEKLRPALGECLARLAAA  3161-3200
rCRR  VQVSCYRILTSLYALGTSKSIYVERQRSALGECLAAFAGA  3126-3165
```

FIGURE 1BB

| | | | | |
|---|---|---|---|---|
| hBRR | IPVAFLEPTLNRYNPLSVFNTKTPRERSILGMPDTVEDMC | 3063–3102 |
| rBRR | IPVAFLEPTLNRYNALSVFNTKTPRERSILGMPDTVEEMC | 3065–3104 |
| rSRR | MPVAFLEPQLNEYNACSVYTTKSPRERAILGLPNSVEEMC | 3201–3240 |
| rCRR | FPVAFLETHLNKHNIYSIYNTKSSRERAALSLPANVEDVC | 3166–3205 |

| | | | | |
|---|---|---|---|---|
| hBRR | PDIPQLEGLMKEINDLAESGARYTEMPHVIEVILPMLCNY | 3103–3142 |
| rBRR | PDIPQLEGLMKEINDLAESGARYTEMPHVIEVILPMLCNY | 3105–3144 |
| rSRR | PDIPVLDRLMADIGGLAESGARYTEMPHVIEITLPMLCSY | 3241–3280 |
| rCRR | PNIPSLEKLMEEIVELAESGIRYTQMPHVMEVILPMLCSY | 3206–3245 |

| | | | | |
|---|---|---|---|---|
| hBRR | LSYWWERGPEN————LPPSTGPCCTKVTSEHLSLILGNIL | 3143–3178 |
| rBRR | LSYWWERGPEN————LSPSTGPCCSKVTSEHLSLILGNIL | 3145–3180 |
| rSRR | LPRWWERGPEAPPPALPAGAPPPCTAVTSDHLNSLLGNIL | 3281–3320 |
| rCRR | MSRWWEHGPES————NPGRAEMCCTALNSEHMNTLLGNIL | 3246–3281 |

FIGURE 1CC

```
hBRR  KIINNNLGIDEASWMKRIAVYAQPIISKARPDLLRSHFIP  3179-3218
rBRR  KIINNNLGIDEASWMKRIAVYAQPIISKARPDLLRSHFIP  3181-3220
rSRR  RIIVNNLGIDEATWMKRLAVFAQPIVSRARPELLHSHFIP  3321-3360
rCRR  KIIYNNLGIDEGAWMKRLAVFSQPIINKVKPQLLKTHFLP  3282-3321 hBRR  TLEKLKKAVKTVQEEQLKADGKGDTQEAELLILDEFAV     3219-3258
rBRR  TLEKLKKAVKTVQEEQLKADGKGDTQEAELLILDEFAI     3221-3260
rSRR  TIGRLRKRAGKVVAEEQLRLEAKAEAEEGELLVRDEFSV   3361-3400
rCRR  LMEKLKKAAMVVSEEDHLKAEARGDMSEAELLILDEFIT   3322-3361 hBRR  LCRDLYAFYPMLIRYVDNNRSNWLKSPDADSDQLFRMVAE  3259-3298
rBRR  LCRDLYAFYPMLIRYVDNNRSNWLKSPDGDSDQLFRMVAE  3261-3300
rSRR  LCRDLYALYPLLIRYVDNNRAHWLTEPNANAEELFRMVGE  3401-3440
rCRR  LARDLYAFYPLLIRFVDYNRAKWLKEPTPEAEELFRMVAE  3362-3401
```

FIGURE 1DD

```
hBRR  VFILWCKSHNFKREEQNFVIQNEINNLAFLTGDSKSKMS-  3299-3337
rBRR  VFILWCKSHNFKREEQNFVIQNEINNLAFLTGDSKSKMSK  3301-3340
rSRR  IFIYSKSHNFKREEQNFVIQNEINNMSFLTADSKSKMAK   3441-3480
rCRR  VFIYWSKSHNFKREEQNFVVQNEINNMSFLTDTKSKMSK   3402-3441 hBRR  ----KSGGDQERKKTKRRGDLYSIQTSLIVAALKKMLPI   3338-3373
rBRR  AMQVKSGGDQERKKTKRRGDLYSIQTSLIVAALKKMLPI   3341-3380
rSRR  AGDAQSGSDQERTKKKRRGDRYSVQTSLIVATLKKMLPI   3481-3520
rCRR  A-----AVSDQERKKMKRKGDRYSMQTSLIVAALKRLLPI  3442-3476 hBRR  GLNMCTPGDQELISLAKSRYSHRDTDEEVREHLRNNLHLQ  3374-3413
rBRR  GLNMCTPGDQELISLAKSRYSYRDTDEEVKEHLRNNLHLQ  3381-3420
rSRR  GLNMCAPTDQDLIMLAKTRYALKDTDEEVREFLQNNLHLQ  3521-3560
rCRR  GLNICAPGDQELIALAKNRFSLKDTEDEVRDIIRNNIHLQ  3477-3516
```

FIGURE 1EE

| | | | |
|---|---|---|---|
| hBRR | EKSD--DPAVKWQLNLYKDVL-KSEEPFNPEKTVERVQRIS | 3414-3451 |
| rBRR | EKSD--DPAVKWQLNLYKDVL-KSEEPSNPEKTVERVQRIS | 3421-3458 |
| rSRR | GKVEGSPSLRWQMALYRGLPGREDADPEKIVRRVQEVS | 3561-3600 |
| rCRR | GKLE--DPAIRWQMALYKDLPNRTEETSDPEKTVERVLDIA | 3517-3555 |

| | | | |
|---|---|---|---|
| hBRR | AAVFHLEQ--------------VEQPLRSKKAVWHKLLSKQR | 3452-3479 |
| rBRR | AAVFHLEQ--------------VEQPLRSKKAVWHKLLSKQR | 3459-3486 |
| rSRR | AVLYHLEQ--------------TEHPYKSKKAVWHKLLSKQR | 3601-3628 |
| rCRR | NVLFHLEQKSKFIGRRYYNLVEHPQRSKKAVWHKLLSKQR | 3556-3595 |

| | | | |
|---|---|---|---|
| hBRR | KRAVVACFRMAPLYNLPRHRSINLFLHGYQRFWIETEEYS | 3480-3519 |
| rBRR | KRAVVACFRMAPLYNLPRHRSINLFLHGYQRFWIETEEYS | 3487-3526 |
| rSRR | RRAVVACFRMTPLYNLPTHRACNMFLESYKAAWILTEDHS | 3629-3668 |
| rCRR | KRAVVACFRMAPLYNLPRHRAVNLFLQGYEKSWIETEEHY | 3596-3635 |

FIGURE 1FF

```
hBRR  FEEKLVQDLAKSPKVEEEEETEKQPDPLHQIILYFSRN       3520-3559
rBRR  FEEKLVQDLAKSPKVEEEEEMEKQPDPLHQILHFSRN        3527-3566
rSRR  FEDRMIDDLSKAGEQEEEEVEEKKPDPLHQLVLHFSRT       3669-3708
rCRR  FEDKLIEDLAK-PGAEPPEEDEVTKRVDPLHQLILLFSRT     3636-3674 hBRR  ALTERSKLEDDPLYTSYSSMMAKSCQSGE----DEEDED      3560-3595
rBRR  ALTERSKLEDDPLYTSYSSMMAKSCQSGE----DEE-ED      3567-3601
rSRR  ALTEKSKLEDYLMAYADIMAKSCHLEEGGENGEAEEE        3709-3748
rCRR  ALTEKCKLEEDFLYMAYADIMAKSCHDEE----DDDGEE      3675-3709 hBRR  KEKTFEEKEMEKQKTLYQQARLHERGAAEMVLQMISASKG     3596-3635
rBRR  KEKTFEEKEMEKQKTLYQQARLHERGAAEMVLQMISASKG     3602-3641
rSRR  VEVSFEEKEMEKQRLLYQQSRLHTRGAAEMVLQMISACKG     3749-3788
rCRR  EVKSFEEKEMEKQKLLYQQARLHDRGAAEMVLQTISASKG     3710-3749
```

FIGURE 1GG

| | | | | |
|---|---|---|---|---|
| hBRR | EMSPMVVETLKLGIAILNGGNAGVQQKMLDYLKEKKDAGF | 3636–3675 |
| rBRR | EMSPMVVETLKLGIAILNGGNAGVQQKMLDYLKVKKDAGF | 3642–3681 |
| rSRR | ETGAMVSSTLKLGISILNGGNAEVQQKMLDYLKDKKEVGF | 3789–3828 |
| rCRR | ETGPMVAATLKLGIAILNGGNSTVQQKMLDYLKEKKDVGF | 3750–3789 |

| | | | | |
|---|---|---|---|---|
| hBRR | FQSLPGLMQSCSVLDLNASERQNKAEGLGMVTEEGTLIVR | 3676–3715 |
| rBRR | FQSLSGLMQSCSVLDLNAFERQNKAEGLGMVTEEGTLIVR | 3682–3721 |
| rSRR | FQSIQALMQTCSVLDLNAFERQNKAEGLGMVNEDGTVINR | 3829–3868 |
| rCRR | FQSLAGLMQSCSVLDLNAFERQNKAEGLGMVTEEGS---  | 3790–3825 |

| | | | | |
|---|---|---|---|---|
| hBRR | ERGEKVLQNDEFTRDLFRFLQLLCEGHNSDFQNFLRTQMG | 3716–3755 |
| rBRR | ERGEKVLQNDEFTRDLFRFLQLLCEGHNSDFQNFLRTQMG | 3722–3761 |
| rSRR | QNGEKVMADDEFTQDLFRFLQLLCEGHNNDFQNYLRTQTG | 3869–3908 |
| rCRR | --GEKVLQDDEFTCDLFRFLQLLCEGHNSDFQNYLRTQTG | 3826–3863 |

FIGURE 1HH

| | | | | | |
|---|---|---|---|---|---|
| hBRR | NTTTVNVI | ISTVDYLLRL | QESISDFYWYYSGKD | IIDESGQ | 3756-3795 |
| rBRR | NTTTVNVI | ISTVDYLLRL | QESISDFYWYYSGKD | IIDESGQ | 3762-3801 |
| rSRR | NTTTINII | ICTVDYLLRL | QESISDFYWYYSGKD | VIEEQGK | 3909-3948 |
| rCRR | NNTTVNII | ISTVDYLLRV | QESISDFYWYYSGKD | VIDEQGQ | 3864-3903 |

| | | | | | |
|---|---|---|---|---|---|
| hBRR | HNFSKALA | VTKQIFNSL | TEYIQGPCIGNQQSLAHSRLWDA | | 3796-3835 |
| rBRR | HNFSKALA | VTKQIFNSL | TEYIQGPCIGNQQSLAHSRLWDA | | 3802-3841 |
| rSRR | RNFSKAMS | VAKQVFNSL | TEYIQGPCTGNQQSLAHSRLWDA | | 3949-3988 |
| rCRR | RNFSKAIQ | VAKQVENTL | TEYIQGPCTGNQQSLAHSRLWDA | | 3904-3943 |

| | | | | | |
|---|---|---|---|---|---|
| hBRR | VVGFLHVFEANM | QMKLSQDSSQIELLKELL | DLL | QDMVVMLL | 3836-3875 |
| rBRR | VVGFLHVFEANM | QMKLSQDSSQIELLKELL | DLL | QDMVVMLL | 3842-3881 |
| rSRR | VVGFLHVFEAHMM | MKLAQDSSQIELLKELL | DLL | QKDMVVMLL | 3989-4028 |
| rCRR | VVGFLHVFEAHM | QMKLSQDSSQIELLKELM | DLQ | KDMVVMLL | 3944-3983 |

FIGURE 1II

```
hBRR  SLLEGNVVNGTIGKQMVDTLVESSTNVEMILKFFDMFLKL  3876-3915
rBRR  SLLEGNVVNGTIGKQMVDTLVESSTNVEMILKFFDMFLKL  3882-3921
rSRR  SLLEGNVVNGMIARQMVDMLVESSNVEMILKFFDMFLKL   4029-4068
rCRR  SMLEGNVVNGTIGKQMVDMLVESSNNVEMILKFFDMFLKL  3984-4023 hBRR  KDLTSSDTFKEYDPDGKGIISKKEFQKAMEGQKQYTQSEI  3916-3955
rBRR  KDLTSSDTFKEYDPDGKGIISKKEFQKAMEGQKQYTQSEI  3922-3961
rSRR  KDIVGSEAFQDYVTDPRGLISKKDFQKAMDSQKQFTGPEI  4069-4108
rCRR  KDLTSSDTFKEYDPDGKGIISKRDEHKAMESHKHYTQSET  4024-4063 hBRR  DFLLSCAEADENDMFNYVDEVDRFHEPAKDIGFNVAVLLT  3956-3995
rBRR  DFLLSCAEADENDMFNYIDEVDRFHEPAKDIGFNVAVLLT  3962-4001
rSRR  QFLLSCSEADENEMINEEFANRFQEPARDIGFNVAVLLT   4109-4148
rCRR  EFLLSCAETDENETLDYEEVKRFHEPAKDIGFNVAVLLT   4064-4103
```

FIGURE 1JJ

```
hBRR  NLSEHMPNDSRLKCLLDPAESVLNYFGPYLGRIEIMGGAK  3996-4035
rBRR  NLSEHMPNDSRLKCLLDPAESVLNYFEPYLGRIEIMGGAK  4002-4041
rSRR  NLSEHVPHDPRLRNFLELAESILEYFRPYLGRIEIMGASR  4149-4188
rCRR  NLSEHMPNETRLQTFLELAESVLNYFQPFLGRIEIMGSAK  4104-4143 hBRR  KIERVYFEISESSRTQWEKPQVKESKRQFIFDVVNEGGEQ  4036-4075
rBRR  KIERVYFEISESSRTQWEKPQVKESKRQFIFDVVNEGGEQ  4042-4081
rSRR  RIERIYFEISETNRAQWEMPQVKESKRQFIFDVVNEGGEA  4189-4228
rCRR  RIERVYFEISESSRTQWEKPQVKESKRQFIFDVVNEGGEK  4144-4183 hBRR  EKMGLFVNFCEDTIFEMQLASQISESDSADRPEEEDED  4076-4115
rBRR  EKMELFVNFCEDTIFEMQLASQISESDSADRPEEEGDEE  4082-4121
rSRR  EKMELFVSFCEDTIFEMQIAAQISEPEGEPEADEDEGMGE  4229-4268
rCRR  EKMELFVNFCEDTIFEMQLAAQISESDLNERSANKEESEK  4184-4223
```

FIGURE 1KK

```
hBRR  SSYVLEIAGEEEEDGSLEPASAFAMACAS-VKRNVTDFLK  4116-4154
rBRR  SSYVLEINGEEEEDKSFESASAFAMACAS-LKRNITNLLR  4122-4160
rSRR  --AAAE-GAEEGAAGAEGAAGTVAAGATARLAAAAARALR  4269-4305
rCRR  -----ERPEEQGPKMGFFSVLTVRSALFA-LRYNILTLMR  4224-4257 hBRR  RATLKNLRKQYRNVKKMTAKELVKVLFSFFWMLFVGLFQL  4155-4194
rBRR  KATLKNLRKQYRNVKKMTAKELVKVFFSFFWMLFVGLFQL  4161-4200
rSRR  GLSYRSLRRVRLRRLTAREAATALAALLWAVVARAGAA  4306-4345
rCRR  MLSLKKSLKKQMKKMTVKDMVTAFFSSYWSIFMTLLHF  4258-4297 hBRR  LFTILGGIFQILWSTVFGGGLVEGAKNIRVTKILGDMPDP  4195-4234
rBRR  FFTIVGGIFQILWSTVFGGGLVEGAKNIRVTKILGDMPDP  4201-4240
rSRR  GAGAAAGALRLLWGSLFGGGLVEGAKKVTVTELLAGMPDP  4346-4385
rCRR  VASVFRGFFRIVCSLLGGSLVEGAKKIKVAELLANMPDP  4298-4337
```

FIGURE 1LL

| | | | |
|---|---|---|---|
| hBRR | TQFGIHDDTMEAERAEVMEPGITTELVHFIKGEKGDTDIM | 4235-4274 |
| rBRR | TQFGIHDDAMEAERAEVAEAGITTELVHFVKGERGDTELM | 4241-4280 |
| rSRR | TSDEVHGEQPAGPGGDADGAGEGEGD-AAEGDGDEEVA | 4386-4424 |
| rCRR | TQDEVRGDGEEGERKPMETTLPSEDLTD-LKELTEESDLL | 4338-4476 |

| | | | |
|---|---|---|---|
| hBRR | SDLFG------------LKHGPEVGLGDLSEIIG | 4275-4304 |
| rBRR | SDLFG------------VKHGPEVGLGDLSEIIG | 4281-4310 |
| rSRR | GHEAGPGGAEGVVAVADGGP------FRPEGAGGLGDMGDTTP | 4425-4461 |
| rCRR | SDIFG------------LDLKREGGQYKLIPHNPNAGLSDL | 4477-4505 |

| | | | |
|---|---|---|---|
| hBRR | KDEPPTLESTVQKKRKAQAAAEMKA---ANEAEGKVESEKA | 4305-4341 |
| rBRR | KDEPPTLESTVRKKRKAQAAAETKA---EHEAEGKVESEKA | 4311-4347 |
| rSRR | AEPPTPEGSPILKRKLGVDGEEEELVPEPEPEPEPEPEKA | 4462-4501 |
| rCRR | MSNPVLIPEEQEKFQEQKTKEEEK---EEKEETKSEPEKA | 4506-4442 |

FIGURE 1MM

| | | | | |
|---|---|---|---|---|
| hBRR | DMEDGEKEDKDKEEEQAEYLWTEVTKKKKRRCGQKVEKPE | 4342-4381 |
| rBRR | DLEDGEKEDKAKEEERAEYLWAEVTKKKKRRRGQKVEKPE | 4348-4387 |
| rSRR | DEENGEKEEVPEAPP--------EPPKKAPPSPAKKEEAG | 4502-4534 |
| rCRR | EGEDGEKEEKVKEDK--------GKQKLRQLHTHRYGEPE | 4443-4474 |
| | | |
| hBRR | AFTANEFKGLEIYQTKLLHYLARNFYNLRFLALFVAFAIN | 4382-4421 |
| rBRR | AFMANEFKGLEIYQTKLLHYLARNFYNLRFLALFVAFAIN | 4388-4427 |
| rSRR | GAGMEFWGELEVQRVKFLNYLSRNFYTLRFLALFLAFAIN | 4535-4574 |
| rCRR | VPESAEWKKIAYQQKLLNYFARNFYNMRMLALFVAFAIN | 4475-4514 |
| | | —M1— |
| hBRR | FILLFYKVTEEPLEE----------------TEDVANLWNS | 4422-4447 |
| rBRR | FILLFYKVTEEPLEE----------------TEDVANLWNS | 4428-4453 |
| rSRR | FILLFYKVSDSPPGEDDMEGSAAGDLAGAGSGGSGWGSG | 4575-4614 |
| rCRR | FILLFYKVSTSSVVEGKELPSRS---------TSENAKVTTS | 4515-4547 |

FIGURE 1NN

| | | | | | |
|---|---|---|---|---|---|
| hBRR | FNDE---EEEEAMVFFVLQESTGYMAPTLRALAIHTIIS | 4448-4484 |
| rBRR | LNDE---EEEEAMVFFVLQESTGYMAPTLRALAVVHTIIS | 4454-4490 |
| rSRR | AGEEAEGDEDENMVYYFLEESTGYMEPALWCLSLLHTLVA | 4615-4654 |
| rCRR | LDSS---SHRIIAVHYVVLEESSGYMEPTLRILAILHTVIS | 4548-4584 |

M2

| | | |
|---|---|---|
| hBRR | LVCVVGYYCLKVPLVVFKREKEIARKLEFDGLYITEQPSE | 4485-4524 |
| rBRR | LVCVVGYYCLKVPLVVFKREKEIARKLEFDGLYITEQPSE | 4491-4530 |
| rSRR | FLCIIGYNCLKVPLVIFKREKELARKLEFDGLYITEQPGD | 4655-4694 |
| rCRR | FFCIIGYYCLKVPLVIEKREKEVARKLEFDGLYITEQPSE | 4585-4624 |

| | | |
|---|---|---|
| hBRR | DDIKGQWDPLVINTPSFPNNYWDKFVKRKVINKYGDLYGA | 4525-4564 |
| rBRR | DDIKGQWDRLVINTPSFPHNYWDKFVKRKVINKYGDLYGA | 4531-4570 |
| rSRR | DDVKGQWDRLVLNTPSFPSNYWDKFVKRKVLDKHGDIFGR | 4695-4734 |
| rCRR | DDIKGQWDRLVINTQSFPNNYWDKFVKRKVMDKYGEFYGR | 4625-4664 |

FIGURE 100

| | | |
|---|---|---|
| hBRR | ERIAELLGLDKNALDFSPVEETK--AEAASLVSWLSSIDM | 4565-4602 |
| rBRR | ERIAELLGLDKNALDFSPVEET--TAEAASLVSWLSSIDM | 4571-4608 |
| rSRR | ERIAELLGMDLASLEITAHNERK-PDPPPGLLTWLMSIDV | 4735-4773 |
| rCRR | DRISELLGMDKAALDFSDAREKKKPKKDSSLSAVLNSIDV | 4665-4704 |
| | | |
| hBRR | KYHIWKLGVVFTDNSFLYLAWYTTMSVLGHYNNFFAAHL | 4603-4642 |
| rBRR | KYHIWKLGVVFTDNSFLYLAWYTTMSVLGHYNNFFAAHL | 4609-4648 |
| rSRR | KYQIWKFGVIFTDNSFLYLGWYMVMSLLGHYNNFFAAHL | 4774-4813 |
| rCRR | KYQMWKLGVVFTDNSFLYLAWYMTMSILGHYNNFFAAHL | 4705-4744 |
| | | |
| hBRR | LDIAMGFKTLRTILSSVTHNGKQLVLTVGLLAVVVLYTV | 4643-4682 |
| rBRR | LDIAMGFKTLRTILSSVTHNGKQLVLTVGLLAVVVLYTV | 4649-4688 |
| rSRR | LDIAMGVKTLRTILSSVTHNGKQLVMTVGLLAVVVLYTV | 4814-4853 |
| rCRR | LDIAMGFKTLRTILSSVTHNGKQLVLTVGLLAVVVLYTV | 4745-4784 |

| | | | |
|---|---|---|---|
| hBRR | VAFNFFRKFYNKSEDD EPDMKCDDMMTCYL FHMYVGVRA | 4683-4722 |
| rBRR | VAFNFFRKFYNKSEDD EPDMKCDDMMTCYL FHMYVGVRA | 4689-4728 |
| rSRR | VAFNFFRKFYNKSEDE EPDMKCDDMMTCYL FHMYVGVRA | 4854-4893 |
| rCRR | VAFNFFRKFYNKSEDG DTPDMKCDDMLTCYM EHMYVGVRA | 4785-4824 |

| | | |
|---|---|---|
| hBRR | GGGIGDEIEDPAGD PYEMYRIV FDITFFFVIVILLAIIQ | 4723-4762 |
| rBRR | GGGIGDEIEDPAG DPYEMYRIV FDITFFFVIVILLAIIQ | 4729-4768 |
| rSRR | GGGIGDEIEDPAG DEYELYRVV FDITFFFVIVILLAIIQ | 4894-4933 |
| rCRR | GGGIGDEIEDPAG DEYEIYRII FDITFFFVIVILLAIIQ | 4825-4864 |

M4

| | | |
|---|---|---|
| hBRR | GLIIDAFGELRDQQEQVRE DMETKCFICGIGN DYFDTTPH | 4763-4802 |
| rBRR | GLIIDAFGELRDQQEQVRE DMETKCFICGIGN DYFDTTPH | 4769-4808 |
| rSRR | GLIIDAFGELRDQQEQVKE DMETKCFICGIGS DYFDTTPH | 4934-4973 |
| rCRR | GLIIDAFGELRDQQEQVKE DMETKCFICGIGN DYFDTVPH | 4865-4904 |

FIGURE 100

| | | | | |
|---|---|---|---|---|
| hBRR | GFETHTLQ | EHNLANYLF | FLMYLINKDETEHTGQESYVWKM | 4803-4842 |
| rBRR | GFETHTLQ | EHNLANYLF | FLMYLINKDETEHTGQESYVWKM | 4809-4848 |
| rSRR | GFETHTLE | EHNLANYMF | FLMYLINKDETEHTGQESYVWKM | 4974-5013 |
| rCRR | GFETHTLQ | EHNLANYLF | FLMYLINKDETEHTGQESYVWKM | 4905-4944 |

| | | | |
|---|---|---|---|
| hBRR | YQERCWD | FFPAGDCFRKQYEDQLG | 4843-4866 |
| rBRR | YQERCWD | FFPAGDCFRKQYEDQLG | 4849-4872 |
| rSRR | YQERCWD | FFPAGDCFRKQYEDQLS | 5014-5037 |
| rCRR | YQERCWE | FFPAGDCFRKQYEDQLN | 4945-4968 |

Fig. 2
A
 Rabbit RyR2
 Chimeric RyR
 Human RyR3
B
a 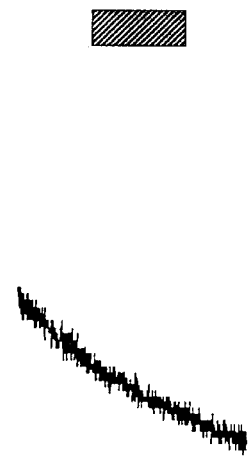
b 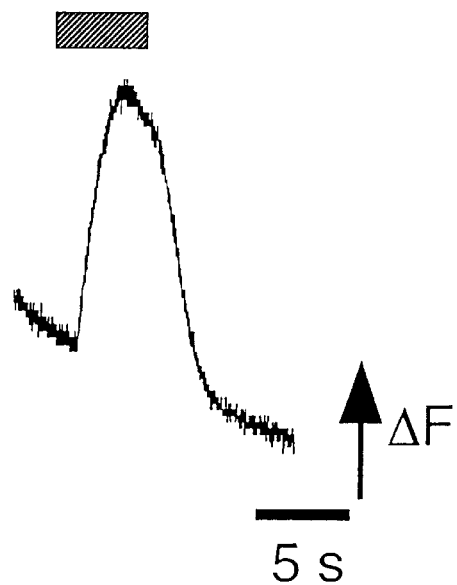

Fig. 7a

```
MAEGGEGGED EIQFLRTEDE VVLQCIATIH KEQRKFCLAA EGLGNRLCFL  50
EPTSEAKYIP PDLCVCNFVL EQSLSVRALQ EMLANTGENG GEGAAQGGGH  100
RTLLYGHAVL LRHSFSGMYL TCLTTSRSQT DKLAFDVGLR EHATGEACWW  150
TIHPASKQRS EGEKVRIGDD LILVSVSSER YLHLSVSNGN IQVDASFMQT  200
LWNVHPTCSG SSIEEGYLLG GHVVRLFHGH DECLTIPSTD QNDSQHRRIF  250
YEAGGAGTRA RSLWRVEPLR ISWSGSNIRW GQAFRLRHLT TGHYLALTED  300
QGLILQDRAK SDTKSTAFSF RASKELKEKL DSSHKRDIEG MGVPEIKYGD  350
SVCFVQHIAS GLWVTYKAQD AKTSRLGPLK RKVILHQEGH MDDGLTLQRC  400
QREESQAARI IRNTTALFSQ FVSGNNRTAA PITLPIEEVL QTLQDLIAYF  450
QPPEEEMRHE DKQNKLRSLK NRQNLFKEEG MLALVLNCID RLNVYNSVAH  500
FAGIAREESG MAWKEILNLL YKLLAALIRG NRNNCAQFSN NLDWLISKLD  550
RLESSSGILE VLHCILTESP EALNLIAEGH IKSIISLLDK HGRNHKVLDI  600
LCSLCLCNGV AVRANQNLIC DNLLPRRNLL LQTRLINDVT SIRPNIFLGV  650
AEGSAQYKKW YFELIIDQVD PFLTAEPTHL RVGWASSSGY APYPGGGEGW  700
GGNGVGDDLY SYGFDGLHLW SGRIPRAVAS INQHLLRSDD VGKLLPGPRG  750
CPASHSASMG SPCRGCLENF NTDGLFFPVM SFSAGVKVRF LMGGRHGEFK  800
FLPPSGYAPC YEALLPKEKM RLEPVKEYKR DADGIRDLLG TTQFLSQASF  850
IPCPVDTSQV ILPPHLEKIR DRLAENIHEL WGMNKIELGW TFGKIRDDNK  900
RQHPCLVEFS KLPETEKNYN LQMSTETLKT LLTLGCHIAH VNPAAEEDLK  950
KVKLPKNYMM SNGYKPAPLD LSDVKLLPPQ EILVDKLAEN AHNVWAKDRI 1000
KQGWTYGIQQ DLKNKRNPRL VPYALLDERT KKSNRDSLRE AVRTFVGYGY 1050
NIEPSDQELA DSAVEKVSID KIRFFRVERS YPVRSGKWYF EFEVVTGGDM 1100
RVGWARPGCR PDVELGADDQ AFVFEGNRGQ RWHQGSGYFG RTWQPGDVVG 1150
CMINLDDASM IFTLNGELLI TNKGSELAFA DYEIENGFVP ICCLGLSQIG 1200
RMNLGTDAST FKFYTMCGLQ EGFEPFAVNM NRDVAMWFSK RLPTFVNVPK 1250
DHPHIEVMRI DGTMDSPPCL KVTHKTFGTQ NSNADMIYCR LSMPVECHSS 1300
FSHSPCLDSE AFQKRKQMQE ILSHTTTQCY YAIRIFGGQD PSCVWVGWVT 1350
PDYHLYSEKF DLNKNCTVTV TLGDERGRVH ESVKRSNCYM VWGGDIVASS 1400
QRSNRSNVDL EIGCLVDLAM GMLSFSANGK ELGTCYQVEP NTKVFPAVFL 1450
QPTSTSLFQF ELGKLKNAMP LSAAIFRSEE ENPVPQCPPR LDVQTIQPVL 1500
WSRMPNSFLK VETERVSERH GWVVQCLEPL QMMALHIPEE NRCVDILELC 1550
EQEDLMRFHY HTLRLYSAVC ALGNSRVAYA LCSHVDLSQL FYAIDNKYLP 1600
GLLRSGFYDL LISIHLASAK ERKLMMKNEY IIPITSTTRN ICLFPDESKR 1650
HGLPGVGLRT CLKPGFRFST PCFVVTGEDH QKQSPEIPLE SLRTKALSML 1700
TEAVQCSGAH IRDPVGGSVE FQFVPVLKLI GTLLVMGVFD DDDVRQILLL 1750
IDPSVFGEHS AGTEEGAEKE EVTQVEEKAV EAGEKAGKEA PVKGLLQTRL 1800
```

Fig. 7b

```
PESVKLQMCE LLSYLCDCEL QHRVEAIVAF GDIYVSKLQA NQKFRYNELM 1850
QALNMSAALT ARKTKEFRSP PQEQINMLLN FQLGENCPCP EEIREELYDF 1900
HEDLLLHCGV PLEEEEEEEE DTSWTGKLCA LVYKIKGPPK PEKEQPTEEE 1950
ERCPTTLKEL ISQTMICWAQ EDQIQDSELV RMMFNLLRRQ YDSIGELLQA 2000
LRKTYTISHT SVSDTINLLA ALGQIRSLLS VRMGKEEELL MINGLGDIMN 2050
NKVFYQHPNL MRVLGMHETV MEVMVNVLGT EKSQIAFPKM VASCCRFLCY 2100
FCRISRQNQK AMFEHLSYLL ENSSVGLASP SMRGSTPLDV AASSVMDNNE 2150
LALSLEEPDL EKVVTYLAGC GLQSCPMLLA KGYPDVGWNP IEGERYLSFL 2200
RFAVFVNSES VEENASVVVK LLIRRPECFG PALRGEGGNG LLAAMQGAIK 2250
ISENPALDLP SQGYKREVST EDDEEEEIV HMGNAIMSFY SALIDLLGRC 2300
APEMHLIQTG KGEAIRIRSI LRSLVPTEDL VGIISIPLKL PSLNKDGSVS 2350
EPDMAGNFCP DHKAPMVLFL DRVYGIKDQT FLLHLLEVGF LPDLRASASL 2400
DTVSLSTTEA ALALNRYICS AVLPLLTRCA PLFGGTEHCT SLIDSTLQTI 2450
YRLSKGRSLT KAQRDTIEEC LLAICNHLRP SMLQQLLRRL VFDVPQLNEY 2500
CKMPLKLLTN HYEQCWKYYC LPSGWGSYGL AVEEELHLTE KLFWGIIDSL 2550
SHKKYDPDLF RMALPCLSAI AGALPPDYLD SRITATLEKQ ISVDADGNFD 2600
PKPINTMNFS LPEKLEYIVT KYAEHSHDKW ACDKSQSGWK YGISLDENVK 2650
THPLIRPFKT LTEKEKEIYR WPARESLKTM LAVGWTVERT KEGEALVQQR 2700
ENEKLRSVSQ ANQGNSYSPA PLDLSNVVLS RELQGMVEVV AENYHNIWAK 2750
KKKLELESKG GGSHPLLVPY DTLTAKEKFK DREKAQDLFK FLQVNGIIVS 2800
RGMKDMELDA SSMEKRFGYK FLKKILKYVD SAQEFIAHLE AIVSSGKTEK 2850
SPRDQEIKFF AKVLLPLVDQ YFTSHCLYFL SSPLKPLSSS GYASHKEKEM 2900
VAGLFCKLAA LVRHRISLFG SDSTTMVSCL HILAQTLDTR TVMKSGSELV 2950
KAGLRAFFEN AAEDLEKTSE NLKLGKFTHS RTQIKGVSQN INYTTVALLP 3000
ILTSIFEHVT QHQFGMDLLL GDVQISCYHI LCSLYSLGTG KNIYVERQRP 3050
ALGECLASLA AAIPVAFLEP TLNRYNPLSV FNTKTPRERS ILGMPDTVED 3100
MCPDIPQLEG LMKEINDLAE SGARYTEMPH VIEVILPMLC NYLSYWWERG 3150
PENLPPSTGP CCTKVTSEHL SLILGNILKI INNNLGIDEA SWMKRIAVYA 3200
QPIISKARPD LLRSHFIPTL EKLKKKAVKT VQEEEQLKAD GKGDTQEAEL 3250
LILDEFAVLC RDLYAFYPML IRYVDNNRSN WLKSPDADSD QLFRMVAEVF 3300
ILWCKSHNFK REEQNFVIQN EINNLAFLTG DSKSKMSKSG GQDQERKKTK 3350
RRGDLYSIQT SLIVAALKKM LPIGLNMCTP GDQELISLAK SRYSHRDTDE 3400
EVREHLRNNL HLQEKSDDPA VKWQLNLYKD VLKSEEPFNP EKTVERVQRI 3450
SAAVFHLEQV EQPLRSKKAV WHKLLSKQRK RAVVACFRMA PLYNLPRHRS 3500
INLFLHGYQR FWIETEEYSF EEKLVQDLAK SPKVEEEEEE ETEKQPDPLH 3550
QIILYFSRNA LTERSKLEDD PLYTSYSSMM AKSCQSGEDE EEDEDKEKTF 3600
```

Fig. 7c

```
EEKEMEKQKT LYQQARLHER GAAEMVLQMI SASKGEMSPM VVETLKLGIA 3650
ILNGGNAGVQ QKMLDYLKEK KDAGFFQSLP GLMQSCSVLD LNASERQNKA 3700
EGLGMVTEEG TLIVRERGEK VLQNDEFTRD LFRFLQLLCE GHNSDFQNFL 3750
RTQMGNTTTV NVIISTVDYL LRLQESISDF YWYYSGKDII DESGQHNFSK 3800
ALAVTKQIFN SLTEYIQGPC IGNQQSLAHS RLWDAVVGFL HVFANMQMKL 3850
SQDSSQIELL KELLDLLQDM VVMLLSLLEG NVVNGTIGKQ MVDTLVESST 3900
NVEMILKFFD MFLKLKDLTS SDTFKEYDPD GKGIISKKEF QKAMEGQKQY 3950
TQSEIDFLLS CAEADENDMF NYVDFVDRFH EPAKDIGFNV AVLLTNLSEH 4000
MPNDSRLKCL LDPAESVLNY FGPYLGRIEI MGGAKKIERV YFEISESSRT 4050
QWEKPQVKES KRQFIFDVVN EGGEQEKMGL FVNFCEDTIF EMQLASQISE 4100
SDSADRPEEE EEDEDSSYVL EIAGEEEEDG SLEPASAFAM ACASVKRNVT 4150
DFLKRATLKN LRKQYRNVKK MTAKELVKVL FSFFWMLFVG LFQLLFTILG 4200
GIFQILWSTV FGGGLVEGAK NIRVTKILGD MPDPTQFGIH DDTMEAERAE 4250
VMEPGITTEL VHFIKGEKGD TDIMSDLFGL HPKKEGSLKH GPEVGLGDLS 4300
EIIGKDEPPT LESTVQKKRK AQAAEMKAAN EAEGKVESEK ADMEDGEKED 4350
KDKEEEQAEY LWTEVTKKKK RRCGQKVEKP EAFTANFFKG LEIYQTKLLH 4400
YLARNFYNLR FLALFVAFAI NFILLFYKVT EEPLEEETED VANLWNSFND 4450
EEEEEAMVFF VLQESTGYMA PTLRALAIIH TIISLVCVVG YYCLKVPLVV 4500
FKREKEIARK LEFDGLYITE QPSEDDIKGQ WDPLVINTPS FPNNYWDKFV 4550
KRKVINKYGD LYGAERIAEL LGLDKNALDF SPVEETKAEA ASLVSWLSSL 4600
DMKYHIWKLG VVFTDNSFLY LAWYTTMSVL GHYNNFFFAA HLLDIAMGFK 4650
TLRTILSSVT HNGKQLVLTV GLLAVVVYLY TVVAFNFFRK FYNKSEDDDE 4700
PDMKCDDMMT CYLFHMYVGV RAGGGIGDEI EDPAGDPYEM YRIVFDITFF 4750
FFVIVILLAI IQGLIIDAFG ELRDQQEQVR EDMETKCFIC GIGNDYFDTT 4800
PHGFETHTLQ EHNLANYLFF LMYLINKDET EHTGQESYVW KMYQERCWDF 4850
FPAGDCFRKQ YEDQLG                                    4866
```

Fig. 8a

| | | | | |
|---|---|---|---|---|
|GGGCAGCAGC|AGTCAGCGCA|CGCCGAGCGG|CTGCCGGGGG|AAGCAGAGGC|50
|GCCGGAGGCT|GGGGCACCGC|CGACGCCTCG|GGAGCCATGG|CCGAAGGGGG|100
|AGAAGGAGGC|GAGGACGAGA|TCCAGTTTCT|GAGGACTGAG|GATGAAGTGG|150
|TACTCCAGTG|CATCGCCACC|ATTCATAAGG|AGCAGAGGAA|GTTCTGCCTG|200
|GCAGCCGAGG|GACTTGGGAA|TCGCCTGTGC|TTCTTGGAAC|CCACTTCAGA|250
|AGCCAAGTAC|ATTCCTCCAG|ATCTCTGCGT|CTGCAATTTT|GTGCTGGAAC|300
|AGTCCCTATC|TGTCAGAGCC|CTGCAGGAAA|TGCTTGCCAA|CACAGGTGAA|350
|AATGGCGGCG|AAGGGGCAGC|ACAAGGAGGT|GGCCACAGGA|CCCTGTTATA|400
|CGGCCATGCA|GTTCTCCTGA|GGCACTCTTT|CAGCGGAATG|TATCTAACAT|450
|GCTTGACTAC|ATCAAGATCC|CAGACAGACA|AACTTGCCTT|TGATGTAGGT|500
|CTACGGGAAC|ATGCCACAGG|AGAAGCCTGT|TGGTGGACTA|TACATCCTGC|550
|TTCCAAACAG|AGGTCCGAAG|GAGAGAAAGT|TCGAATTGGC|GATGACCTCA|600
|TCCTCGTCAG|CGTGTCCTCT|GAAAGATACC|TTCATCTCTC|AGTATCAAAT|650
|GGTAACATAC|AAGTGGATGC|CTCCTTTATG|CAAACACTCT|GGAATGTACA|700
|TCCTACGTGC|TCAGGAAGTA|GCATCGAAGA|AGGATACCTA|CTTGGTGGGC|750
|ATGTAGTACG|TCTTTTCCAT|GGTCATGATG|AATGTTTGAC|GATACCATCT|800
|ACAGACCAGA|ATGATTCCCA|GCACAGGAGG|ATATTCTACG|AAGCTGGGGG|850
|AGCTGGGACT|CGAGCCAGGT|CTCTTTGGAG|AGTGGAACCC|CTTCGGATAA|900
|GCTGGAGTGG|CAGTAACATC|AGATGGGCC|AGGCTTTCCG|ACTCCGGCAT|950
|CTCACCACAG|GCCACTACCT|GGCCTTGACA|GAAGACCAAG|GCCTTATACT|1000
|GCAAGACCGG|GCAAAGTCAG|ACACCAAGTC|CACAGCTTTC|TCTTTCCGGG|1050
|CATCAAAGGA|ACTCAAGGAG|AAATTAGACT|CCAGTCACAA|GCGAGACATA|1100
|GAAGGCATGG|GAGTTCCAGA|AATCAAGTAT|GGAGATTCTG|TCTGCTTTGT|1150
|GCAGCATATA|GCCAGTGGTC|TGTGGGTGAC|CTACAAAGCA|CAAGACGCCA|1200
|AAACTTCCCG|CCTGGGACCT|CTAAAAGAA|AGGTCATACT|CCATCAGGAA|1250
|GGCCACATGG|ATGATGGATT|AACACTGCAG|AGATGCCAAC|GTGAGGAGTC|1300
|CCAGGCTGCT|CGGATCATCC|GGAACACTAC|AGCCTTATTC|AGCCAGTTTG|1350
|TCAGTGGAAA|CAATCGCACA|GCTGCCCCCA|TCACCCTGCC|TATAGAAGAA|1400
|GTCCTGCAGA|CCCTACAGGA|CTTGATCGCC|TACTTCCAGC|CCCCAGAGGA|1450
|GGAGATGCGA|CATGAAGACA|AGCAGAACAA|GCTCCGCTCA|CTCAAAAACA|1500
|GACAAAATCT|TTTCAAGGAA|GAGGGAATGT|TGGCCCTTGT|CTTAAATTGC|1550
|ATTGACCGCT|TAAATGTCTA|CAATAGCGTA|GCACACTTTG|CAGGGATTGC|1600
|AAGGGAAGAG|AGTGGCATGG|CCTGGAAAGA|AATTCTGAAC|CTCCTCTACA|1650
|AATTGCTGGC|TGCTCTCATT|CGCGGAAACA|GAAACAATTG|CGCTCAATTC|1700
|TCCAATAACC|TTGATTGGCT|CATCAGTAAA|TTGGACAGAC|TAGAATCTTC|1750
|CTCAGGTATC|TTGGAAGTTT|TGCACTGCAT|CTTAACTGAA|AGCCCAGAAG|1800

Fig. 8b

```
CCTTAAATCT GATAGCGGAG GGCCACATCA AGTCGATCAT CTCCCTGTTG 1850
GATAAGCACG GGCGGAATCA CAAGGTTCTG GATATCCTGT GCTCCCTCTG 1900
TCTCTGCAAT GGGGTTGCAG TGAGAGCCAA CCAGAATCTG ATCTGTGACA 1950
ACTTGCTGCC CCGGAGAAAC CTACTCCTGC AGACACGACT GATTAACGAT 2000
GTAACCAGTA TCCGGCCAAA CATCTTCCTG GGAGTCGCGG AGGGCTCAGC 2050
CCAGTACAAG AAGTGGTACT TCGAGCTGAT TATCGACCAG GTGGACCCCT 2100
TCCTAACAGC AGAGCCCACA CATCTGCGGG TGGGCTGGGC CTCTTCTTCA 2150
GGCTATGCCC CATACCCAGG AGGTGGAGAA GGATGGGGAG GCAATGGTGT 2200
TGGTGACGAC CTGTACTCCT ATGGCTTTGA TGGACTTCAC CTTTGGTCAG 2250
GCCGGATACC CAGAGCTGTG GCTTCCATCA ACCAGCACCT CCTGAGATCG 2300
GATGACGTGG GTAAGCTGCT GCCTGGACCT CGGGGGTGCC CAGCATCTCA 2350
TTCCGCATCA ATGGGCAGCC CGTGCAGGGG ATGTTTGGAG AACTTCAACA 2400
CAGACGGGCT CTTCTTCCCT GTGATGAGCT TTCAGCAGG TGTCAAAGTA 2450
CGTTTCCTGA TGGGTGGACG TCATGGAGAG TTTAAGTTCC TGCCTCCCTC 2500
TGGCTATGCC CCTTGCTATG AAGCCTTACT TCCAAAAGAG AAGATGAGAT 2550
TGGAGCCTGT CAAAGAATAT AAACGTGATG CTGATGGCAT TAGAGATCTC 2600
TTGGGTACCA CCCAGTTCCT CTCCCAAGCC TCTTTCATCC CATGCCCCGT 2650
AGACACCAGT CAGGTTATTT TGCCACCTCA CCTAGAAAAG ATCCGAGACA 2700
GACTAGCTGA AAACATCCAT GAGCTTTGGG GAATGAATAA AATAGAACTT 2750
GGCTGGACTT TCGGCAAGAT ACGAGATGAC AATAAAAGAC AACACCCTTG 2800
CCTTGTGGAG TTTTCAAAGC TCCCAGAAAC TGAGAAGAAC TATAACCTGC 2850
AAATGTCAAC TGAAACCTTA AAAACCCTCT TGACCCTGGG TTGCCACATT 2900
GCTCATGTTA ACCCAGCTGC TGAGGAGGAT CTCAAGAAGG TCAAACTGCC 2950
CAAAAACTAT ATGATGTCCA ACGGCTATAA GCCAGCCCCT TTGGATTTGT 3000
CTGATGTGAA GCTGTTACCT CCTCAAGAAA TTTTAGTGGA TAAGCTTGCA 3050
GAAAATGCAC ACAATGTTTG GGCAAAAGAC AGAATAAAAC AAGGATGGAC 3100
CTATGGCATC CAACAGGATT TGAAGAACAA AAGAAATCCC CGTCTGGTGC 3150
CATATGCATT ACTGGATGAG CGTACCAAGA AGTCAAACAG GACAGCCTG 3200
CGGGAAGCTG TGCGCACTTT TGTTGGTTAC GGGTATAACA TTGAGCCATC 3250
AGACCAAGAA CTAGCTGACT CGGCTGTGGA GAAGGTCAGC ATAGACAAGA 3300
TCCGATTTTT CCGGGTAGAG CGATCTTATC CAGTGAGATC TGGAAAGTGG 3350
TATTTTGAGT TGAAGTGGT GACTGGAGGA GACATGCGAG TCGGCTGGGC 3400
GAGGCCAGGC TGTCGACCTG ATGTCGAGCT GGGGGCCGAT GACCAAGCCT 3450
TTGTGTTTGA AGGCAACAGG GGCCAGCGTT GGCATCAAGG AAGTGGGTAT 3500
TTTGGGCGTA CCTGGCAGCC AGGGGATGTG GTCGGATGTA TGATTAACCT 3550
GGATGATGCT TCAATGATCT TCACACTGAA TGGGGAGCTG CTGATCACCA 3600
```

Fig. 8c

```
ACAAAGGCTC TGAACTTGCC TTCGCTGACT ACGAGATTGA GAATGGCTTC 3650
GTGCCCATCT GCTGTCTGGG TCTATCTCAG ATCGGCCGCA TGAATCTCGG 3700
GACAGATGCC AGTACCTTCA AGTTTTATAC CATGTGCGGT CTCCAAGAGG 3750
GCTTTGAGCC TTTTGCTGTC AACATGAACA GAGATGTTGC TATGTGGTTC 3800
AGCAAGCGCC TCCCGACGTT TGTCAACGTG CCAAAGGATC ATCCACACAT 3850
AGAGGTCATG AGGATTGATG GCACCATGGA CAGCCCTCCG TGTCTCAAGG 3900
TGACGCATAA GACATTTGGC ACACAGAATA GCAATGCCGA CATGATCTAT 3950
TGCCGCTTGA GCATGCCTGT CGAGTGCCAC TCCTCCTTCA GTCACAGCCC 4000
CTGTCTGGAC AGTGAAGCTT TCCAGAAAAG GAAACAGATG CAAGAAATAC 4050
TCTCTCATAC AACAACACAG TGCTACTACG CCATCCGCAT CTTTGGTGGA 4100
CAGGATCCAT CCTGTGTCTG GTCGGATGG GTGACTCCAG ACTATCACTT 4150
GTACAGTGAA AAGTTTGACC TGAATAAAAA CTGCACAGTG ACTGTCACCC 4200
TAGGGGATGA AAGAGGCCGG GTCCATGAAA GTGTGAAACG CAGCAACTGC 4250
TACATGGTCT GGGGTGGAGA CATTGTAGCC AGTTCCCAGA GATCAAATCG 4300
GAGCAACGTG GACCTGGAGA TCGGCTGTCT CGTGGATCTG GCCATGGGCA 4350
TGTTGTCCTT CTCAGCCAAT GGAAAGGAAC TGGGCACCTG CTACCAGGTG 4400
GAGCCTAATA CCAAAGTGTT TCCAGCAGTC TTCCTGCAGC CTACAAGTAC 4450
TTCTTTGTTT CAGTTTGAAC TTGGAAAGCT GAAGAACGCA ATGCCCTGT 4500
CAGCGGCCAT ATTCAGGAGT GAAGAGGAGA ACCCAGTCCC ACAGTGTCCA 4550
CCTCGGCTGG ACGTCCAAAC CATCCAGCCC GTGCTCTGGA GCCGCATGCC 4600
CAACAGCTTC CTGAAGGTGG AGACCGAGCG TGTGAGCGAG CGCCACGGCT 4650
GGGTGGTGCA GTGCCTGGAG CCCCTGCAGA TGATGGCGCT CCACATCCCC 4700
GAGGAGAACA GGTGTGTGGA TATCCTGGAG CTCTGTGAGC AGGAGGACCT 4750
GATGCGGTTC CATTACCACA CGCTGAGGCT CTACAGCGCG GTGTGCGCCC 4800
TGGGAAACAG CCGCGTGGCC TACGCCCTGT GCAGCCACGT GGACCTCTCC 4850
CAGCTCTTCT ATGCCATTGA CAACAAGTAC CTCCCCGGCC TCCTTCGATC 4900
TGGTTTCTAT GACCTGCTCA TCAGCATCCA CCTGGCCAGC GCCAAGGAGA 4950
GGAAGCTGAT GATGAAGAAC GAGTACATCA TCCCCATTAC CAGCACCACC 5000
AGGAATATCT GCCTCTTCCC GGACGAGTCC AAGAGGCATG GACTGCCTGG 5050
GGTGGGCCTG AGAACATGTC TCAAGCCCGG GTTCAGGTTC TCCACCCCTT 5100
GCTTTGTTGT GACTGGTGAG GATCACCAAA AGCAGAGCCC CGAGATTCCC 5150
TTGGAGAGTC TCAGGACGAA GGCTCTGAGT ATGCTGACAG AGGCAGTGCA 5200
GTGCAGCGGG GCCCACATCC GAGACCCTGT AGGGGGGTCT GTGGAGTTCC 5250
AGTTTGTGCC TGTGCTGAAA CTCATTGGAA CCCTGCTGGT CATGGGCGTG 5300
TTTGATGATG ATGATGTTCG GCAGATCCTC CTCCTGATTG ATCCCTCTGT 5350
GTTTGGGGAG CATAGTGCGG GGACAGAGGA GGGAGCAGAA AAGGAGGAAG 5400
```

Fig. 8d

```
TGACCCAGGT GGAGGAGAAG GCTGTGGAGG CTGGGGAGAA GGCCGGCAAG 5450
GAGGCTCCTG TCAAAGGCTT GTTGCAGACT CGATTACCCG AATCCGTCAA 5500
GCTGCAGATG TGTGAGCTCC TCAGCTATCT CTGCGACTGT GAGCTGCAGC 5550
ACCGAGTGGA GGCCATTGTG GCATTTGGTG ACATTTATGT CTCCAAGCTG 5600
CAGGCAAATC AGAAGTTCCG CTACAATGAG CTCATGCAGG CCCTGAACAT 5650
GTCTGCGGCC CTGACTGCCC GGAAGACCAA GGAGTTCCGC TCACCCCCAC 5700
AGGAGCAGAT CAACATGCTG CTTAACTTTC AACTGGGAGA GAACTGCCCC 5750
TGCCCAGAGG AGATTCGGGA GGAGCTGTAT GATTTCCATG AGGACCTTCT 5800
CCTTCACTGT GGGGTTCCTT TGGAAGAAGA GGAAGAGGAG GAGGAGGACA 5850
CCTCCTGGAC AGGAAAACTC TGTGCCTTGG TTTACAAAAT CAAAGGCCCA 5900
CCCAAGCCAG AGAAGGAGCA GCCGACGGAG GAGGAGGAGA GATGCCCCAC 5950
AACATTGAAG GAACTCATCT CACAGACGAT GATCTGCTGG GCCCAGGAGG 6000
ACCAGATCCA GGATTCAGAG CTGGTCCGAA TGATGTTCAA CCTCCTCCGG 6050
AGGCAGTATG ACAGCATTGG GGAGCTGCTG CAGGCGCTGC GGAAGACCTA 6100
CACCATCAGC CACACCTCTG TAAGCGACAC CATCAACCTG CTGGCTGCCC 6150
TGGGCCAAAT CCGCTCCCTC CTCAGTGTCA GGATGGGCAA GGAAGAGGAG 6200
TTGCTCATGA TCAATGGGCT GGGAGACATA ATGAACAACA AGGTGTTTTA 6250
CCAGCATCCC AACCTCATGA GAGTCCTGGG CATGCACGAG ACGGTGATGG 6300
AGGTGATGGT GAACGTGTTG GGTACAGAGA AATCTCAGAT TGCATTTCCA 6350
AAGATGGTTG CTAGCTGCTG CCGTTTCCTT TGCTATTTCT GTCGAATTAG 6400
CCGGCAAAAT CAGAAGGCCA TGTTTGAGCA TCTGAGTTAT CTTCTGGAGA 6450
ATAGCAGTGT TGGCCTAGCC TCCCCGTCGA TGAGGGGATC CACCCCGCTG 6500
GATGTGGCAG CTTCCTCTGT GATGGACAAC AATGAGTTAG CGCTGAGCTT 6550
AGAGGAACCA GACCTCGAGA AGGTGGTGAC CTACTTGGCA GGCTGTGGCC 6600
TACAGAGCTG CCCCATGCTT CTGGCCAAAG GATACCCTGA TGTCGGCTGG 6650
AACCCCATTG AAGGGAACG CTACCTGTCC TTCCTGAGGT TTGCTGTCTT 6700
CGTGAACAGT GAGAGTGTGG AAGAAACGC CAGCGTTGTG GTCAAGCTGC 6750
TCATCAGACG CCCAGAGTGC TTCGGCCCGG CCCTGCGGGG TGAGGGGGGA 6800
AACGGACTCT TGGCAGCCAT GCAGGGTGCC ATTAAGATCT CTGAGAACCC 6850
AGCGCTCGAC CTCCCCTCTC AAGGATACAA AAGAGAAGTC AGCACGGAGG 6900
ACGATGAAGA GGAAGAAGAA ATCGTGCATA TGGGCAATGC AATTATGTCA 6950
TTTTATTCGG CCCTTATAGA TCTACTGGGC CGCTGTGCTC CTGAAATGCA 7000
CCTCATCCAG ACAGGAAAGG GGGAAGCCAT CCGCATCAGG TCCATCCTGC 7050
GCTCCCTGGT CCCCACAGAA GACCTGGTTG GGATCATCAG CATCCCCTTG 7100
AAACTGCCCT CCCTCAACAA AGATGGGTCG GTCAGTGAGC CAGATATGGC 7150
GGGCAATTTC TGCCCTGACC ACAAGGCACC TATGGTGCTG TTCTTGGACC 7200
```

Fig. 8e

```
GCGTTTATGG CATTAAGGAT CAAACTTTTC TGCTCCACTT GCTGGAGGTT  7250
GGATTTTTAC CTGACCTAAG AGCTTCTGCC TCTCTAGATA CAGTTTCCCT  7300
AAGCACCACA GAGGCTGCGC TTGCACTAAA TAGGTATATA TGTTCTGCTG  7350
TGCTCCCGCT CCTCACAAGA TGTGCCCCTC TCTTTGGCGG AACAGAACAC  7400
TGCACCTCTC TGATTGATTC CACACTGCAG ACAATATACA GGCTATCCAA  7450
GGGACGTTCC CTCACCAAAG CACAAGGGA CACTATAGAA GAATGTTTGC  7500
TTGCCATTTG CAATCACTTG AGGCCTTCCA TGTTACAGCA ACTCCTGCGA  7550
CGCCTCGTTT TTGATGTGCC GCAACTCAAT GAATACTGCA AAATGCCTCT  7600
CAAGCTTCTG ACGAATCACT ATGAACAGTG TTGGAAGTAT TACTGCCTGC  7650
CTTCAGGATG GGGGAGCTAC GGGCTAGCTG TGGAAGAAGA GCTGCACCTA  7700
ACGGAGAAGC TTTTCTGGGG GATTATTGAC TCGCTCTCCC ATAAGAAATA  7750
TGACCCAGAT CTTTTCCGAA TGGCCCTGCC TTGTCTCAGT GCTATAGCTG  7800
GGGCCTTGCC ACCAGATTAT TTAGATTCCA GAATCACAGC CACGTTGGAG  7850
AAACAGATCT CAGTGGATGC GGATGGCAAC TTTGACCCAA AACCTATTAA  7900
CACCATGAAT TTTTCCTTGC CTGAAAAATT GGAATACATC GTCACCAAGT  7950
ATGCTGAGCA TTCACATGAT AAATGGGCCT GTGACAAGAG TCAGAGTGGA  8000
TGGAAATATG GGATTTCCCT GGATGAAAAT GTGAAGACCC ACCCACTGAT  8050
AAGGCCTTTC AAGACATTAA CGGAGAAGGA GAAGGAAATT TATCGCTGGC  8100
CTGCGCGAGA GTCCCTGAAA ACCATGCTGG CTGTGGGCTG GACTGTGGAG  8150
AGGACCAAAG AGGGAGAAGC TTTGGTTCAA CAGCGGGAAA ATGAGAAGCT  8200
TCGAAGTGTG TCCCAGGCCA ACCAGGGCAA CAGCTACAGT CCTGCTCCCC  8250
TCGACCTCTC AAACGTTGTG CTCTCCAGAG AGCTCCAGGG AATGGTGGAG  8300
GTCGTGGCTG AGAACTATCA CAATATCTGG GCCAAGAAGA AGAAGCTGGA  8350
GCTGGAGAGC AAAGGTGGTG GCAGCCACCC TCTTCTGGTA CCATATGACA  8400
CCTTGACTGC CAAGGAAAAG TTCAAGGACC GGGAGAAGGC ACAGGACCTG  8450
TTTAAGTTCC TCCAAGTGAA TGGCATCATA GTTTCCAGGG GTATGAAGGA  8500
TATGGAGCTG GATGCCTCCT CCATGGAGAA GAGGTTTGGC TATAAGTTCT  8550
TGAAGAAGAT CCTGAAATAC GTTGATTCTG CTCAAGAATT TATTGCCCAT  8600
TTAGAAGCCA TTGTCAGCAG TGGGAAAACT GAAAAGTCTC CCCGTGACCA  8650
GGAGATCAAA TTCTTTGCCA AAGTTCTCCT CCCGCTGGTT GACCAGTACT  8700
TCACCAGTCA TTGCCTCTAC TTCTTGTCAT CCCCTCTGAA GCCCCTTAGC  8750
AGCAGCGGAT ATGCCTCCCA TAAGGAGAAA GAAATGGTGG CCGGCCTGTT  8800
CTGCAAACTT GCCGCTCTCG TTAGACACAG AATTTCCCTC TTTGGTAGTG  8850
ATTCTACTAC AATGGTGAGC TGTCTTCACA TCTTAGCTCA GACACTTGAC  8900
ACAAGGACTG TCATGAAGTC AGGCTCAGAG CTGGTGAAGG CTGGGTTACG  8950
AGCATTCTTT GAAAATGCTG CAGAAGATTT GGAGAAGACT TCAGAAAACC  9000
```

Fig. 8f

| | | | | | |
|---|---|---|---|---|---|
| TGAAACTTGG | GAAGTTCACC | CATTCCCGAA | CGCAGATTAA | AGGCGTTTCT | 9050 |
| CAGAATATTA | ACTACACTAC | AGTGGCTCTG | CTCCCCATCC | TGACGTCCAT | 9100 |
| CTTTGAGCAC | GTCACTCAGC | ATCAGTTTGG | AATGGATCTA | CTCTTGGGTG | 9150 |
| ATGTGCAGAT | TTCATGCTAC | CACATACTGT | GCAGCCTCTA | CTCCCTTGGG | 9200 |
| ACGGGAAAGA | ACATTTATGT | TGAAAGGCAA | CGCCCTGCCC | TTGGAGAATG | 9250 |
| TCTGGCCTCG | CTGGCAGCTG | CCATACCAGT | GGCATTCCTG | GAGCCCACCC | 9300 |
| TTAATCGCTA | CAATCCACTC | TCGGTCTTCA | ACACCAAAAC | CCCCAGGGAG | 9350 |
| AGGTCTATTC | TGGGGATGCC | AGACACGGTA | GAAGACATGT | GTCCTGACAT | 9400 |
| CCCCCAGCTG | GAAGGCCTGA | TGAAGGAAAT | CAACGACCTG | GCCGAGTCAG | 9450 |
| GGGCCCGGTA | CACAGAGATG | CCCCATGTCA | TCGAGGTGAT | CTTACCCATG | 9500 |
| CTCTGCAACT | ACTTGTCCTA | CTGGTGGGAG | CGGGGTCCTG | AGAACCTGCC | 9550 |
| CCCCAGCACA | GGGCCATGCT | GCACCAAGGT | CACCTCTGAA | CACCTCAGTC | 9600 |
| TCATCCTGGG | CAACATTCTG | AAAATCATCA | ACAACAACCT | GGGCATCGAT | 9650 |
| GAGGCCTCCT | GGATGAAGCG | CATTGCAGTG | TATGCACAGC | CCATCATCAG | 9700 |
| CAAAGCCAGG | CCCGACCTGC | TGAGAAGCCA | CTTCATCCCA | ACTCTGGAGA | 9750 |
| AGCTGAAGAA | AAAGGCTGTC | AAGACGGTGC | AGGAGGAGGA | GCAGTTGAAA | 9800 |
| GCCGATGGCA | AAGGGACAC | CCAGGAGGCA | GAACTCCTCA | TCCTGGACGA | 9850 |
| GTTCGCGGTC | CTCTGCAGAG | ATCTCTATGC | CTTCTACCCC | ATGCTGATCC | 9900 |
| GCTACGTGGA | CAACAACAGA | TCTAACTGGC | TGAAAAGTCC | TGATGCTGAT | 9950 |
| TCTGACCAGC | TCTTCCGCAT | GGTGGCAGAA | GTCTTCATTC | TGTGGTGTAA | 10000 |
| ATCTCATAAC | TTCAAGAGAG | AAGAGCAAAA | TTTTGTGATT | CAGAATGAAA | 10050 |
| TTAATAATTT | GGCATTTTA | ACTGGAGACA | GCAAAAGCAA | GATGTCAAAA | 10100 |
| TCTGGAGGAC | AAGACCAGGA | GCGGAAGAAG | ACAAAGCGGC | GGGGAGACTT | 10150 |
| GTATTCCATC | CAGACCTCCC | TCATCGTGGC | TGCACTCAAG | AAAATGCTGC | 10200 |
| CCATTGGTTT | GAATATGTGT | ACTCCAGGCG | ACCAGGAGCT | GATCTCCCTC | 10250 |
| GCAAAATCGC | GATACAGCCA | TAGGGACACA | GATGAAGAGG | TCAGAGAACA | 10300 |
| TCTGCGGAAC | AACTTGCACT | TGCAGGAAAA | GTCTGATGAC | CCAGCTGTAA | 10350 |
| AATGGCAACT | GAACCTCTAC | AAGGATGTTC | TGAAGAGTGA | AGAACCTTTC | 10400 |
| AATCCGGAAA | AGACAGTGGA | GCGTGTGCAG | AGAATTTCAG | CAGCTGTCTT | 10450 |
| CCACCTGGAA | CAGGTGGAAC | AGCCTTTGAG | GTCCAAGAAG | GCCGTCTGGC | 10500 |
| ACAAACTGTT | ATCAAAGCAA | CGGAAACGGG | CAGTGGTGGC | CTGTTTCAGG | 10550 |
| ATGGCCCCTC | TCTACAACCT | GCCCAGGCAC | CGCTCTATTA | ACCTCTTCCT | 10600 |
| CCATGGCTAT | CAGAGATTTT | GGATAGAAAC | AGAGGAGTAT | TCCTTTGAAG | 10650 |
| AGAAACTAGT | ACAGGATTTG | GCTAAATCTC | CAAGGTGGA | AGAGGAGGAG | 10700 |
| GAGGAAGAGA | CAGAAAAACA | ACCTGACCCA | CTACATCAGA | TCATTCTCTA | 10750 |
| TTTTAGCCGC | AACGCTCTCA | CGGAGAGGAG | CAAATTGGAA | GACGACCCTT | 10800 |

Fig. 8g

| | | | | | |
|---|---|---|---|---|---|
| TGTACACCTC | CTATTCCAGC | ATGATGGCCA | AGAGTTGTCA | AAGTGGTGAG | 10850 |
| GATGAAGAAG | AAGATGAAGA | CAAGGAAAAA | ACATTTGAAG | AGAAAGAGAT | 10900 |
| GGAGAAGCAA | AAAACCCTCT | ATCAGCAAGC | TCGGCTGCAT | GAGCGTGGTG | 10950 |
| CTGCAGAGAT | GGTCCTTCAG | ATGATAAGCG | CTAGCAAAGG | TGAGATGAGC | 11000 |
| CCCATGGTGG | TTGAGACGCT | GAAGCTGGGG | ATCGCCATTC | TGAACGGAGG | 11050 |
| CAATGCTGGT | GTGCAACAGA | AAATGCTAGA | TTACCTAAAG | GAGAAAAAGG | 11100 |
| ATGCTGGATT | CTTTCAAAGC | CTTCCTGGTC | TTATGCAGTC | TTGCAGCGTC | 11150 |
| CTTGATTTGA | ATGCATCTGA | GAGGCAGAAT | AAAGCTGAAG | GCCTGGGGAT | 11200 |
| GGTGACTGAA | GAAGGAACAC | TCATTGTTCG | GAACGTGGT | GAAAAGTAC | 11250 |
| TCCAGAATGA | CGAGTTCACG | CGTGATCTCT | TTAGATTCCT | ACAGTTACTT | 11300 |
| TGTGAGGGAC | ATAACAGTGA | CTTTCAGAAC | TTCCTGCGGA | CTCAGATGGG | 11350 |
| CAACACCACC | ACCGTGAATG | TCATCATCAG | CACTGTGGAC | TACCTTCTGC | 11400 |
| GTCTGCAGGA | ATCAATCAGT | GATTTCTACT | GGTATTATTC | AGGGAAGGAC | 11450 |
| ATCATTGATG | AATCTGGACA | GCACAATTTT | TCCAAAGCTC | TGGCAGTCAC | 11500 |
| CAAGCAGATT | TTCAATTCTC | TTACAGAATA | CATCCAGGGC | CCTTGCATTG | 11550 |
| GTAATCAACA | GAGCCTGGCT | CACAGCAGGC | TGTGGGACGC | AGTGGTTGGC | 11600 |
| TTCCTCCATG | TCTTTGCTAA | TATGCAGATG | AAACTCTCTC | AGGATTCCAG | 11650 |
| TCAGATCGAG | CTGCTGAAGG | AACTCTTGGA | TCTCCTTCAG | GACATGGTGG | 11700 |
| TGATGCTTCT | GTCCCTCCTG | GAAGGGAATG | TGGTAAATGG | CACCATTGGC | 11750 |
| AAGCAGATGG | TTGACACACT | GGTAGAATCA | TCTACCAATG | TAGAAATGAT | 11800 |
| CTTGAAATTC | TTTGACATGT | TCTTGAAACT | TAAAGACTTA | ACCAGCTCAG | 11850 |
| ACACCTTCAA | AGAATATGAC | CCAGATGGTA | AAGGAATTAT | CTCCAAAAAA | 11900 |
| GAATTCCAGA | AGGCCATGGA | AGGGCAAAAA | CAGTACACGC | AGTCAGAGAT | 11950 |
| TGACTTTCTC | CTGTCGTGTG | CAGAAGCTGA | TGAGAATGAC | ATGTTTAATT | 12000 |
| ACGTTGATTT | TGTAGACCGG | TTCCATGAGC | AGCCAAGGA | CATAGGGTTT | 12050 |
| AATGTGGCTG | TGTTATTGAC | AAATCTTTCT | GAACACATGC | CAAACGATTC | 12100 |
| CCGCCTGAAG | TGTCTGTTGG | ACCCAGCAGA | AAGTGTGCTA | AATTACTTCG | 12150 |
| GACCCTACCT | AGGACGCATC | GAGATCATGG | GTGGGGCCAA | GAAGATTGAG | 12200 |
| CGTGTTTATT | TTGAGATCAG | TGAATCCAGT | CGCACTCAGT | GGGAGAAGCC | 12250 |
| CCAGGTGAAG | GAATCTAAGC | GACAGTTCAT | TTTTGATGTT | GTCAATGAAG | 12300 |
| GTGGGGAGCA | GGAAAAGATG | GGGCTGTTTG | TGAACTTCTG | TGAGGACACC | 12350 |
| ATCTTTGAAA | TGCAGTTAGC | ATCTCAGATC | TCTGAATCCG | ATTCAGCTGA | 12400 |
| CAGGCCAGAA | GAGGAGGAAG | AAGATGAAGA | TTCTTCTTAC | GTGTTAGAAA | 12450 |
| TTGCGGGTGA | AGAGGAAGAA | GACGGGTCTC | TTGAGCCGGC | CTCTGCATTT | 12500 |
| GCTATGGCCT | GTGCCTCTGT | GAAGAGGAAT | GTCACCGACT | TCCTGAAGAG | 12550 |
| AGCAACCCTG | AAGAACCTCA | GGAAGCAGTA | CAGGAACGTG | AAAAAGATGA | 12600 |

Fig. 8h

```
CTGCGAAGGA GCTGGTGAAG GTGCTCTTCT CCTTTTTCTG GATGCTGTTC    12650
GTGGGGCTAT TCCAGTTGCT CTTCACCATC CTGGGAGGAA TCTTTCAGAT    12700
CCTCTGGAGC ACAGTGTTTG GAGGGGGCCT GGTAGAAGGG GCAAAGAACA    12750
TCAGAGTGAC CAAGATCCTG GGTGACATGC CTGACCCAAC CCAATTTGGT    12800
ATCCATGATG ACACTATGGA GGCTGAGAGG GCAGAGGTGA TGGAGCCAGG    12850
TATCACCACT GAACTAGTAC ACTTCATAAA GGGGGAGAAG GGAGATACAG    12900
ATATCATGTC AGACCTCTTT GGACTCCACC CAAAGAAAGA GGGCAGCTTA    12950
AAGCATGGGC CTGAAGTGGG TTTGGGTGAC CTCTCAGAAA TTATTGGCAA    13000
GGATGAACCC CCTACATTAG AGAGTACTGT ACAGAAGAAG AGGAAAGCTC    13050
AGGCAGCAGA AATGAAAGCA GCAAATGAAG CAGAAGGAAA AGTAGAATCC    13100
GAGAAGGCAG ACATGGAAGA TGGAGAGAAG GAAGACAAAG ACAAAGAAGA    13150
GGAGCAAGCT GAGTACCTGT GGACAGAAGT GACAAAAAAG AAGAAGCGGC    13200
GGTGTGGTCA GAAGGTTGAG AAGCCGGAAG CTTTCACAGC CAATTTCTTT    13250
AAAGGGCTGG AAATCTATCA GACCAAGTTA CTGCATTACC TGGCCAGGAA    13300
TTTCTACAAC CTGAGGTTCC TTGCTCTGTT TGTAGCCTTC GCTATCAACT    13350
TCATCCTGCT TTTTTATAAG GTCACTGAAG AACCTTTAGA AGAAGAGACA    13400
GAGGATGTTG CAAACCTATG GAATTCCTTT AATGACGAGG AAGAGGAAGA    13450
AGCGATGGTA TTCTTTGTCC TTCAGGAGAG CACCGGGTAT ATGGCACCAA    13500
CCCTGCGTGC CCTGGCCATC ATCCATACCA TCATCTCTCT AGTCTGTGTG    13550
GTGGGCTACT ACTGCCTGAA GGTGCCTTTG GTGGTTTTCA AAAGGGAAAA    13600
AGAAATCGCC AGGAAGCTGG AGTTTGATGG CCTATATATC ACCGAACAGC    13650
CATCTGAAGA TGACATCAAG GGGCAGTGGG ACCCCTTGGT GATCAACACA    13700
CCATCTTTTC CTAATAACTA CTGGGACAAG TTTGTAAAGA GAAAGGTGAT    13750
CAACAAGTAT GGAGATCTCT ACGGAGCAGA ACGCATTGCT GAACTTCTGG    13800
GTTTGGACAA AAATGCTCTT GACTTTAGCC CAGTAGAAGA GACCAAAGCA    13850
GAAGCGGCTT CTCTGGTGTC ATGGCTAAGT TCCTTAGACA TGAAGTACCA    13900
TATCTGGAAG CTTGGAGTTG TTTTTACTGA CAACTCCTTT CTCTACCTTG    13950
CCTGGTATAC AACCATGTCA GTCCTGGGCC ACTACAATAA CTTCTTCTTT    14000
GCTGCTCACC TATTGGACAT CGCAATGGGC TTCAAGACAC TGAGGACCAT    14050
TCTGTCATCT GTAACTCACA ATGGCAAACA GTTGGTTCTG ACTGTCGGTC    14100
TCCTGGCCGT GGTGGTTTAT CTCTATACTG TGGTGGCTTT CAACTTCTTC    14150
CGCAAGTTCT ACAACAAAAG CGAAGACGAT GACGAGCCCG ATATGAAGTG    14200
CGACGACATG ATGACGTGTT ACCTTTTCCA CATGTACGTG GGAGTGAGAG    14250
CAGGAGGTGG CATTGGTGAT GAAATTGAAG ACCCTGCTGG TGATCCTTAT    14300
GAAATGTATC GCATTGTCTT TGACATTACC TTTTTCTTCT TCGTCATTGT    14350
CATCTTGCTG GCCATCATTC AAGGTCTTAT TATTGATGCT TTCGGAGAGC    14400
```

Fig. 8i

| | | | | | |
|---|---|---|---|---|---|
| TAAGAGACCA | GCAGGAACAA | GTACGAGAAG | ATATGGAGAC | TAAATGTTTC | 14450 |
| ATCTGTGGGA | TTGGCAATGA | CTACTTTGAC | ACAACCCCTC | ATGGTTTTGA | 14500 |
| AACACATACA | TTACAAGAGC | ACAACTTAGC | CAACTACTTG | TTCTTTCTGA | 14550 |
| TGTATTTGAT | TAATAAAGAT | GAAACAGAGC | ACACGGGTCA | GGAATCTTAT | 14600 |
| GTCTGGAAGA | TGTACCAAGA | AAGGTGTTGG | GATTTCTTCC | CAGCCGGTGA | 14650 |
| CTGCTTTCGT | AAACAATATG | AAGATCAGCT | TGGATAAATC | TGAATCAAAG | 14700 |
| AAGCGCGACA | ATTCTGGACA | GTCAACTTCC | CATGAAATAA | AGTCCCCTTT | 14750 |
| TTACAGTTCT | GCAACATATC | TGAAATGTGA | CATTTTCTAA | ATGCCTCCCT | 14800 |
| TAAAAAAAAA | ACTGCTGAAA | ATCTGTGCTA | TTTTGAAATT | GATTTGGCTT | 14850 |
| TTTGTGCCTA | ATGGACATAC | ACTGTGGGAG | AGAACCTGTC | AAAATGTCGA | 14900 |
| AGAAGGAAGG | CGAAGAATCA | AGTAATCTCT | AGGCAAATGC | CTTCAAGTTT | 14950 |
| TCCAGTTCTG | AGGTAACTAG | TTCAGTTTGT | TGGGATGGAA | GCATGAAGGA | 15000 |
| AAGGGCTAGA | GAAGTATGAA | ATCTCGAATG | TGTAATACCT | GAAAATTTAA | 15050 |
| ACACTTGAAT | GTCATCATGG | TATCCAACTT | GTGACTCATA | GGGTCTGAAC | 15100 |
| TCCAAAAGAT | AATAACTGCA | GTCTAATTTT | TCCCATGGTA | CTTGCTAGTG | 15150 |
| ACTGTATCCA | GAAAGCTTT | AAGCAGTTAA | AGAAACAGAA | AAAAACCGAC | 15200 |
| ACTTTGTCGA | CACTGAAATA | TCGATTAAGT | GCCTTAAAAC | CTCTTTAGAC | 15250 |
| ATAGCTATGC | AAGTTTTTA | TGTTTGTGTT | CCAGAAGGAC | AGTTCCATTC | 15300 |
| ATTAGTTGTG | ATCTTCCGTC | TTACTTTATG | AAACTGCACT | TGAAGGTTAT | 15350 |
| TCATACAAGT | TTTTTTAGTA | ACAGCTGTCA | GTCAACTGCT | GTTATTAGAA | 15400 |
| GAAAAGTACT | GTACTGAAAA | TTCAAAAAAA | AATCTCAACC | TTATGCCAAA | 15450 |
| ATGGAGTAAT | GCTTTATGGT | CCCTTGTAAG | TAGTGGAGCT | GCTCTGTTTA | 15500 |
| GGTGAATCTC | CTCAAATACA | GTGAAGTGCC | CACTGCAATA | AAGTAATACG | 15550 |
| TGCCAATAAA | AAAAAAAAA | AA | | | 15572 |

SEQUENCE LISTING

```
<160> NUMBER OF SEQ ID NOS: 11

<210> SEQ ID NO 1
<211> LENGTH: 15572
<212> TYPE: DNA
<213> ORGANISM: Homo sapiens

<400> SEQUENCE: 1
gggcagcagc agtcagcgca cgccgagcgg ctgccggggg aagcagaggc gccggaggct      60
ggggcaccgc cgacgcctcg ggagccatgg ccgaaggggg agaaggaggc gaggacgaga     120
tccagtttct gaggactgag gatgaagtgg tactccagtg catcgccacc attcataagg     180
agcagaggaa gttctgcctg gcagccgagg gacttgggaa tcgcctgtgc ttcttggaac     240
ccacttcaga agccaagtac attcctccag atctctgcgt ctgcaatttt gtgctggaac     300
agtccctatc tgtcagagcc ctgcaggaaa tgcttgccaa cacaggtgaa aatggcggcg     360
```

```
aagggcagc acaaggaggt ggccacagga ccctgttata cggccatgca gttctcctga    420
ggcactcttt cagcggaatg tatctaacat gcttgactac atcaagatcc cagacagaca    480
aacttgcctt tgatgtaggt ctacgggaac atgccacagg agaagcctgt tggtggacta    540
tacatcctgc ttccaaacag aggtccgaag agagaaagt tcgaattggc gatgacctca    600
tcctcgtcag cgtgtcctct gaaagatacc ttcatctctc agtatcaaat ggtaacatac    660
aagtggatgc ctcctttatg caaacactct ggaatgtaca tcctacgtgc tcaggaagta    720
gcatcgaaga aggataccta cttggtgggc atgtagtacg tcttttccat ggtcatgatg    780
aatgtttgac gataccatct acagaccaga atgattccca gcacaggagg atattctacg    840
aagctggggg agctgggact cgagccaggt ctctttggag agtggaaccc cttcggataa    900
gctggagtgg cagtaacatc agatgggcc aggctttccg actccggcat ctcaccacag    960
gccactacct ggccttgaca gaagaccaag gccttatact gcaagaccgg gcaaagtcag   1020
acaccaagtc cacagctttc tcttccggg catcaaagga actcaaggag aaattagact   1080
ccagtcacaa gcgagacata gaaggcatgg gagttccaga aatcaagtat ggagattctg   1140
tctgctttgt gcagcatata gccagtggtc tgtgggtgac ctacaaagca caagacgcca   1200
aaacttcccg cctgggacct ctaaaaagaa aggtcatact ccatcaggaa ggccacatgg   1260
atgatggatt aacactgcag agatgccaac gtgaggagtc ccaggctgct cggatcatcc   1320
ggaacactac agcctattc agccagtttg tcagtggaaa caatcgcaca gctgccccca   1380
tcaccctgcc tatagaagaa gtcctgcaga ccctacagga cttgatcgcc tacttccagc   1440
ccccagagga ggagatgcga catgaagaca agcagaacaa gctccgctca ctcaaaaaca   1500
gacaaaatct tttcaaggaa gagggaatgt tggcccttgt cttaaattgc attgaccgct   1560
taaatgtcta caatagcgta gcacactttg cagggattgc aagggaagag agtggcatgg   1620 cctgaaaga aattctgaac ctcctctaca aattgctggc tgctctcatt cgcggaaaca   1680
gaaacaattg cgctcaattc tccaataacc ttgattggct catcagtaaa ttggacagac   1740
tagaatcttc ctcaggtatc ttggaagttt tgcactgcat cttaactgaa agcccagaag   1800
ccttaaatct gatagcggag ggccacatca agtcgatcat ctccctgttg gataagcacg   1860
ggcggaatca caaggttctg gatatcctgt gctccctctg tctctgcaat ggggttgcag   1920
tgagagccaa ccagaatctg atctgtgaca acttgctgcc ccggagaaac ctactcctgc   1980
agacacgact gattaacgat gtaaccagta tccggccaaa catcttcctg ggagtcgcgg   2040
agggctcagc ccagtacaag aagtggtact tcgagctgat tatcgaccag gtggacccct   2100
tcctaacagc agagcccaca catctgcggg tgggctgggc ctcttcttca ggctatgccc   2160
catacccagg aggtggagaa ggatggggag gcaatggtgt tggtgacgac ctgtactcct   2220
atggctttga tggacttcac ctttggtcag gccggatacc cagagctgtg gcttccatca   2280
accagcacct cctgagatcg gatgacgtgg gtaagctgct gcctggacct cggggggtgcc   2340 cagcatctca ttccgcatca atgggcagcc cgtgcagggg atgtttggag aacttcaaca   2400
cagacgggct cttcttccct gtgatgagct tttcagcagg tgtcaaagta cgtttcctga   2460
tgggtggacg tcatggagag tttaagttcc tgcctccctc tggctatgcc ccttgctatg   2520
aagccttact tccaaaagag aagatgagat tggagcctgt caaagaatat aaacgtgatg   2580
ctgatggcat tagagatctc ttgggtacca cccagttcct ctcccaagcc tctttcatcc   2640
catgccccgt agacaccagt caggttattt tgccacctca cctagaaaag atccgagaca   2700
```

-continued

```
gactagctga aaacatccat gagctttggg gaatgaataa aatagaactt ggctggactt      2760
tcggcaagat acgagatgac aataaaagac aacacccttg ccttgtggag ttttcaaagc      2820
tcccagaaac tgagaagaac tataacctgc aaatgtcaac tgaaacctta aaaaccctct      2880
tgaccctggg ttgccacatt gctcatgtta acccagctgc tgaggaggat ctcaagaagg      2940
tcaaactgcc caaaaactat atgatgtcca acggctataa gccagcccct ttggatttgt      3000
ctgatgtgaa gctgttacct cctcaagaaa ttttagtgga taagcttgca gaaaatgcac      3060
acaatgtttg ggcaaaagac agaataaaac aaggatggac ctatggcatc aacaggatt       3120 tgaagaacaa aagaaatccc cgtctggtgc catatgcatt actggatgag cgtaccaaga      3180
agtcaaacag ggacagcctg cgggaagctg tgcgcacttt tgttggttac gggtataaca      3240
ttgagccatc agaccaagaa ctagctgact cggctgtgga aaggtcagc atagacaaga       3300 tccgattttt ccgggtagag cgatcttatc cagtgagatc tggaaagtgg tattttgagt      3360
ttgaagtggt gactggagga gacatgcgag tcggctgggc gaggccaggc tgtcgacctg      3420
atgtcgagct gggggccgat gaccaagcct tgtgtttga aggcaacagg ggccagcgtt       3480
ggcatcaagg aagtgggtat tttggcgta cctggcagcc aggggatgtg gtcggatgta      3540
tgattaacct ggatgatgct tcaatgatct tcacactgaa tggggagctg ctgatcacca      3600 acaaggctc tgaacttgcc ttcgctgact acgagattga gaatggcttc gtgcccatct       3660
gctgtctggg tctatctcag atcggccgca tgaatctcgg gacagatgcc agtaccttca      3720
agttttatac catgtgcggt ctccaagagg ctttgagcc ttttgctgtc aacatgaaca       3780
gagatgttgc tatgtggttc agcaagcgcc tcccgacgtt tgtcaacgtg ccaaaggatc      3840
atccacacat agaggtcatg aggattgatg gcaccatgga cagccctccg tgtctcaagg      3900
tgacgcataa gacatttggc acacagaata gcaatgccga catgatctat tgccgcttga      3960
gcatgcctgt cgagtccac tcctccttca gtcacagccc ctgtctgac agtgaagctt        4020 tccagaaaag gaaacagatg caagaaatac tctctcatac aacaacacag tgctactacg      4080
ccatccgcat ctttggtgga caggatccat cctgtgtctg ggtcggatgg ggtgactccag     4140 actatcactt gtacagtgaa aagtttgacc tgaataaaaa ctgcacagtg actgtcaccc      4200 tagggggatga agaggccgg gtccatgaaa gtgtgaaacg cagcaactgc tacatggtct      4260
ggggtggaga cattgtagcc agttcccaga gatcaaatcg gagcaacgtg gacctggaga     4320
tcggctgtct cgtggatctg gccatgggca tgttgtcctt ctcagccaat ggaaaggaac      4380
tgggcacctg ctaccaggtg gagcctaata ccaaagtgtt tccagcagtc ttcctgcagc      4440
ctacaagtac ttctttgttt cagtttgaac ttggaaagct gaagaacgca atgcccctgt      4500
cagcggccat attcaggagt gaagaggaga acccagtccc acagtgtcca cctcggctgg     4560
acgtccaaac catccagccc gtgctctgga ccgcatgcc caacagcttc ctgaaggtgg      4620
agaccgagcg tgtgagcgag cgccacggct gggtggtgca gtgcctggag ccctgcaga      4680 tgatggcgct ccacatcccc gaggagaaca ggtgtgtgga tatcctggag ctctgtgagc      4740
aggaggacct gatgcggttc cattaccaca cgctgaggct ctacagcgcg tgtgcgccc       4800 tgggaaacag ccgcgtggcc tacgccctgt gcagccacgt ggacctctcc cagctcttct      4860
atgccattga caacagtac ctccccggcc tccttcgatc tggtttctat gacctgctca       4920
tcagcatcca cctggccagc gccaaggaga ggaagctgat gatgaagaac gagtacatca     4980
tccccattac cagcaccacc aggaatatct gcctcttccc ggacgagtcc aagaggcatg      5040
gactgcctgg ggtgggcctg agaacatgtc tcaagcccgg gttcaggttc tccacccctt      5100
```

-continued

```
gctttgttgt gactggtgag gatcaccaaa agcagagccc cgagattccc ttggagagtc   5160
tcaggacgaa ggctctgagt atgctgacag aggcagtgca gtgcagcggg gcccacatcc   5220
gagaccctgt aggggggtct gtggagttcc agtttgtgcc tgtgctgaaa ctcattggaa   5280
ccctgctggt catgggcgtg tttgatgatg atgatgttcg gcagatcctc ctcctgattg   5340
atccctctgt gtttggggag catagtgcgg ggacagagga gggagcagaa aaggaggaag   5400
tgacccaggt ggaggagaag gctgtggagg ctggggagaa ggccggcaag gaggctcctg   5460
tcaaaggctt gttgcagact cgattacccg aatccgtcaa gctgcagatg tgtgagctcc   5520
tcagctatct ctgcgactgt gagctgcagc accgagtgga ggccattgtg catttggtg    5580 acatttatgt ctccaagctg caggcaaatc agaagttccg ctacaatgag ctcatgcagg   5640
ccctgaacat gtctgcggcc ctgactgccc ggaagaccaa ggagttccgc tcaccccac    5700 aggagcagat caacatgctg cttaactttc aactgggaga gaactgcccc tgcccagagg   5760
agattcggga ggagctgtat gatttccatg aggaccttct ccttcactgt ggggttcctt   5820
tggaagaaga ggaagaggag gaggaggaca cctcctggac aggaaaactc tgtgccttgg   5880
tttacaaaat caaaggccca cccaagccag agaaggagca gccgacggag gaggaggaga   5940
gatgccccac aacattgaag gaactcatct cacagacgat gatctgctgg gcccaggagg   6000
accagatcca ggattcagag ctggtccgaa tgatgttcaa cctcctccgg aggcagtatg   6060
acagcattgg ggagctgctg caggcgctgc ggaagaccta caccatcagc cacacctctg   6120
taagcgacac catcaacctg ctggctgccc tgggccaaat ccgctccctc ctcagtgtca   6180
ggatgggcaa ggaagaggag ttgctcatga tcaatgggct gggagacata atgaacaaca   6240 aggtgttta ccagcatccc aacctcatga gagtcctggg catgcacgag acggtgatgg    6300
aggtgatggt gaacgtgttg ggtacagaga aatctcagat tgcatttcca aagatggttg   6360
ctagctgctg ccgtttcctt tgctatttct gtcgaattag ccggcaaaat cagaaggcca   6420
tgtttgagca tctgagttat cttctggaga atagcagtgt tggcctagcc tccccgtcga   6480 tgagggatc caccccgctg gatgtggcag cttcctctgt gatggacaac aatgagttag    6540
cgctgagctt agaggaacca gacctcgaga aggtggtgac ctacttggca ggctgtggcc   6600
tacagagctg ccccatgctt ctggccaaag ataccctga tgtcggctgg aaccccattg    6660
aaggggaacg ctacctgtcc ttcctgaggt ttgctgtctt cgtgaacagt gagagtgtgg   6720
aagaaaacgc cagcgttgtg gtcaagctgc tcatcagacg cccagagtgc ttcggcccgg   6780
ccctgcgggg tgagggggga acggactct tggcagccat gcaggtgcc attaagatct     6840 ctgagaaccc agcgctcgac ctcccctctc aaggatacaa aagagaagtc agcacggagg   6900
acgatgaaga ggaagaagaa atcgtgcata tgggcaatgc aattatgtca ttttattcgg   6960
cccttataga tctactgggc cgctgtgctc ctgaaatgca cctcatccag acaggaaagg   7020
gggaagccat ccgcatcagg tccatcctgc gctccctggt ccccacagaa gacctggttg   7080
ggatcatcag catcccttg aaactgccct ccctcaacaa agatgggtcg gtcagtgagc    7140
cagatatggc gggcaatttc tgccctgacc acaaggcacc tatggtgctg ttcttggacc   7200
gcgtttatgg cattaaggat caaactttc tgctccactt gctggaggtt ggattttac     7260 ctgacctaag agcttctgcc tctctagata cagtttccct aagcaccaca gaggctgcgc   7320
ttgcactaaa taggtatata tgttctgctg tgctcccgct cctcacaaga tgtgcccctc   7380
tctttggcgg aacagaacac tgcacctctc tgattgattc cacactgcag acaatataca   7440
```

```
ggctatccaa gggacgttcc ctcaccaaag cacaaaggga cactatagaa gaatgtttgc    7500
ttgccatttg caatcacttg aggccttcca tgttacagca actcctgcga cgcctcgttt    7560
ttgatgtgcc gcaactcaat gaatactgca aaatgcctct caagcttctg acgaatcact    7620
atgaacagtg ttggaagtat tactgcctgc cttcaggatg ggggagctac gggctagctg    7680
tggaagaaga gctgcaccta acggagaagc ttttctgggg gattattgac tcgctctccc    7740
ataagaaata tgacccagat cttttccgaa tggccctgcc ttgtctcagt gctatagctg    7800
gggccttgcc accagattat ttagattcca gaatcacagc cacgttggag aaacagatct    7860
cagtggatgc ggatggcaac tttgacccaa aacctattaa caccatgaat ttttccttgc    7920
ctgaaaaatt ggaatacatc gtcaccaagt atgctgagca ttcacatgat aaatgggcct    7980
gtgacaagag tcagagtgga tggaaatatg ggatttccct ggatgaaaat gtgaagaccc    8040
acccactgat aaggcctttc aagacattaa cggagaagga aaggaaatt tatcgctggc    8100 ctgcgcgaga gtccctgaaa accatgctgg ctgtgggctg gactgtggag aggaccaaag    8160
agggagaagc tttggttcaa cagcgggaaa atgagaagct tcgaagtgtg tcccaggcca    8220
accagggcaa cagctacagt cctgctcccc tcgacctctc aaacgttgtg ctctccagag    8280
agctccaggg aatggtggag gtcgtggctg agaactatca caatatctgg gccaagaaga    8340
agaagctgga gctggagagc aaaggtggtg gcagccaccc tcttctggta ccatatgaca    8400
ccttgactgc caaggaaaag ttcaaggacc gggagaaggc acaggacctg tttaagttcc    8460
tccaagtgaa tggcatcata gtttccaggg gtatgaagga tatggagctg gatgcctcct    8520
ccatggagaa gaggtttggc tataagttct tgaagaagat cctgaaatac gttgattctg    8580
ctcaagaatt tattgcccat ttagaagcca ttgtcagcag tgggaaaact gaaaagtctc    8640
cccgtgacca ggagatcaaa ttctttgcca aagttctcct cccgctggtt gaccagtact    8700
tcaccagtca ttgcctctac ttcttgtcat cccctctgaa gcccttagc agcagcggat    8760 atgcctccca taaggagaaa gaaatggtgg ccggcctgtt ctgcaaactt gccgctctcg    8820
ttagacacag aatttccctc tttggtagtg attctactac aatggtgagc tgtcttcaca    8880
tcttagctca gacacttgac acaaggactg tcatgaagtc aggctcagag ctggtgaagg    8940
ctgggttacg agcattcttt gaaaatgctg cagaagattt ggagaagact tcagaaaacc    9000
tgaaacttgg gaagttcacc cattcccgaa cgcagattaa aggcgtttct cagaatatta    9060
actacactac agtggctctg ctccccatcc tgacgtccat ctttgagcac gtcactcagc    9120
atcagtttgg aatggatcta ctcttgggtg atgtgcagat ttcatgctac cacatactgt    9180
gcagcctcta ctcccttggg acgggaaaga acatttatgt tgaaaggcaa cgccctgccc    9240
ttggagaatg tctggcctcg ctggcagctg ccataccagt ggcattcctg gagcccaccc    9300
ttaatcgcta caatccactc tcggtcttca acaccaaaac ccccagggag aggtctattc    9360
tggggatgcc agacacggta gaagacatgt gtcctgacat cccccagctg gaaggcctga    9420
tgaaggaaat caacgacctg ccgagtcag gcccggta cacagagatg ccccatgtca    9480
tcgaggtgat cttacccatg ctctgcaact acttgtccta ctggtgggag cggggtcctg    9540
agaacctgcc ccccagcaca gggccatgct gcaccaaggt cacctctgaa cacctcagtc    9600
tcatcctggg caacattctg aaaatcatca acaacaacct gggcatcgat gaggcctcct    9660
ggatgaagcg cattgcagtg tatgcacagc ccatcatcag caaagccagg cccgacctgc    9720
tgagaagcca cttcatccca actctggaga agctgaagaa aaaggctgtc aagacggtgc    9780
aggaggagga gcagttgaaa gccgatggca aaggggacac ccaggaggca gaactcctca    9840
```

-continued

| | | | | | |
|---|---|---|---|---|---|
| tcctggacga | gttcgcggtc | ctctgcagag | atctctatgc | cttctacccc atgctgatcc | 9900 |
| gctacgtgga | caacaacaga | tctaactggc | tgaaaagtcc | tgatgctgat tctgaccagc | 9960 |
| tcttccgcat | ggtggcagaa | gtcttcattc | tgtggtgtaa | atctcataac ttcaagagag | 10020 |
| aagagcaaaa | ttttgtgatt | cagaatgaaa | ttaataattt | ggcatttttta actggagaca | 10080 |
| gcaaaagcaa | gatgtcaaaa | tctggaggac | aagaccagga | gcggaagaag acaaagcggc | 10140 |
| ggggagactt | gtattccatc | cagacctccc | tcatcgtggc | tgcactcaag aaaatgctgc | 10200 |
| ccattggttt | gaatatgtgt | actccaggcg | accaggagct | gatctccctc gcaaaatcgc | 10260 |
| gatacagcca | tagggacaca | gatgaagagg | tcagagaaca | tctgcggaac aacttgcact | 10320 |
| tgcaggaaaa | gtctgatgac | ccagctgtaa | aatggcaact | gaacctctac aaggatgttc | 10380 |
| tgaagagtga | agaacctttc | aatccggaaa | agacagtgga | gcgtgtgcag agaatttcag | 10440 |
| cagctgtctt | ccacctggaa | caggtggaac | agcctttgag | gtccaagaag gccgtctggc | 10500 |
| acaaactgtt | atcaaagcaa | cggaaacggg | cagtggtggc | ctgtttcagg atggcccctc | 10560 |
| tctacaacct | gcccaggcac | cgctctatta | acctcttcct | ccatggctat cagagatttt | 10620 |
| ggatagaaac | agaggagtat | tcctttgaag | agaaactagt | acaggatttg gctaaatctc | 10680 |
| caaaggtgga | agaggaggag | gaggaagaga | cagaaaaaca | acctgaccca ctacatcaga | 10740 |
| tcattctcta | ttttagccgc | aacgctctca | cggagaggag | caaattggaa gacgaccctt | 10800 |
| tgtacacctc | ctattccagc | atgatggcca | agagttgtca | aagtggtgag gatgaagaag | 10860 |
| aagatgaaga | caaggaaaaa | acatttgaag | agaaagagat | ggagaagcaa aaaccctct | 10920 |
| atcagcaagc | tcggctgcat | gagcgtggtg | ctgcagagat | ggtccttcag atgataagcg | 10980 |
| ctagcaaagg | tgagatgagc | cccatggtgg | ttgagacgct | gaagctgggg atcgccattc | 11040 |
| tgaacggagg | caatgctggt | gtgcaacaga | aaatgctaga | ttacctaaag gagaaaaagg | 11100 |
| atgctggatt | ctttcaaagc | cttcctggtc | ttatgcagtc | ttgcagcgtc cttgatttga | 11160 |
| atgcatctga | gaggcagaat | aaagctgaag | gcctggggat | ggtgactgaa gaaggaacac | 11220 |
| tcattgttcg | ggaacgtggt | gaaaaagtac | tccagaatga | cgagttcacg cgtgatctct | 11280 |
| ttagattcct | acagttactt | tgtgagggac | ataacagtga | ctttcagaac ttcctgcgga | 11340 |
| ctcagatggg | caacaccacc | accgtgaatg | tcatcatcag | cactgtggac taccttctgc | 11400 |
| gtctgcagga | atcaatcagt | gatttctact | ggtattattc | agggaaggac atcattgatg | 11460 |
| aatctggaca | gcacaatttt | tccaaagctc | tggcagtcac | caagcagatt ttcaattctc | 11520 |
| ttacagaata | catccagggc | ccttgcattg | gtaatcaaca | gagcctggct cacagcaggc | 11580 |
| tgtgggacgc | agtggttggc | ttcctccatg | tctttgctaa | tatgcagatg aaactctctc | 11640 |
| aggattccag | tcagatcgag | ctgctgaagg | aactcttgga | tctccttcag gacatggtgg | 11700 |
| tgatgcttct | gtccctcctg | gaagggaatg | tggtaaatgg | caccattggc aagcagatgg | 11760 |
| ttgacacact | ggtagaatca | tctaccaatg | tagaaatgat | cttgaaattc tttgacatgt | 11820 |
| tcttgaaact | taaagactta | accagctcag | acaccttcaa | agaatatgac ccagatggta | 11880 |
| aaggaattat | ctccaaaaaa | gaattccaga | aggccatgga | agggcaaaaa cagtacacgc | 11940 |
| agtcagagat | tgactttctc | ctgtcgtgtg | cagaagctga | tgagaatgac atgtttaatt | 12000 |
| acgttgattt | tgtagaccgg | ttccatgagc | cagccaagga | cataggggttt aatgtggctg | 12060 |
| tgttattgac | aaatctttct | gaacacatgc | caaacgattc | ccgcctgaag tgtctgttgg | 12120 |
| acccagcaga | aagtgtgcta | aattacttcg | gaccctacct | aggacgcatc gagatcatgg | 12180 |

-continued

```
gtggggccaa gaagattgag cgtgtttatt ttgagatcag tgaatccagt cgcactcagt   12240
gggagaagcc ccaggtgaag gaatctaagc gacagttcat ttttgatgtt gtcaatgaag   12300
gtggggagca ggaaaagatg gggctgtttg tgaacttctg tgaggacacc atctttgaaa   12360
tgcagttagc atctcagatc tctgaatccg attcagctga caggccagaa gaggaggaag   12420
aagatgaaga ttcttcttac gtgttagaaa ttgcgggtga agaggaagaa gacgggtctc   12480
ttgagccggc ctctgcattt gctatggcct gtgcctctgt gaagaggaat gtcaccgact   12540
tcctgaagag agcaaccctg aagaacctca ggaagcagta caggaacgtg aaaaagatga   12600
ctgcgaagga gctggtgaag gtgctcttct ccttttttctg gatgctgttc gtgggctat   12660 tccagttgct cttcaccatc ctgggaggaa tctttcagat cctctggagc acagtgtttg   12720
gagggggcct ggtagaaggg gcaaagaaca tcagagtgac caagatcctg ggtgacatgc   12780
ctgacccaac ccaatttggt atccatgatg acactatgga ggctgagagg cagaggtga    12840 tggagccagg tatcaccact gaactagtac acttcataaa gggggagaag ggagatacag   12900
atatcatgtc agacctcttt ggactccacc caaagaaaga gggcagctta agcatgggc    12960 ctgaagtggg tttgggtgac ctctcagaaa ttattggcaa ggatgaaccc cctacattag   13020
agagtactgt acagaagaag aggaaagctc aggcagcaga aatgaaagca gcaaatgaag   13080
cagaaggaaa agtagaatcc gagaaggcag acatggaaga tggagagaag gaagacaaag   13140
acaaagaaga ggagcaagct gagtacctgt ggacagaagt gacaaaaaag aagaagcggc   13200
ggtgtggtca gaaggttgag aagccggaag ctttcacagc caatttcttt aaagggctgg   13260
aaatctatca gaccaagtta ctgcattacc tggccaggaa tttctacaac ctgaggttcc   13320
ttgctctgtt tgtagccttc gctatcaact tcatcctgct ttttttataag gtcactgaag   13380 aacctttaga agaagagaca gaggatgttg caaacctatg gaattccttt aatgacgagg   13440
aagaggaaga agcgatggta ttctttgtcc ttcaggagag caccgggtat atggcaccaa   13500
ccctgcgtgc cctggccatc atccatacca tcatctctct agtctgtgtg gtgggctact   13560
actgcctgaa ggtgcctttg gtggttttca aagggaaaa agaaatcgcc aggaagctgg   13620
agtttgatgg cctatatatc accgaacagc catctgaaga tgacatcaag gggcagtggg   13680
accccttggt gatcaacaca ccatctttttc ctaataacta ctgggacaag tttgtaaaga   13740
gaaaggtgat caacaagtat ggagatctct acggagcaga acgcattgct gaacttctgg   13800
gtttggacaa aaatgctctt gactttagcc cagtagaaga gaccaaagca gaagcggctt   13860
ctctggtgtc atggctaagt tccttagaca tgaagtacca tatctggaag cttggagttg   13920
tttttactga caactccttt ctctaccttt cctggtatac aaccatgtca gtcctgggcc   13980
actacaataa cttcttcttt gctgctcacc tattggacat cgcaatgggc ttcaagacac   14040
tgaggaccat tctgtcatct gtaactcaca atggcaaaca gttggttctg actgtcggtc   14100
tcctggccgt ggtggtttat ctctatactg tggtggcttt caacttcttc cgcaagttct   14160
acaacaaaag cgaagacgat gacgagcccg atatgaagtg cgacgacatg atgacgtgtt   14220
accttttcca catgtacgtg ggagtgagag caggaggtgg cattggtgat gaaattgaag   14280
accctgctgg tgatccttat gaaatgtatc gcattgtctt tgacattacc ttttttcttct   14340 tcgtcattgt catcttgctg ccatcattca aggtcttat tattgatgct ttcggagagc   14400
taagagacca gcaggaacaa gtacgagaag atatggagac taaatgtttc atctgtggga   14460
ttggcaatga ctactttgac acaacccctc atgttttga aacacataca ttacaagagc   14520
acaacttagc caactacttg ttctttctga tgtatttgat taataaagat gaaacagagc   14580
```

-continued

```
acacgggtca ggaatcttat gtctggaaga tgtaccaaga aaggtgttgg gatttcttcc    14640
cagccggtga ctgctttcgt aaacaatatg aagatcagct tggataaatc tgaatcaaag    14700
aagcgcgaca attctggaca gtcaacttcc catgaaataa agtccccttt ttacagttct    14760
gcaacatatc tgaaatgtga cattttctaa atgcctccct taaaaaaaaa actgctgaaa    14820
atctgtgcta ttttgaaatt gatttggctt tttgtgccta atggacatac actgtgggag    14880
agaacctgtc aaaatgtcga agaaggaagg cgaagaatca agtaatctct aggcaaatgc    14940
cttcaagttt tccagttctg aggtaactag ttcagtttgt tgggatggaa gcatgaagga    15000
aagggctaga gaagtatgaa atctcgaatg tgtaatacct gaaaatttaa acacttgaat    15060
gtcatcatgg tatccaactt gtgactcata gggtctgaac tccaaaagat aataactgca    15120
gtctaatttt tcccatggta cttgctagtg actgtatcca gaaaagcttt aagcagttaa    15180
agaaacagaa aaaaaccgac actttgtcga cactgaaata tcgattaagt gccttaaaac    15240
ctctttagac atagctatgc aagttttttta tgtttgtgtt ccagaaggac agttccattc    15300
attagttgtg atcttccgtc ttactttatg aaactgcact tgaaggttat tcatacaagt    15360
ttttttagta acagctgtca gtcaactgct gttattagaa gaaaagtact gtactgaaaa    15420
ttcaaaaaaa aatctcaacc ttatgccaaa atggagtaat gctttatggt cccttgtaag    15480
tagtggagct gctctgttta ggtgaatctc ctcaaataca gtgaagtgcc cactgcaata    15540
aagtaatacg tgccaataaa aaaaaaaaa aa                                   15572
```

<210> SEQ ID NO 2
<211> LENGTH: 4866
<212> TYPE: PRT
<213> ORGANISM: Homo sapiens

<400> SEQUENCE: 2

```
Met Ala Glu Gly Gly Glu Gly Gly Glu Asp Glu Ile Gln Phe Leu Arg
1               5                   10                  15

Thr Glu Asp Glu Val Val Leu Gln Cys Ile Ala Thr Ile His Lys Glu
            20                  25                  30

Gln Arg Lys Phe Cys Leu Ala Ala Glu Gly Leu Gly Asn Arg Leu Cys
        35                  40                  45

Phe Leu Glu Pro Thr Ser Glu Ala Lys Tyr Ile Pro Pro Asp Leu Cys
    50                  55                  60

Val Cys Asn Phe Val Leu Glu Gln Ser Leu Ser Val Arg Ala Leu Gln
65                  70                  75                  80

Glu Met Leu Ala Asn Thr Gly Glu Asn Gly Gly Glu Gly Ala Ala Gln
                85                  90                  95

Gly Gly Gly His Arg Thr Leu Leu Tyr Gly His Ala Val Leu Leu Arg
            100                 105                 110

His Ser Phe Ser Gly Met Tyr Leu Thr Cys Leu Thr Thr Ser Arg Ser
        115                 120                 125

Gln Thr Asp Lys Leu Ala Phe Asp Val Gly Leu Arg Glu His Ala Thr
    130                 135                 140

Gly Glu Ala Cys Trp Trp Thr Ile His Pro Ala Ser Lys Gln Arg Ser
145                 150                 155                 160

Glu Gly Glu Lys Val Arg Ile Gly Asp Asp Leu Ile Leu Val Ser Val
                165                 170                 175

Ser Ser Glu Arg Tyr Leu His Leu Ser Val Ser Asn Gly Asn Ile Gln
            180                 185                 190
```

Val Asp Ala Ser Phe Met Gln Thr Leu Trp Asn Val His Pro Thr Cys
    195                 200                 205

Ser Gly Ser Ser Ile Glu Glu Gly Tyr Leu Leu Gly Gly His Val Val
    210                 215                 220

Arg Leu Phe His Gly His Asp Glu Cys Leu Thr Ile Pro Ser Thr Asp
225                 230                 235                 240

Gln Asn Asp Ser Gln His Arg Arg Ile Phe Tyr Glu Ala Gly Gly Ala
                245                 250                 255

Gly Thr Arg Ala Arg Ser Leu Trp Arg Val Glu Pro Leu Arg Ile Ser
                260                 265                 270

Trp Ser Gly Ser Asn Ile Arg Trp Gly Gln Ala Phe Arg Leu Arg His
        275                 280                 285

Leu Thr Thr Gly His Tyr Leu Ala Leu Thr Glu Asp Gln Gly Leu Ile
        290                 295                 300

Leu Gln Asp Arg Ala Lys Ser Asp Thr Lys Ser Thr Ala Phe Ser Phe
305                 310                 315                 320

Arg Ala Ser Lys Glu Leu Lys Glu Lys Leu Asp Ser Ser His Lys Arg
                325                 330                 335

Asp Ile Glu Gly Met Gly Val Pro Glu Ile Lys Tyr Gly Asp Ser Val
                340                 345                 350

Cys Phe Val Gln His Ile Ala Ser Gly Leu Trp Val Thr Tyr Lys Ala
        355                 360                 365

Gln Asp Ala Lys Thr Ser Arg Leu Gly Pro Leu Lys Arg Lys Val Ile
        370                 375                 380

Leu His Gln Glu Gly His Met Asp Asp Gly Leu Thr Leu Gln Arg Cys
385                 390                 395                 400

Gln Arg Glu Glu Ser Gln Ala Ala Arg Ile Ile Arg Asn Thr Thr Ala
                405                 410                 415

Leu Phe Ser Gln Phe Val Ser Gly Asn Asn Arg Thr Ala Ala Pro Ile
                420                 425                 430

Thr Leu Pro Ile Glu Glu Val Leu Gln Thr Leu Gln Asp Leu Ile Ala
        435                 440                 445

Tyr Phe Gln Pro Pro Glu Glu Glu Met Arg His Glu Asp Lys Gln Asn
    450                 455                 460

Lys Leu Arg Ser Leu Lys Asn Arg Gln Asn Leu Phe Lys Glu Glu Gly
465                 470                 475                 480

Met Leu Ala Leu Val Leu Asn Cys Ile Asp Arg Leu Asn Val Tyr Asn
                485                 490                 495

Ser Val Ala His Phe Ala Gly Ile Ala Arg Glu Glu Ser Gly Met Ala
                500                 505                 510

Trp Lys Glu Ile Leu Asn Leu Leu Tyr Lys Leu Leu Ala Ala Leu Ile
        515                 520                 525

Arg Gly Asn Arg Asn Asn Cys Ala Gln Phe Ser Asn Asn Leu Asp Trp
    530                 535                 540

Leu Ile Ser Lys Leu Asp Arg Leu Glu Ser Ser Ser Gly Ile Leu Glu
545                 550                 555                 560

Val Leu His Cys Ile Leu Thr Glu Ser Pro Glu Ala Leu Asn Leu Ile
                565                 570                 575

Ala Glu Gly His Ile Lys Ser Ile Ile Ser Leu Leu Asp Lys His Gly
                580                 585                 590

Arg Asn His Lys Val Leu Asp Ile Leu Cys Ser Leu Cys Leu Cys Asn
        595                 600                 605

Gly Val Ala Val Arg Ala Asn Gln Asn Leu Ile Cys Asp Asn Leu Leu

-continued

```
            610                 615                 620
Pro Arg Arg Asn Leu Leu Leu Gln Thr Arg Leu Ile Asn Asp Val Thr
625                 630                 635                 640

Ser Ile Arg Pro Asn Ile Phe Leu Gly Val Ala Glu Gly Ser Ala Gln
                645                 650                 655

Tyr Lys Lys Trp Tyr Phe Glu Leu Ile Ile Asp Gln Val Asp Pro Phe
                660                 665                 670

Leu Thr Ala Glu Pro Thr His Leu Arg Val Gly Trp Ala Ser Ser Ser
                675                 680                 685

Gly Tyr Ala Pro Tyr Pro Gly Gly Glu Gly Trp Gly Gly Asn Gly
690                 695                 700

Val Gly Asp Asp Leu Tyr Ser Tyr Gly Phe Asp Gly Leu His Leu Trp
705                 710                 715                 720

Ser Gly Arg Ile Pro Arg Ala Val Ala Ser Ile Asn Gln His Leu Leu
                725                 730                 735

Arg Ser Asp Asp Val Gly Lys Leu Leu Pro Gly Pro Arg Gly Cys Pro
                740                 745                 750

Ala Ser His Ser Ala Ser Met Gly Ser Pro Cys Arg Gly Cys Leu Glu
                755                 760                 765

Asn Phe Asn Thr Asp Gly Leu Phe Phe Pro Val Met Ser Phe Ser Ala
770                 775                 780

Gly Val Lys Val Arg Phe Leu Met Gly Gly Arg His Gly Glu Phe Lys
785                 790                 795                 800

Phe Leu Pro Pro Ser Gly Tyr Ala Pro Cys Tyr Glu Ala Leu Leu Pro
                805                 810                 815

Lys Glu Lys Met Arg Leu Glu Pro Val Lys Glu Tyr Lys Arg Asp Ala
                820                 825                 830

Asp Gly Ile Arg Asp Leu Leu Gly Thr Thr Gln Phe Leu Ser Gln Ala
                835                 840                 845

Ser Phe Ile Pro Cys Pro Val Asp Thr Ser Gln Val Ile Leu Pro Pro
850                 855                 860

His Leu Glu Lys Ile Arg Asp Arg Leu Ala Glu Asn Ile His Glu Leu
865                 870                 875                 880

Trp Gly Met Asn Lys Ile Glu Leu Gly Trp Thr Phe Gly Lys Ile Arg
                885                 890                 895

Asp Asp Asn Lys Arg Gln His Pro Cys Leu Val Glu Phe Ser Lys Leu
                900                 905                 910

Pro Glu Thr Glu Lys Asn Tyr Asn Leu Gln Met Ser Thr Glu Thr Leu
                915                 920                 925

Lys Thr Leu Leu Thr Leu Gly Cys His Ile Ala His Val Asn Pro Ala
930                 935                 940

Ala Glu Glu Asp Leu Lys Lys Val Lys Leu Pro Lys Asn Tyr Met Met
945                 950                 955                 960

Ser Asn Gly Tyr Lys Pro Ala Pro Leu Asp Leu Ser Asp Val Lys Leu
                965                 970                 975

Leu Pro Pro Gln Glu Ile Leu Val Asp Lys Leu Ala Glu Asn Ala His
                980                 985                 990

Asn Val Trp Ala Lys Asp Arg Ile Lys Gln Gly Trp Thr Tyr Gly Ile
                995                 1000                1005

Gln Gln Asp Leu Lys Asn Lys Arg Asn Pro Arg Leu Val Pro Tyr
                1010                1015                1020

Ala Leu Leu Asp Glu Arg Thr Lys Lys Ser Asn Arg Asp Ser Leu
                1025                1030                1035
```

-continued

```
Arg Glu Ala Val Arg Thr Phe Val Gly Tyr Gly Tyr Asn Ile Glu
    1040                1045                1050

Pro Ser Asp Gln Glu Leu Ala Asp Ser Ala Val Glu Lys Val Ser
    1055                1060                1065

Ile Asp Lys Ile Arg Phe Phe Arg Val Glu Arg Ser Tyr Pro Val
    1070                1075                1080

Arg Ser Gly Lys Trp Tyr Phe Glu Phe Glu Val Val Thr Gly Gly
    1085                1090                1095

Asp Met Arg Val Gly Trp Ala Arg Pro Gly Cys Arg Pro Asp Val
    1100                1105                1110

Glu Leu Gly Ala Asp Asp Gln Ala Phe Val Phe Glu Gly Asn Arg
    1115                1120                1125

Gly Gln Arg Trp His Gln Gly Ser Gly Tyr Phe Gly Arg Thr Trp
    1130                1135                1140

Gln Pro Gly Asp Val Val Gly Cys Met Ile Asn Leu Asp Asp Ala
    1145                1150                1155

Ser Met Ile Phe Thr Leu Asn Gly Glu Leu Leu Ile Thr Asn Lys
    1160                1165                1170

Gly Ser Glu Leu Ala Phe Ala Asp Tyr Glu Ile Glu Asn Gly Phe
    1175                1180                1185

Val Pro Ile Cys Cys Leu Gly Leu Ser Gln Ile Gly Arg Met Asn
    1190                1195                1200

Leu Gly Thr Asp Ala Ser Thr Phe Lys Phe Tyr Thr Met Cys Gly
    1205                1210                1215

Leu Gln Glu Gly Phe Glu Pro Phe Ala Val Asn Met Asn Arg Asp
    1220                1225                1230

Val Ala Met Trp Phe Ser Lys Arg Leu Pro Thr Phe Val Asn Val
    1235                1240                1245

Pro Lys Asp His Pro His Ile Glu Val Met Arg Ile Asp Gly Thr
    1250                1255                1260

Met Asp Ser Pro Pro Cys Leu Lys Val Thr His Lys Thr Phe Gly
    1265                1270                1275

Thr Gln Asn Ser Asn Ala Asp Met Ile Tyr Cys Arg Leu Ser Met
    1280                1285                1290

Pro Val Glu Cys His Ser Ser Phe Ser His Ser Pro Cys Leu Asp
    1295                1300                1305

Ser Glu Ala Phe Gln Lys Arg Lys Gln Met Gln Glu Ile Leu Ser
    1310                1315                1320

His Thr Thr Thr Gln Cys Tyr Tyr Ala Ile Arg Ile Phe Gly Gly
    1325                1330                1335

Gln Asp Pro Ser Cys Val Trp Val Gly Trp Val Thr Pro Asp Tyr
    1340                1345                1350

His Leu Tyr Ser Glu Lys Phe Asp Leu Asn Lys Asn Cys Thr Val
    1355                1360                1365

Thr Val Thr Leu Gly Asp Glu Arg Gly Arg Val His Glu Ser Val
    1370                1375                1380

Lys Arg Ser Asn Cys Tyr Met Val Trp Gly Gly Asp Ile Val Ala
    1385                1390                1395

Ser Ser Gln Arg Ser Asn Arg Ser Asn Val Asp Leu Glu Ile Gly
    1400                1405                1410

Cys Leu Val Asp Leu Ala Met Gly Met Leu Ser Phe Ser Ala Asn
    1415                1420                1425
```

-continued

| | | | | | | | | | | |
|---|---|---|---|---|---|---|---|---|---|---|
| Gly | Lys 1430 | Glu | Leu | Gly | Thr 1435 | Cys | Tyr | Gln | Val 1440 | Glu | Pro | Asn | Thr | Lys |
| Val | Phe 1445 | Pro | Ala | Val | Phe 1450 | Leu | Gln | Pro | Thr 1455 | Ser | Thr | Ser | Leu | Phe |
| Gln | Phe 1460 | Glu | Leu | Gly | Lys 1465 | Leu | Lys | Asn | Ala 1470 | Met | Pro | Leu | Ser | Ala |
| Ala | Ile 1475 | Phe | Arg | Ser | Glu 1480 | Glu | Asn | Pro | Val 1485 | Pro | Gln | Cys | Pro |
| Pro | Arg 1490 | Leu | Asp | Val | Gln 1495 | Thr | Ile | Gln | Pro 1500 | Val | Leu | Trp | Ser | Arg |
| Met | Pro 1505 | Asn | Ser | Phe | Leu 1510 | Lys | Val | Glu | Thr 1515 | Glu | Arg | Val | Ser | Glu |
| Arg | His 1520 | Gly | Trp | Val | Val 1525 | Gln | Cys | Leu | Glu 1530 | Pro | Leu | Gln | Met | Met |
| Ala | Leu 1535 | His | Ile | Pro | Glu 1540 | Glu | Asn | Arg | Cys 1545 | Val | Asp | Ile | Leu | Glu |
| Leu | Cys 1550 | Glu | Gln | Glu | Asp 1555 | Leu | Met | Arg | Phe 1560 | His | Tyr | His | Thr | Leu |
| Arg | Leu 1565 | Tyr | Ser | Ala | Val 1570 | Cys | Ala | Leu | Gly 1575 | Asn | Ser | Arg | Val | Ala |
| Tyr | Ala 1580 | Leu | Cys | Ser | His 1585 | Val | Asp | Leu | Ser 1590 | Gln | Leu | Phe | Tyr | Ala |
| Ile | Asp 1595 | Asn | Lys | Tyr | Leu 1600 | Pro | Gly | Leu | Leu 1605 | Arg | Ser | Gly | Phe | Tyr |
| Asp | Leu 1610 | Leu | Ile | Ser | Ile 1615 | His | Leu | Ala | Ser 1620 | Ala | Lys | Glu | Arg | Lys |
| Leu | Met 1625 | Met | Lys | Asn | Glu 1630 | Tyr | Ile | Ile | Pro 1635 | Ile | Thr | Ser | Thr | Thr |
| Arg | Asn 1640 | Ile | Cys | Leu | Phe 1645 | Pro | Asp | Glu | Ser 1650 | Lys | Arg | His | Gly | Leu |
| Pro | Gly 1655 | Val | Gly | Leu | Arg 1660 | Thr | Cys | Leu | Lys 1665 | Pro | Gly | Phe | Arg | Phe |
| Ser | Thr 1670 | Pro | Cys | Phe | Val 1675 | Val | Thr | Gly | Asp 1680 | His | Gln | Lys | Gln |
| Ser | Pro 1685 | Glu | Ile | Pro | Leu 1690 | Glu | Ser | Leu | Arg 1695 | Thr | Lys | Ala | Leu | Ser |
| Met | Leu 1700 | Thr | Glu | Ala | Val 1705 | Gln | Cys | Ser | Gly 1710 | Ala | His | Ile | Arg | Asp |
| Pro | Val 1715 | Gly | Gly | Ser | Val 1720 | Glu | Phe | Gln | Phe 1725 | Val | Pro | Val | Leu | Lys |
| Leu | Ile 1730 | Gly | Thr | Leu | Leu 1735 | Val | Met | Gly | Val 1740 | Phe | Asp | Asp | Asp |
| Val | Arg 1745 | Gln | Ile | Leu | Leu 1750 | Leu | Ile | Asp | Pro 1755 | Ser | Val | Phe | Gly | Glu |
| His | Ser 1760 | Ala | Gly | Thr | Glu 1765 | Glu | Gly | Ala | Glu 1770 | Lys | Glu | Glu | Val | Thr |
| Gln | Val 1775 | Glu | Glu | Lys | Ala 1780 | Val | Glu | Ala | Gly 1785 | Glu | Lys | Ala | Gly | Lys |
| Glu | Ala 1790 | Pro | Val | Lys | Gly 1795 | Leu | Leu | Gln | Thr 1800 | Arg | Leu | Pro | Glu | Ser |
| Val | Lys 1805 | Leu | Gln | Met | Cys 1810 | Glu | Leu | Leu | Ser 1815 | Tyr | Leu | Cys | Asp | Cys |
| Glu | Leu | Gln | His | Arg | Val | Glu | Ala | Ile | Val | Ala | Phe | Gly | Asp | Ile |

-continued

```
            1820                1825                1830

Tyr Val Ser Lys Leu Gln Ala Asn Gln Lys Phe Arg Tyr Asn Glu
        1835                1840                1845

Leu Met Gln Ala Leu Asn Met Ser Ala Ala Leu Thr Ala Arg Lys
        1850                1855                1860

Thr Lys Glu Phe Arg Ser Pro Pro Gln Glu Gln Ile Asn Met Leu
        1865                1870                1875

Leu Asn Phe Gln Leu Gly Glu Asn Cys Pro Cys Pro Glu Glu Ile
        1880                1885                1890

Arg Glu Glu Leu Tyr Asp Phe His Glu Asp Leu Leu His Cys
        1895                1900                1905

Gly Val Pro Leu Glu Glu Glu Glu Glu Glu Glu Asp Thr Ser
        1910                1915                1920

Trp Thr Gly Lys Leu Cys Ala Leu Val Tyr Lys Ile Lys Gly Pro
        1925                1930                1935

Pro Lys Pro Glu Lys Glu Gln Pro Thr Glu Glu Glu Arg Cys
        1940                1945                1950

Pro Thr Thr Leu Lys Glu Leu Ile Ser Gln Thr Met Ile Cys Trp
        1955                1960                1965

Ala Gln Glu Asp Gln Ile Gln Asp Ser Glu Leu Val Arg Met Met
        1970                1975                1980

Phe Asn Leu Leu Arg Arg Gln Tyr Asp Ser Ile Gly Glu Leu Leu
        1985                1990                1995

Gln Ala Leu Arg Lys Thr Tyr Thr Ile Ser His Thr Ser Val Ser
        2000                2005                2010

Asp Thr Ile Asn Leu Leu Ala Ala Leu Gly Gln Ile Arg Ser Leu
        2015                2020                2025

Leu Ser Val Arg Met Gly Lys Glu Glu Glu Leu Leu Met Ile Asn
        2030                2035                2040

Gly Leu Gly Asp Ile Met Asn Asn Lys Val Phe Tyr Gln His Pro
        2045                2050                2055

Asn Leu Met Arg Val Leu Gly Met His Glu Thr Val Met Glu Val
        2060                2065                2070

Met Val Asn Val Leu Gly Thr Glu Lys Ser Gln Ile Ala Phe Pro
        2075                2080                2085

Lys Met Val Ala Ser Cys Cys Arg Phe Leu Cys Tyr Phe Cys Arg
        2090                2095                2100

Ile Ser Arg Gln Asn Gln Lys Ala Met Phe Glu His Leu Ser Tyr
        2105                2110                2115

Leu Leu Glu Asn Ser Ser Val Gly Leu Ala Ser Pro Ser Met Arg
        2120                2125                2130

Gly Ser Thr Pro Leu Asp Val Ala Ala Ser Val Met Asp Asn
        2135                2140                2145

Asn Glu Leu Ala Leu Ser Leu Glu Glu Pro Asp Leu Glu Lys Val
        2150                2155                2160

Val Thr Tyr Leu Ala Gly Cys Gly Leu Gln Ser Cys Pro Met Leu
        2165                2170                2175

Leu Ala Lys Gly Tyr Pro Asp Val Gly Trp Asn Pro Ile Glu Gly
        2180                2185                2190

Glu Arg Tyr Leu Ser Phe Leu Arg Phe Ala Val Phe Val Asn Ser
        2195                2200                2205

Glu Ser Val Glu Glu Asn Ala Ser Val Val Val Lys Leu Leu Ile
        2210                2215                2220
```

-continued

```
Arg Arg Pro Glu Cys Phe Gly Pro Ala Leu Arg Gly Glu Gly Gly
    2225                2230                2235
Asn Gly Leu Leu Ala Ala Met Gln Gly Ala Ile Lys Ile Ser Glu
    2240                2245                2250
Asn Pro Ala Leu Asp Leu Pro Ser Gln Gly Tyr Lys Arg Glu Val
    2255                2260                2265
Ser Thr Glu Asp Asp Glu Glu Glu Glu Ile Val His Met Gly
    2270                2275                2280
Asn Ala Ile Met Ser Phe Tyr Ser Ala Leu Ile Asp Leu Leu Gly
    2285                2290                2295
Arg Cys Ala Pro Glu Met His Leu Ile Gln Thr Gly Lys Gly Glu
    2300                2305                2310
Ala Ile Arg Ile Arg Ser Ile Leu Arg Ser Leu Val Pro Thr Glu
    2315                2320                2325
Asp Leu Val Gly Ile Ile Ser Ile Pro Leu Lys Leu Pro Ser Leu
    2330                2335                2340
Asn Lys Asp Gly Ser Val Ser Glu Pro Asp Met Ala Gly Asn Phe
    2345                2350                2355
Cys Pro Asp His Lys Ala Pro Met Val Leu Phe Leu Asp Arg Val
    2360                2365                2370
Tyr Gly Ile Lys Asp Gln Thr Phe Leu Leu His Leu Leu Glu Val
    2375                2380                2385
Gly Phe Leu Pro Asp Leu Arg Ala Ser Ala Ser Leu Asp Thr Val
    2390                2395                2400
Ser Leu Ser Thr Thr Glu Ala Ala Leu Ala Leu Asn Arg Tyr Ile
    2405                2410                2415
Cys Ser Ala Val Leu Pro Leu Leu Thr Arg Cys Ala Pro Leu Phe
    2420                2425                2430
Gly Gly Thr Glu His Cys Thr Ser Leu Ile Asp Ser Thr Leu Gln
    2435                2440                2445
Thr Ile Tyr Arg Leu Ser Lys Gly Arg Ser Leu Thr Lys Ala Gln
    2450                2455                2460
Arg Asp Thr Ile Glu Glu Cys Leu Leu Ala Ile Cys Asn His Leu
    2465                2470                2475
Arg Pro Ser Met Leu Gln Gln Leu Leu Arg Arg Leu Val Phe Asp
    2480                2485                2490
Val Pro Gln Leu Asn Glu Tyr Cys Lys Met Pro Leu Lys Leu Leu
    2495                2500                2505
Thr Asn His Tyr Glu Gln Cys Trp Lys Tyr Tyr Cys Leu Pro Ser
    2510                2515                2520
Gly Trp Gly Ser Tyr Gly Leu Ala Val Glu Glu Glu Leu His Leu
    2525                2530                2535
Thr Glu Lys Leu Phe Trp Gly Ile Ile Asp Ser Leu Ser His Lys
    2540                2545                2550
Lys Tyr Asp Pro Asp Leu Phe Arg Met Ala Leu Pro Cys Leu Ser
    2555                2560                2565
Ala Ile Ala Gly Ala Leu Pro Pro Asp Tyr Leu Asp Ser Arg Ile
    2570                2575                2580
Thr Ala Thr Leu Glu Lys Gln Ile Ser Val Asp Ala Asp Gly Asn
    2585                2590                2595
Phe Asp Pro Lys Pro Ile Asn Thr Met Asn Phe Ser Leu Pro Glu
    2600                2605                2610
```

-continued

```
Lys Leu Glu Tyr Ile Val Thr Lys Tyr Ala Glu His Ser His Asp
2615                2620                2625

Lys Trp Ala Cys Asp Lys Ser Gln Ser Gly Trp Lys Tyr Gly Ile
2630                2635                2640

Ser Leu Asp Glu Asn Val Lys Thr His Pro Leu Ile Arg Pro Phe
2645                2650                2655

Lys Thr Leu Thr Glu Lys Glu Lys Glu Ile Tyr Arg Trp Pro Ala
2660                2665                2670

Arg Glu Ser Leu Lys Thr Met Leu Ala Val Gly Trp Thr Val Glu
2675                2680                2685

Arg Thr Lys Glu Gly Glu Ala Leu Val Gln Gln Arg Glu Asn Glu
2690                2695                2700

Lys Leu Arg Ser Val Ser Gln Ala Asn Gln Gly Asn Ser Tyr Ser
2705                2710                2715

Pro Ala Pro Leu Asp Leu Ser Asn Val Val Leu Ser Arg Glu Leu
2720                2725                2730

Gln Gly Met Val Glu Val Val Ala Glu Asn Tyr His Asn Ile Trp
2735                2740                2745

Ala Lys Lys Lys Lys Leu Glu Leu Glu Ser Lys Gly Gly Gly Ser
2750                2755                2760

His Pro Leu Leu Val Pro Tyr Asp Thr Leu Thr Ala Lys Glu Lys
2765                2770                2775

Phe Lys Asp Arg Glu Lys Ala Gln Asp Leu Phe Lys Phe Leu Gln
2780                2785                2790

Val Asn Gly Ile Ile Val Ser Arg Gly Met Lys Asp Met Glu Leu
2795                2800                2805

Asp Ala Ser Ser Met Glu Lys Arg Phe Gly Tyr Lys Phe Leu Lys
2810                2815                2820

Lys Ile Leu Lys Tyr Val Asp Ser Ala Gln Glu Phe Ile Ala His
2825                2830                2835

Leu Glu Ala Ile Val Ser Ser Gly Lys Thr Glu Lys Ser Pro Arg
2840                2845                2850

Asp Gln Glu Ile Lys Phe Phe Ala Lys Val Leu Leu Pro Leu Val
2855                2860                2865

Asp Gln Tyr Phe Thr Ser His Cys Leu Tyr Phe Leu Ser Ser Pro
2870                2875                2880

Leu Lys Pro Leu Ser Ser Ser Gly Tyr Ala Ser His Lys Glu Lys
2885                2890                2895

Glu Met Val Ala Gly Leu Phe Cys Lys Leu Ala Ala Leu Val Arg
2900                2905                2910

His Arg Ile Ser Leu Phe Gly Ser Asp Ser Thr Thr Met Val Ser
2915                2920                2925

Cys Leu His Ile Leu Ala Gln Thr Leu Asp Thr Arg Thr Val Met
2930                2935                2940

Lys Ser Gly Ser Glu Leu Val Lys Ala Gly Leu Arg Ala Phe Phe
2945                2950                2955

Glu Asn Ala Ala Glu Asp Leu Glu Lys Thr Ser Glu Asn Leu Lys
2960                2965                2970

Leu Gly Lys Phe Thr His Ser Arg Thr Gln Ile Lys Gly Val Ser
2975                2980                2985

Gln Asn Ile Asn Tyr Thr Thr Val Ala Leu Leu Pro Ile Leu Thr
2990                2995                3000

Ser Ile Phe Glu His Val Thr Gln His Gln Phe Gly Met Asp Leu
```

-continued

```
                3005                3010                3015
Leu Leu Gly Asp Val Gln Ile Ser Cys Tyr His Ile Leu Cys Ser
        3020                3025                3030
Leu Tyr Ser Leu Gly Thr Gly Lys Asn Ile Tyr Val Glu Arg Gln
        3035                3040                3045
Arg Pro Ala Leu Gly Glu Cys Leu Ala Ser Leu Ala Ala Ala Ile
        3050                3055                3060
Pro Val Ala Phe Leu Glu Pro Thr Leu Asn Arg Tyr Asn Pro Leu
        3065                3070                3075
Ser Val Phe Asn Thr Lys Thr Pro Arg Glu Arg Ser Ile Leu Gly
        3080                3085                3090
Met Pro Asp Thr Val Glu Asp Met Cys Pro Asp Ile Pro Gln Leu
        3095                3100                3105
Glu Gly Leu Met Lys Glu Ile Asn Asp Leu Ala Glu Ser Gly Ala
        3110                3115                3120
Arg Tyr Thr Glu Met Pro His Val Ile Glu Val Ile Leu Pro Met
        3125                3130                3135
Leu Cys Asn Tyr Leu Ser Tyr Trp Trp Glu Arg Gly Pro Glu Asn
        3140                3145                3150
Leu Pro Pro Ser Thr Gly Pro Cys Cys Thr Lys Val Thr Ser Glu
        3155                3160                3165
His Leu Ser Leu Ile Leu Gly Asn Ile Leu Lys Ile Ile Asn Asn
        3170                3175                3180
Asn Leu Gly Ile Asp Glu Ala Ser Trp Met Lys Arg Ile Ala Val
        3185                3190                3195
Tyr Ala Gln Pro Ile Ile Ser Lys Ala Arg Pro Asp Leu Leu Arg
        3200                3205                3210
Ser His Phe Ile Pro Thr Leu Glu Lys Leu Lys Lys Lys Ala Val
        3215                3220                3225
Lys Thr Val Gln Glu Glu Gln Leu Lys Ala Asp Gly Lys Gly
        3230                3235                3240
Asp Thr Gln Glu Ala Glu Leu Leu Ile Leu Asp Glu Phe Ala Val
        3245                3250                3255
Leu Cys Arg Asp Leu Tyr Ala Phe Tyr Pro Met Leu Ile Arg Tyr
        3260                3265                3270
Val Asp Asn Asn Arg Ser Asn Trp Leu Lys Ser Pro Asp Ala Asp
        3275                3280                3285
Ser Asp Gln Leu Phe Arg Met Val Ala Glu Val Phe Ile Leu Trp
        3290                3295                3300
Cys Lys Ser His Asn Phe Lys Arg Glu Glu Gln Asn Phe Val Ile
        3305                3310                3315
Gln Asn Glu Ile Asn Asn Leu Ala Phe Leu Thr Gly Asp Ser Lys
        3320                3325                3330
Ser Lys Met Ser Lys Ser Gly Gly Gln Asp Gln Glu Arg Lys Lys
        3335                3340                3345
Thr Lys Arg Arg Gly Asp Leu Tyr Ser Ile Gln Thr Ser Leu Ile
        3350                3355                3360
Val Ala Ala Leu Lys Lys Met Leu Pro Ile Gly Leu Asn Met Cys
        3365                3370                3375
Thr Pro Gly Asp Gln Glu Leu Ile Ser Leu Ala Lys Ser Arg Tyr
        3380                3385                3390
Ser His Arg Asp Thr Asp Glu Glu Val Arg Glu His Leu Arg Asn
        3395                3400                3405
```

-continued

```
Asn Leu His Leu Gln Glu Lys Ser Asp Asp Pro Ala Val Lys Trp
3410                3415                3420

Gln Leu Asn Leu Tyr Lys Asp Val Leu Lys Ser Glu Glu Pro Phe
3425                3430                3435

Asn Pro Glu Lys Thr Val Glu Arg Val Gln Arg Ile Ser Ala Ala
3440                3445                3450

Val Phe His Leu Glu Gln Val Glu Gln Pro Leu Arg Ser Lys Lys
3455                3460                3465

Ala Val Trp His Lys Leu Leu Ser Lys Gln Arg Lys Arg Ala Val
3470                3475                3480

Val Ala Cys Phe Arg Met Ala Pro Leu Tyr Asn Leu Pro Arg His
3485                3490                3495

Arg Ser Ile Asn Leu Phe Leu His Gly Tyr Gln Arg Phe Trp Ile
3500                3505                3510

Glu Thr Glu Glu Tyr Ser Phe Glu Glu Lys Leu Val Gln Asp Leu
3515                3520                3525

Ala Lys Ser Pro Lys Val Glu Glu Glu Glu Glu Glu Thr Glu
3530                3535                3540

Lys Gln Pro Asp Pro Leu His Gln Ile Ile Leu Tyr Phe Ser Arg
3545                3550                3555

Asn Ala Leu Thr Glu Arg Ser Lys Leu Glu Asp Asp Pro Leu Tyr
3560                3565                3570

Thr Ser Tyr Ser Ser Met Met Ala Lys Ser Cys Gln Ser Gly Glu
3575                3580                3585

Asp Glu Glu Glu Asp Glu Asp Lys Glu Lys Thr Phe Glu Glu Lys
3590                3595                3600

Glu Met Glu Lys Gln Lys Thr Leu Tyr Gln Gln Ala Arg Leu His
3605                3610                3615

Glu Arg Gly Ala Ala Glu Met Val Leu Gln Met Ile Ser Ala Ser
3620                3625                3630

Lys Gly Glu Met Ser Pro Met Val Val Glu Thr Leu Lys Leu Gly
3635                3640                3645

Ile Ala Ile Leu Asn Gly Gly Asn Ala Gly Val Gln Gln Lys Met
3650                3655                3660

Leu Asp Tyr Leu Lys Glu Lys Lys Asp Ala Gly Phe Phe Gln Ser
3665                3670                3675

Leu Pro Gly Leu Met Gln Ser Cys Ser Val Leu Asp Leu Asn Ala
3680                3685                3690

Ser Glu Arg Gln Asn Lys Ala Glu Gly Leu Gly Met Val Thr Glu
3695                3700                3705

Glu Gly Thr Leu Ile Val Arg Glu Arg Gly Glu Lys Val Leu Gln
3710                3715                3720

Asn Asp Glu Phe Thr Arg Asp Leu Phe Arg Phe Leu Gln Leu Leu
3725                3730                3735

Cys Glu Gly His Asn Ser Asp Phe Gln Asn Phe Leu Arg Thr Gln
3740                3745                3750

Met Gly Asn Thr Thr Thr Val Asn Val Ile Ile Ser Thr Val Asp
3755                3760                3765

Tyr Leu Leu Arg Leu Gln Glu Ser Ile Ser Asp Phe Tyr Trp Tyr
3770                3775                3780

Tyr Ser Gly Lys Asp Ile Ile Asp Glu Ser Gly Gln His Asn Phe
3785                3790                3795
```

```
Ser Lys Ala Leu Ala Val Thr Lys Gln Ile Phe Asn Ser Leu Thr
    3800            3805            3810
Glu Tyr Ile Gln Gly Pro Cys Ile Gly Asn Gln Gln Ser Leu Ala
    3815            3820            3825
His Ser Arg Leu Trp Asp Ala Val Val Gly Phe Leu His Val Phe
    3830            3835            3840
Ala Asn Met Gln Met Lys Leu Ser Gln Asp Ser Ser Gln Ile Glu
    3845            3850            3855
Leu Leu Lys Glu Leu Leu Asp Leu Leu Gln Asp Met Val Val Met
    3860            3865            3870
Leu Leu Ser Leu Leu Glu Gly Asn Val Val Asn Gly Thr Ile Gly
    3875            3880            3885
Lys Gln Met Val Asp Thr Leu Val Glu Ser Ser Thr Asn Val Glu
    3890            3895            3900
Met Ile Leu Lys Phe Phe Asp Met Phe Leu Lys Leu Lys Asp Leu
    3905            3910            3915
Thr Ser Ser Asp Thr Phe Lys Glu Tyr Asp Pro Asp Gly Lys Gly
    3920            3925            3930
Ile Ile Ser Lys Lys Glu Phe Gln Lys Ala Met Glu Gly Gln Lys
    3935            3940            3945
Gln Tyr Thr Gln Ser Glu Ile Asp Phe Leu Leu Ser Cys Ala Glu
    3950            3955            3960
Ala Asp Glu Asn Asp Met Phe Asn Tyr Val Asp Phe Val Asp Arg
    3965            3970            3975
Phe His Glu Pro Ala Lys Asp Ile Gly Phe Asn Val Ala Val Leu
    3980            3985            3990
Leu Thr Asn Leu Ser Glu His Met Pro Asn Asp Ser Arg Leu Lys
    3995            4000            4005
Cys Leu Leu Asp Pro Ala Glu Ser Val Leu Asn Tyr Phe Gly Pro
    4010            4015            4020
Tyr Leu Gly Arg Ile Glu Ile Met Gly Gly Ala Lys Lys Ile Glu
    4025            4030            4035
Arg Val Tyr Phe Glu Ile Ser Glu Ser Ser Arg Thr Gln Trp Glu
    4040            4045            4050
Lys Pro Gln Val Lys Glu Ser Lys Arg Gln Phe Ile Phe Asp Val
    4055            4060            4065
Val Asn Glu Gly Gly Glu Gln Glu Lys Met Gly Leu Phe Val Asn
    4070            4075            4080
Phe Cys Glu Asp Thr Ile Phe Glu Met Gln Leu Ala Ser Gln Ile
    4085            4090            4095
Ser Glu Ser Asp Ser Ala Asp Arg Pro Glu Glu Glu Glu Glu Asp
    4100            4105            4110
Glu Asp Ser Ser Tyr Val Leu Glu Ile Ala Gly Glu Glu Glu Glu
    4115            4120            4125
Asp Gly Ser Leu Glu Pro Ala Ser Ala Phe Ala Met Ala Cys Ala
    4130            4135            4140
Ser Val Lys Arg Asn Val Thr Asp Phe Leu Lys Arg Ala Thr Leu
    4145            4150            4155
Lys Asn Leu Arg Lys Gln Tyr Arg Asn Val Lys Lys Met Thr Ala
    4160            4165            4170
Lys Glu Leu Val Lys Val Leu Phe Ser Phe Phe Trp Met Leu Phe
    4175            4180            4185
Val Gly Leu Phe Gln Leu Leu Phe Thr Ile Leu Gly Gly Ile Phe
```

-continued

```
             4190            4195            4200
Gln Ile Leu Trp Ser Thr Val Phe Gly Gly Leu Val Glu Gly
    4205            4210            4215
Ala Lys Asn Ile Arg Val Thr Lys Ile Leu Gly Asp Met Pro Asp
    4220            4225            4230
Pro Thr Gln Phe Gly Ile His Asp Asp Thr Met Glu Ala Glu Arg
    4235            4240            4245
Ala Glu Val Met Glu Pro Gly Ile Thr Thr Glu Leu Val His Phe
    4250            4255            4260
Ile Lys Gly Glu Lys Gly Asp Thr Asp Ile Met Ser Asp Leu Phe
    4265            4270            4275
Gly Leu His Pro Lys Lys Glu Gly Ser Leu Lys His Gly Pro Glu
    4280            4285            4290
Val Gly Leu Gly Asp Leu Ser Glu Ile Ile Gly Lys Asp Glu Pro
    4295            4300            4305
Pro Thr Leu Glu Ser Thr Val Gln Lys Lys Arg Lys Ala Gln Ala
    4310            4315            4320
Ala Glu Met Lys Ala Ala Asn Glu Ala Glu Gly Lys Val Glu Ser
    4325            4330            4335
Glu Lys Ala Asp Met Glu Asp Gly Glu Lys Glu Asp Lys Asp Lys
    4340            4345            4350
Glu Glu Glu Gln Ala Glu Tyr Leu Trp Thr Glu Val Thr Lys Lys
    4355            4360            4365
Lys Lys Arg Arg Cys Gly Gln Lys Val Glu Lys Pro Glu Ala Phe
    4370            4375            4380
Thr Ala Asn Phe Phe Lys Gly Leu Glu Ile Tyr Gln Thr Lys Leu
    4385            4390            4395
Leu His Tyr Leu Ala Arg Asn Phe Tyr Asn Leu Arg Phe Leu Ala
    4400            4405            4410
Leu Phe Val Ala Phe Ala Ile Asn Phe Ile Leu Leu Phe Tyr Lys
    4415            4420            4425
Val Thr Glu Glu Pro Leu Glu Glu Glu Thr Glu Asp Val Ala Asn
    4430            4435            4440
Leu Trp Asn Ser Phe Asn Asp Glu Glu Glu Glu Ala Met Val
    4445            4450            4455
Phe Phe Val Leu Gln Glu Ser Thr Gly Tyr Met Ala Pro Thr Leu
    4460            4465            4470
Arg Ala Leu Ala Ile Ile His Thr Ile Ile Ser Leu Val Cys Val
    4475            4480            4485
Val Gly Tyr Tyr Cys Leu Lys Val Pro Leu Val Val Phe Lys Arg
    4490            4495            4500
Glu Lys Glu Ile Ala Arg Lys Leu Glu Phe Asp Gly Leu Tyr Ile
    4505            4510            4515
Thr Glu Gln Pro Ser Glu Asp Asp Ile Lys Gly Gln Trp Asp Pro
    4520            4525            4530
Leu Val Ile Asn Thr Pro Ser Phe Pro Asn Asn Tyr Trp Asp Lys
    4535            4540            4545
Phe Val Lys Arg Lys Val Ile Asn Lys Tyr Gly Asp Leu Tyr Gly
    4550            4555            4560
Ala Glu Arg Ile Ala Glu Leu Leu Gly Leu Asp Lys Asn Ala Leu
    4565            4570            4575
Asp Phe Ser Pro Val Glu Glu Thr Lys Ala Glu Ala Ala Ser Leu
    4580            4585            4590
```

-continued

```
Val Ser Trp Leu Ser Ser Leu Asp Met Lys Tyr His Ile Trp Lys
    4595            4600                4605
Leu Gly Val Val Phe Thr Asp Asn Ser Phe Leu Tyr Leu Ala Trp
    4610            4615                4620
Tyr Thr Thr Met Ser Val Leu Gly His Tyr Asn Asn Phe Phe Phe
    4625            4630                4635
Ala Ala His Leu Leu Asp Ile Ala Met Gly Phe Lys Thr Leu Arg
    4640            4645                4650
Thr Ile Leu Ser Ser Val Thr His Asn Gly Lys Gln Leu Val Leu
    4655            4660                4665
Thr Val Gly Leu Leu Ala Val Val Val Tyr Leu Tyr Thr Val Val
    4670            4675                4680
Ala Phe Asn Phe Phe Arg Lys Phe Tyr Asn Lys Ser Glu Asp Asp
    4685            4690                4695
Asp Glu Pro Asp Met Lys Cys Asp Asp Met Met Thr Cys Tyr Leu
    4700            4705                4710
Phe His Met Tyr Val Gly Val Arg Ala Gly Gly Gly Ile Gly Asp
    4715            4720                4725
Glu Ile Glu Asp Pro Ala Gly Asp Pro Tyr Glu Met Tyr Arg Ile
    4730            4735                4740
Val Phe Asp Ile Thr Phe Phe Phe Phe Val Ile Val Ile Leu Leu
    4745            4750                4755
Ala Ile Ile Gln Gly Leu Ile Ile Asp Ala Phe Gly Glu Leu Arg
    4760            4765                4770
Asp Gln Gln Glu Gln Val Arg Glu Asp Met Glu Thr Lys Cys Phe
    4775            4780                4785
Ile Cys Gly Ile Gly Asn Asp Tyr Phe Asp Thr Thr Pro His Gly
    4790            4795                4800
Phe Glu Thr His Thr Leu Gln Glu His Asn Leu Ala Asn Tyr Leu
    4805            4810                4815
Phe Phe Leu Met Tyr Leu Ile Asn Lys Asp Glu Thr Glu His Thr
    4820            4825                4830
Gly Gln Glu Ser Tyr Val Trp Lys Met Tyr Gln Glu Arg Cys Trp
    4835            4840                4845
Asp Phe Phe Pro Ala Gly Asp Cys Phe Arg Lys Gln Tyr Glu Asp
    4850            4855                4860
Gln Leu Gly
    4865

<210> SEQ ID NO 3
<211> LENGTH: 4872
<212> TYPE: PRT
<213> ORGANISM: Oryctolagus cuniculus

<400> SEQUENCE: 3

Met Ala Glu Gly Gly Glu Gly Gly Asp Glu Ile Gln Phe Leu Arg
1               5                   10                  15
Thr Glu Asp Glu Val Val Leu Gln Cys Ile Ala Thr Val His Lys Glu
                20                  25                  30
Gln Arg Lys Phe Cys Leu Ala Ala Glu Gly Leu Gly Asn Arg Leu Cys
            35                  40                  45
Phe Leu Glu Pro Thr Ser Glu Ala Lys Phe Ile Pro Pro Asp Leu Cys
        50                  55                  60
Val Cys Asn Phe Val Leu Glu Gln Ser Leu Ser Val Arg Ala Leu Gln
```

```
                65                  70                  75                  80
Glu Met Leu Ala Asn Thr Gly Glu Asn Gly Gly Glu Gly Ala Ala Gln
                        85                  90                  95
Gly Gly Gly His Arg Thr Leu Leu Tyr Gly His Ala Ile Leu Leu Arg
                100                 105                 110
His Ser Phe Ser Gly Met Tyr Leu Thr Cys Leu Thr Thr Ser Arg Ser
            115                 120                 125
Gln Thr Asp Lys Leu Ala Phe Asp Val Gly Leu Arg Glu His Ala Thr
        130                 135                 140
Gly Glu Ala Cys Trp Trp Thr Ile His Pro Ala Ser Lys Gln Arg Ser
145                 150                 155                 160
Glu Gly Glu Lys Val Arg Ile Gly Asp Asp Leu Ile Leu Val Ser Val
                165                 170                 175
Ser Ser Glu Arg Tyr Leu His Leu Ser Ile Ser Asn Gly Asn Ile Gln
                180                 185                 190
Val Asp Ala Ser Phe Met Gln Thr Leu Trp Asn Val His Pro Thr Cys
            195                 200                 205
Ser Gly Ser Ser Ile Glu Glu Gly Tyr Leu Leu Gly Gly His Val Val
        210                 215                 220
Arg Leu Phe His Gly His Asp Glu Cys Leu Thr Ile Pro Ser Thr Asp
225                 230                 235                 240
Gln Asn Asp Ser Gln His Arg Arg Ile Phe Tyr Glu Ala Gly Gly Ala
                245                 250                 255
Gly Thr Arg Ala Arg Ser Leu Trp Arg Val Glu Pro Leu Arg Ile Ser
                260                 265                 270
Trp Ser Gly Ser Asn Ile Arg Trp Gly Gln Ala Phe Arg Leu Arg His
            275                 280                 285
Leu Thr Thr Gly His Tyr Leu Ala Leu Thr Glu Asp Gln Gly Leu Leu
        290                 295                 300
Leu Gln Asp Arg Gly Lys Ala Asp Thr Lys Ser Thr Ala Phe Ser Phe
305                 310                 315                 320
Arg Pro Ser Lys Glu Thr Lys Glu Lys Leu Asp Ser Ser His Lys Arg
                325                 330                 335
Asp Ile Glu Gly Met Gly Val Pro Glu Ile Lys Tyr Gly Asp Ser Val
                340                 345                 350
Cys Phe Val Gln His Ile Ala Ser Gly Leu Trp Val Thr Tyr Lys Ala
            355                 360                 365
Gln Asp Ala Lys Thr Ser Arg Leu Gly Pro Leu Lys Arg Lys Val Ile
        370                 375                 380
Leu His Gln Glu Gly His Met Asp Asp Gly Leu Thr Leu Gln Arg Cys
385                 390                 395                 400
Gln Arg Glu Glu Ser Gln Ala Ala Arg Ile Ile Arg Asn Thr Thr Ala
                405                 410                 415
Leu Phe Ser Gln Phe Val Ser Gly Asn Asn Arg Thr Ala Ala Pro Val
                420                 425                 430
Thr Leu Pro Ile Glu Glu Val Leu Gln Thr Leu His Asp Leu Ile Ala
            435                 440                 445
Tyr Phe Gln Pro Pro Glu Glu Glu Met Gln His Glu Asp Lys Gln Asn
        450                 455                 460
Lys Leu Arg Ser Leu Lys Asn Arg Gln Asn Leu Phe Lys Glu Glu Gly
465                 470                 475                 480
Met Leu Ala Leu Val Leu Asn Cys Ile Asp Arg Leu Asn Ile Tyr Asn
                485                 490                 495
```

-continued

Ser Val Ala His Phe Ala Gly Ile Ala Arg Glu Glu Ser Gly Met Ala
                500                 505                 510

Trp Lys Glu Val Leu Ser Leu Leu Tyr Lys Leu Leu Ala Ala Leu Ile
            515                 520                 525

Arg Gly Asn Arg Asn Thr Cys Ala Gln Phe Ser Asn Asn Leu Asp Trp
        530                 535                 540

Leu Ile Ser Lys Leu Asp Arg Leu Glu Ser Ser Ser Gly Ile Leu Glu
545                 550                 555                 560

Val Leu His Cys Ile Leu Ile Glu Ser Pro Glu Ala Leu Asn Leu Ile
                565                 570                 575

Ala Glu Gly His Ile Lys Ser Ile Ile Ser Leu Leu Asp Lys His Gly
            580                 585                 590

Arg Asn His Lys Val Leu Asp Val Leu Cys Ser Leu Cys Leu Cys Asn
        595                 600                 605

Gly Val Ala Val Arg Ala Asn Gln Asn Leu Ile Cys Asp Asn Leu Leu
610                 615                 620

Pro Arg Arg Asn Leu Leu Leu Gln Thr Arg Leu Ile Asn Asp Val Thr
625                 630                 635                 640

Ser Ile Arg Pro Asn Ile Phe Leu Gly Val Ala Glu Gly Ser Ala Gln
                645                 650                 655

Tyr Lys Lys Trp Tyr Phe Glu Leu Ile Ile Asp Gln Val Asp Pro Phe
            660                 665                 670

Leu Thr Ala Glu Pro Thr His Leu Arg Val Gly Trp Ala Ser Ser Ser
        675                 680                 685

Gly Tyr Ala Pro Tyr Pro Gly Gly Gly Glu Gly Trp Gly Gly Asn Gly
690                 695                 700

Val Gly Asp Asp Leu Tyr Ser Tyr Gly Phe Asp Gly Leu His Leu Trp
705                 710                 715                 720

Ser Gly Arg Ile Pro Arg Ala Val Ala Ser Ile Asn Gln His Leu Leu
                725                 730                 735

Lys Ser Asp Asp Val Val Ser Cys Cys Leu Asp Leu Gly Val Pro Ser
            740                 745                 750

Ile Ser Phe Arg Ile Asn Gly Gln Pro Val Gln Gly Met Phe Glu Asn
        755                 760                 765

Phe Asn Thr Asp Gly Leu Phe Phe Pro Val Met Ser Phe Ser Ala Gly
        770                 775                 780

Val Lys Val Arg Phe Leu Met Gly Gly Arg His Gly Glu Phe Lys Phe
785                 790                 795                 800

Leu Pro Pro Ser Gly Tyr Ala Pro Cys Tyr Glu Ala Leu Leu Pro Lys
                805                 810                 815

Glu Lys Met Arg Leu Glu Pro Val Lys Glu Tyr Lys Arg Asp Ala Glu
            820                 825                 830

Gly Val Arg Asp Leu Leu Gly Thr Thr Gln Phe Leu Ser Gln Ala Ser
        835                 840                 845

Phe Ile Pro Cys Pro Ile Asp Thr Ser Gln Val Val Leu Pro Pro His
        850                 855                 860

Leu Glu Lys Ile Arg Asp Arg Leu Ala Glu Asn Ile His Glu Leu Trp
865                 870                 875                 880

Gly Met Asn Lys Ile Glu Leu Gly Trp Thr Phe Gly Lys Met Arg Asp
                885                 890                 895

Asp Asn Lys Arg Gln His Pro Cys Leu Val Glu Phe Ser Lys Leu Pro
            900                 905                 910

-continued

```
Glu Thr Glu Lys Asn Tyr Asn Leu Gln Met Ser Thr Glu Thr Leu Lys
        915                 920                 925

Thr Leu Leu Ala Leu Gly Cys His Ile Ala His Val Asn Pro Ala Ala
    930                 935                 940

Glu Glu Asp Leu Lys Lys Val Lys Leu Pro Lys Asn Tyr Met Met Ser
945                 950                 955                 960

Asn Gly Tyr Lys Pro Ala Pro Leu Asp Leu Ser Asp Val Lys Leu Leu
                965                 970                 975

Pro Pro Gln Glu Ile Leu Val Asp Lys Leu Ala Glu Asn Ala His Asn
            980                 985                 990

Val Trp Ala Lys Asp Arg Ile Lys Gln Gly Trp Thr Tyr Gly Ile Gln
        995                 1000                1005

Gln Asp Leu Lys Asn Lys Arg Asn Pro Arg Leu Val Pro Tyr Ala
    1010                1015                1020

Leu Leu Asp Glu Arg Thr Lys Lys Ser Asn Arg Asp Ser Leu Arg
    1025                1030                1035

Glu Ala Val Arg Thr Phe Val Gly Tyr Gly Tyr Asn Ile Glu Pro
    1040                1045                1050

Ser Asp Gln Glu Leu Ala Asp Pro Ala Val Glu Lys Val Ser Ile
    1055                1060                1065

Asp Lys Ile Arg Phe Phe Arg Val Glu Arg Ser Tyr Ala Val Arg
    1070                1075                1080

Ser Gly Lys Trp Tyr Phe Glu Phe Glu Val Val Thr Gly Gly Asp
    1085                1090                1095

Met Arg Val Gly Trp Ala Arg Pro Gly Cys Arg Pro Asp Ile Glu
    1100                1105                1110

Leu Gly Pro Met Thr Lys Pro Leu Cys Leu Lys Ala Ala Gly Ala
    1115                1120                1125

Ser Val Gly Thr Lys Val Val Gly Ile Leu Gly Val Pro Trp Gln
    1130                1135                1140

Pro Gly Asp Val Val Gly Cys Met Ile Asn Leu Asp Asp Ala Ser
    1145                1150                1155

Met Ile Phe Thr Leu Asn Gly Glu Leu Leu Ile Thr Asn Lys Gly
    1160                1165                1170

Ser Glu Leu Ala Phe Ala Asp Tyr Glu Ile Glu Asn Gly Phe Val
    1175                1180                1185

Pro Ile Cys Ser Leu Gly Leu Ser Gln Ile Gly Arg Met Asn Leu
    1190                1195                1200

Gly Thr Asp Ala Ser Thr Phe Lys Phe Tyr Thr Met Cys Gly Leu
    1205                1210                1215

Gln Glu Gly Phe Glu Pro Phe Ala Val Asn Met Asn Arg Asp Val
    1220                1225                1230

Ala Met Trp Phe Ser Lys Arg Leu Pro Thr Phe Val Asn Val Pro
    1235                1240                1245

Lys Asp His Pro His Ile Glu Val Val Arg Ile Asp Gly Thr Met
    1250                1255                1260

Asp Ser Pro Pro Cys Leu Lys Val Thr His Lys Thr Phe Gly Thr
    1265                1270                1275

Gln Asn Ser Asn Ala Asn Met Ile Tyr Cys Arg Leu Ser Met Pro
    1280                1285                1290

Val Glu Cys His Ser Ser Phe Ser His Ser Pro Cys Leu Asp Ser
    1295                1300                1305

Glu Ala Phe Gln Lys Arg Lys Gln Met Gln Glu Ile Leu Ser His
```

-continued

|      |      |      |      |      |      |      |      |      |      |
|------|------|------|------|------|------|------|------|------|------|
|      |      |      | 1310 |      |      | 1315 |      |      | 1320 |
| Thr  | Thr  | Thr  | Gln  | Cys  | Phe  | Tyr  | Ser  | Ile  | Arg  | Ile  | Phe  | Ala  | Gly  | Gln  |
|      | 1325 |      |      |      |      | 1330 |      |      |      | 1335 |
| Asp  | Pro  | Ser  | Cys  | Val  | Trp  | Val  | Gly  | Trp  | Val  | Thr  | Pro  | Asp  | Tyr  | His  |
|      | 1340 |      |      |      |      | 1345 |      |      |      | 1350 |
| Leu  | Tyr  | Ser  | Glu  | Lys  | Phe  | Asp  | Leu  | Asn  | Lys  | Asn  | Cys  | Thr  | Val  | Thr  |
|      | 1355 |      |      |      |      | 1360 |      |      |      | 1365 |
| Val  | Thr  | Leu  | Gly  | Asp  | Glu  | Arg  | Gly  | Arg  | Val  | His  | Glu  | Ser  | Val  | Lys  |
|      | 1370 |      |      |      |      | 1375 |      |      |      | 1380 |
| Arg  | Ser  | Asn  | Cys  | Tyr  | Met  | Val  | Trp  | Gly  | Gly  | Asp  | Val  | Val  | Ala  | Ser  |
|      | 1385 |      |      |      |      | 1390 |      |      |      | 1395 |
| Ser  | Gln  | Arg  | Ser  | Ser  | Arg  | Ser  | Asn  | Val  | Asp  | Leu  | Glu  | Ile  | Gly  | Cys  |
|      | 1400 |      |      |      |      | 1405 |      |      |      | 1410 |
| Leu  | Val  | Asp  | Leu  | Ala  | Met  | Gly  | Met  | Leu  | Ser  | Phe  | Ser  | Ala  | Asn  | Gly  |
|      | 1415 |      |      |      |      | 1420 |      |      |      | 1425 |
| Lys  | Glu  | Leu  | Gly  | Thr  | Cys  | Tyr  | Gln  | Val  | Glu  | Pro  | Asn  | Thr  | Lys  | Val  |
|      | 1430 |      |      |      |      | 1435 |      |      |      | 1440 |
| Phe  | Pro  | Ala  | Val  | Phe  | Leu  | Gln  | Pro  | Thr  | Ser  | Thr  | Ser  | Leu  | Phe  | Gln  |
|      | 1445 |      |      |      |      | 1450 |      |      |      | 1455 |
| Phe  | Glu  | Leu  | Gly  | Lys  | Leu  | Lys  | Asn  | Ala  | Met  | Pro  | Leu  | Ser  | Ala  | Ala  |
|      | 1460 |      |      |      |      | 1465 |      |      |      | 1470 |
| Ile  | Phe  | Lys  | Ser  | Glu  | Glu  | Lys  | Asn  | Pro  | Val  | Pro  | Gln  | Cys  | Pro  | Pro  |
|      | 1475 |      |      |      |      | 1480 |      |      |      | 1485 |
| Arg  | Leu  | Asp  | Val  | Gln  | Thr  | Ile  | Gln  | Pro  | Val  | Leu  | Trp  | Ser  | Arg  | Met  |
|      | 1490 |      |      |      |      | 1495 |      |      |      | 1500 |
| Pro  | Asn  | Ser  | Phe  | Leu  | Lys  | Val  | Glu  | Thr  | Glu  | Arg  | Val  | Ser  | Glu  | Arg  |
|      | 1505 |      |      |      |      | 1510 |      |      |      | 1515 |
| His  | Gly  | Trp  | Val  | Val  | Gln  | Cys  | Leu  | Glu  | Pro  | Leu  | Gln  | Met  | Met  | Ala  |
|      | 1520 |      |      |      |      | 1525 |      |      |      | 1530 |
| Leu  | His  | Ile  | Pro  | Glu  | Glu  | Asn  | Arg  | Cys  | Val  | Asp  | Ile  | Leu  | Glu  | Leu  |
|      | 1535 |      |      |      |      | 1540 |      |      |      | 1545 |
| Cys  | Glu  | Gln  | Glu  | Asp  | Leu  | Met  | Gln  | Phe  | His  | Tyr  | His  | Thr  | Leu  | Arg  |
|      | 1550 |      |      |      |      | 1555 |      |      |      | 1560 |
| Leu  | Tyr  | Ser  | Ala  | Val  | Cys  | Ala  | Leu  | Gly  | Asn  | Ser  | Arg  | Val  | Ala  | Tyr  |
|      | 1565 |      |      |      |      | 1570 |      |      |      | 1575 |
| Ala  | Leu  | Cys  | Ser  | His  | Val  | Asp  | Leu  | Ser  | Gln  | Leu  | Phe  | His  | Ala  | Ile  |
|      | 1580 |      |      |      |      | 1585 |      |      |      | 1590 |
| Asp  | Asn  | Lys  | Tyr  | Leu  | Pro  | Gly  | Leu  | Leu  | Arg  | Ser  | Gly  | Phe  | Tyr  | Asp  |
|      | 1595 |      |      |      |      | 1600 |      |      |      | 1605 |
| Leu  | Leu  | Ile  | Ser  | Ile  | His  | Leu  | Ala  | Asn  | Ala  | Lys  | Glu  | Arg  | Lys  | Leu  |
|      | 1610 |      |      |      |      | 1615 |      |      |      | 1620 |
| Met  | Met  | Lys  | Asn  | Glu  | Tyr  | Ile  | Ile  | Pro  | Ile  | Thr  | Ser  | Thr  | Thr  | Arg  |
|      | 1625 |      |      |      |      | 1630 |      |      |      | 1635 |
| Asn  | Ile  | Arg  | Leu  | Tyr  | Pro  | Asp  | Glu  | Ser  | Lys  | Lys  | His  | Gly  | Leu  | Pro  |
|      | 1640 |      |      |      |      | 1645 |      |      |      | 1650 |
| Gly  | Val  | Gly  | Pro  | Arg  | Thr  | Cys  | Leu  | Lys  | Pro  | Gly  | Phe  | Lys  | Phe  | Ser  |
|      | 1655 |      |      |      |      | 1660 |      |      |      | 1665 |
| Thr  | Pro  | Cys  | Phe  | Val  | Val  | Thr  | Asn  | Glu  | Glu  | Arg  | Gln  | Lys  | Gln  | Ser  |
|      | 1670 |      |      |      |      | 1675 |      |      |      | 1680 |
| Pro  | Glu  | Ile  | Pro  | Leu  | Glu  | Ile  | Leu  | Lys  | Met  | Lys  | Ala  | Leu  | Ser  | Met  |
|      | 1685 |      |      |      |      | 1690 |      |      |      | 1695 |
| Leu  | Thr  | Glu  | Ala  | Val  | Gln  | Cys  | Ser  | Gly  | Ala  | His  | Ile  | Arg  | Asp  | Pro  |
|      | 1700 |      |      |      |      | 1705 |      |      |      | 1710 |

-continued

Val Gly Gly Ser Val Glu Phe Gln Phe Val Pro Val Leu Lys Leu
1715                1720              1725

Val Gly Thr Leu Leu Val Met Gly Val Phe Cys Asp Asp Val
1730                1735              1740

Arg Gln Ile Leu Leu Leu Ile Asp Pro Ser Val Phe Gly Glu His
1745                1750              1755

Ser Ala Asp Thr Glu Glu Gly Ala Glu Lys Glu Val Ser Gln
1760                1765              1770

Val Glu Glu Lys Ala Val Glu Ala Gly Glu Lys Thr Ser Lys Glu
1775                1780              1785

Ala Arg Lys Glu Ala Pro Val Arg Gly Leu Leu Gln Thr Arg Leu
1790                1795              1800

Pro Glu Ser Val Lys Leu Gln Met Cys Glu Leu Leu Ser Tyr Leu
1805                1810              1815

Cys Asp Cys Glu Leu Gln His Arg Val Glu Ala Ile Val Ala Phe
1820                1825              1830

Gly Asp Ile Tyr Val Ser Lys Leu Gln Ala Asn Gln Lys Phe Arg
1835                1840              1845

Tyr Asn Glu Leu Met Gln Ala Leu Asn Met Ser Ala Ala Leu Thr
1850                1855              1860

Ala Arg Lys Thr Arg Glu Phe Arg Ser Pro Pro Gln Glu Gln Ile
1865                1870              1875

Asn Met Leu Leu Asn Phe Gln Leu Gly Glu Asn Cys Pro Cys Pro
1880                1885              1890

Glu Glu Ile Arg Glu Glu Leu Tyr Asp Phe His Glu Asp Leu Leu
1895                1900              1905

Val His Cys Gly Val Pro Leu Glu Glu Glu Glu Glu Glu Glu Glu
1910                1915              1920

Asp Thr Ser Trp Thr Gly Lys Leu Arg Thr Leu Val Tyr Lys Ile
1925                1930              1935

Lys Gly Pro Pro Lys Pro Glu Lys Glu Gln Pro Thr Glu Glu Glu
1940                1945              1950

Glu Arg Cys Pro Thr Thr Leu Lys Glu Leu Ile Ser Gln Thr Met
1955                1960              1965

Ile Arg Trp Ala Gln Glu Asp Gln Ile Gln Asp Ala Glu Leu Val
1970                1975              1980

Arg Met Met Phe Asn Leu Leu Arg Arg Gln Tyr Asp Ser Ile Gly
1985                1990              1995

Glu Leu Leu Gln Ala Leu Arg Lys Thr Tyr Thr Ile Ser His Ala
2000                2005              2010

Ser Val Ser Asp Thr Ile Asn Leu Leu Ala Ala Leu Gly Gln Ile
2015                2020              2025

Arg Ser Leu Leu Ser Val Arg Met Gly Arg Glu Glu Leu Leu
2030                2035              2040

Met Ile Asn Gly Leu Gly Asp Ile Met Asn Asn Lys Val Phe Tyr
2045                2050              2055

Gln His Pro Asn Leu Met Arg Val Leu Gly Met His Glu Thr Val
2060                2065              2070

Met Glu Val Met Val Asn Val Leu Gly Thr Glu Lys Ser Gln Ile
2075                2080              2085

Ala Phe Pro Lys Met Val Ala Ser Cys Cys Arg Phe Leu Cys Tyr
2090                2095              2100

-continued

```
Phe Cys Arg Ile Ser Arg Gln Asn Gln Lys Ala Met Phe Glu His
    2105                2110                2115

Leu Ser Tyr Leu Leu Glu Asn Ser Ser Val Gly Leu Ala Ser Pro
    2120                2125                2130

Ser Met Arg Gly Ser Thr Pro Leu Asp Val Ala Ala Ser Ser Val
    2135                2140                2145

Met Asp Asn Asn Glu Leu Ala Leu Gly Leu Glu Pro Asp Leu
    2150                2155                2160

Glu Lys Val Val Thr Tyr Leu Ala Gly Cys Gly Leu Gln Ser Cys
    2165                2170                2175

Pro Met Leu Leu Ala Lys Gly Tyr Pro Asp Val Gly Trp Asn Pro
    2180                2185                2190

Ile Glu Gly Glu Arg Tyr Leu Ser Phe Leu Arg Phe Ala Val Phe
    2195                2200                2205

Val Asn Ser Glu Ser Val Glu Asn Ala Ser Val Val Lys
    2210                2215                2220

Leu Leu Ile Arg Arg Pro Glu Cys Phe Gly Pro Ala Leu Arg Gly
    2225                2230                2235

Glu Gly Gly Asn Gly Leu Leu Ala Ala Met Gln Gly Ala Ile Lys
    2240                2245                2250

Ile Ser Glu Ser Pro Ala Leu Asp Leu Pro Ser Gln Gly Tyr Lys
    2255                2260                2265

Arg Glu Val Pro Glu Asp Gly Glu Glu Glu Glu Ile Val His
    2270                2275                2280

Met Gly Asn Ala Ile Met Ser Phe Tyr Ser Ala Leu Ile Asp Leu
    2285                2290                2295

Leu Gly Arg Cys Ala Pro Glu Met His Leu Ile Gln Thr Gly Lys
    2300                2305                2310

Gly Glu Ala Ile Arg Ile Arg Ser Ile Leu Arg Ser Leu Val Pro
    2315                2320                2325

Thr Glu Asp Leu Val Gly Ile Ile Ser Ile Pro Leu Lys Leu Pro
    2330                2335                2340

Ser Leu Asn Lys Asp Gly Ser Val Ser Glu Pro Asp Met Ala Ala
    2345                2350                2355

Asn Phe Cys Pro Asp His Lys Ala Pro Met Val Leu Phe Leu Asp
    2360                2365                2370

Arg Val Tyr Gly Ile Lys Asp Gln Thr Phe Leu Leu His Leu Leu
    2375                2380                2385

Glu Val Gly Phe Leu Pro Asp Leu Arg Ala Ser Ala Ser Leu Asp
    2390                2395                2400

Thr Val Ala Leu Ser Thr Thr Glu Ser Ala Leu Ala Leu Asn Arg
    2405                2410                2415

Tyr Ile Cys Ser Ala Val Leu Pro Leu Leu Thr Arg Cys Ala Pro
    2420                2425                2430

Leu Phe Ala Gly Thr Glu His Tyr Thr Ser Leu Ile Asp Ser Thr
    2435                2440                2445

Leu Gln Thr Ile Tyr Arg Leu Ser Lys Gly Arg Ser Leu Thr Lys
    2450                2455                2460

Ala Gln Arg Asp Thr Ile Glu Glu Cys Leu Leu Ala Ile Cys Asn
    2465                2470                2475

His Leu Arg Pro Ser Met Leu Gln Gln Leu Leu Arg Arg Leu Val
    2480                2485                2490

Phe Asp Val Pro Gln Leu Asn Asp Tyr Cys Lys Met Pro Leu Lys
```

-continued

```
            2495                2500                2505
Leu Leu Thr Asn His Phe Glu Gln Cys Trp Lys Tyr Tyr Cys Leu
        2510                2515                2520
Pro Ser Gly Trp Gly Ser Tyr Gly Leu Ala Val Glu Glu Glu Leu
        2525                2530                2535
His Leu Thr Glu Lys Leu Phe Trp Gly Ile Phe Asp Ser Leu Ser
        2540                2545                2550
His Lys Lys Tyr Asp Pro Asp Leu Phe Arg Met Ser Leu Pro Cys
        2555                2560                2565
Leu Ser Ala Ile Ala Gly Ala Leu Pro Pro Asp Tyr Leu Asp Thr
        2570                2575                2580
Arg Ile Thr Ala Thr Leu Glu Lys Gln Val Ser Val Asp Ala Asp
        2585                2590                2595
Gly Asn Phe Asp Pro Lys Pro Ile Asn Thr Ile Asn Phe Ser Leu
        2600                2605                2610
Pro Glu Lys Leu Glu Tyr Ile Val Thr Lys Tyr Ala Glu His Ser
        2615                2620                2625
His Asp Lys Trp Ala Cys Glu Lys Ser Gln Ser Gly Trp Lys Tyr
        2630                2635                2640
Gly Ile Ser Leu Asp Glu Asn Val Lys Thr His Pro Leu Ile Arg
        2645                2650                2655
Pro Phe Lys Thr Leu Thr Glu Lys Glu Lys Glu Ile Tyr Arg Trp
        2660                2665                2670
Pro Ala Arg Glu Ser Leu Lys Thr Met Leu Ala Val Gly Trp Thr
        2675                2680                2685
Val Glu Arg Thr Lys Glu Gly Glu Ala Leu Val Gln Leu Arg Glu
        2690                2695                2700
Asn Glu Lys Leu Arg Ser Val Ser Gln Thr Ser Gln Gly Asn Ser
        2705                2710                2715
Tyr Asn Pro Ala Pro Leu Asp Leu Ser Asn Val Val Leu Ser Arg
        2720                2725                2730
Glu Leu Gln Gly Met Val Glu Val Val Ala Glu Asn Tyr His Asn
        2735                2740                2745
Ile Trp Ala Lys Lys Lys Lys Leu Glu Leu Glu Ser Lys Gly Gly
        2750                2755                2760
Gly Ser His Pro Leu Leu Val Pro Tyr Asp Thr Leu Thr Ala Lys
        2765                2770                2775
Glu Lys Phe Arg Asp Arg Glu Lys Ala Gln Asp Leu Phe Lys Phe
        2780                2785                2790
Leu Gln Val Asn Gly Val Ile Val Ser Arg Gly Met Lys Asp Met
        2795                2800                2805
Glu Leu Asp Ala Phe Ser Met Glu Lys Arg Phe Ala Tyr Lys Phe
        2810                2815                2820
Leu Lys Lys Ile Leu Lys Tyr Val Asp Ser Ala Gln Glu Phe Ile
        2825                2830                2835
Ala His Leu Glu Ala Ile Val Ser Ser Gly Lys Thr Glu Lys Ser
        2840                2845                2850
Pro His Asp Gln Glu Ile Lys Phe Phe Ala Lys Val Leu Leu Pro
        2855                2860                2865
Leu Val Asp Gln Tyr Phe Thr Asn His Arg Leu Tyr Phe Leu Ser
        2870                2875                2880
Ser Pro Leu Lys Pro Leu Ser Ser Ser Gly Tyr Ala Ser His Lys
        2885                2890                2895
```

-continued

```
Glu Lys Glu Met Val Ala Ser Leu Phe Cys Lys Leu Ala Ala Leu
2900                2905                2910
Val Arg His Arg Ile Ser Leu Phe Gly Ser Asp Ser Thr Thr Met
2915                2920                2925
Val Ser Cys Leu His Ile Leu Ala Gln Thr Leu Asp Thr Arg Thr
2930                2935                2940
Val Met Lys Ser Gly Ser Glu Leu Val Lys Ala Gly Leu Arg Ala
2945                2950                2955
Phe Phe Glu Ser Ala Ala Glu Asp Leu Glu Lys Thr Ser Glu Asn
2960                2965                2970
Leu Lys Leu Gly Lys Phe Thr His Ser Arg Thr Gln Ile Lys Gly
2975                2980                2985
Val Ser Gln Asn Ile Asn Tyr Thr Thr Val Ala Leu Leu Pro Ile
2990                2995                3000
Leu Thr Ser Ile Phe Glu His Val Ala Gln His Gln Phe Gly Val
3005                3010                3015
Asp Leu Leu Leu Gly Asp Val Gln Ile Ser Cys Tyr Arg Ile Leu
3020                3025                3030
Cys Ser Leu Tyr Ser Leu Gly Thr Gly Lys Asn Ile Tyr Val Glu
3035                3040                3045
Arg Gln Arg Pro Ala Leu Gly Glu Cys Leu Ala Ser Leu Ala Ala
3050                3055                3060
Ala Ile Pro Val Ala Phe Leu Glu Pro Thr Leu Asn Arg Tyr Asn
3065                3070                3075
Ala Leu Ser Val Phe Asn Thr Lys Thr Pro Arg Glu Arg Ser Ile
3080                3085                3090
Leu Gly Met Pro Asp Thr Val Glu Glu Met Cys Pro Asp Ile Pro
3095                3100                3105
Gln Leu Glu Gly Leu Met Lys Glu Ile Asn Asp Leu Ala Glu Ser
3110                3115                3120
Gly Ala Arg Tyr Thr Glu Met Pro His Val Ile Glu Val Ile Leu
3125                3130                3135
Pro Met Leu Cys Asn Tyr Leu Ser Tyr Trp Trp Glu Arg Gly Pro
3140                3145                3150
Glu Asn Leu Ser Pro Ser Thr Gly Pro Cys Cys Ser Lys Val Thr
3155                3160                3165
Ser Glu His Leu Ser Leu Ile Leu Gly Asn Ile Leu Lys Ile Ile
3170                3175                3180
Asn Asn Asn Leu Gly Ile Asp Glu Ala Ser Trp Met Lys Arg Ile
3185                3190                3195
Ala Val Tyr Ala Gln Pro Ile Ile Ser Lys Ala Arg Pro Asp Leu
3200                3205                3210
Leu Arg Ser His Phe Ile Pro Thr Leu Glu Lys Leu Lys Lys Lys
3215                3220                3225
Ala Val Lys Thr Val Gln Glu Glu Glu Gln Leu Lys Ala Asp Gly
3230                3235                3240
Lys Gly Asp Thr Gln Glu Ala Glu Leu Leu Ile Leu Asp Glu Phe
3245                3250                3255
Ala Ile Leu Cys Arg Asp Leu Tyr Ala Phe Tyr Pro Met Leu Ile
3260                3265                3270
Arg Tyr Val Asp Asn Asn Arg Ser Asn Trp Leu Lys Ser Pro Asp
3275                3280                3285
```

-continued

```
Gly Asp Ser Asp Gln Leu Phe Arg Met Val Ala Glu Val Phe Ile
3290                3295                3300
Leu Trp Cys Lys Ser His Asn Phe Lys Arg Glu Glu Gln Asn Phe
3305                3310                3315
Val Ile Gln Asn Glu Ile Asn Asn Leu Ala Phe Leu Thr Gly Asp
3320                3325                3330
Ser Lys Ser Lys Met Ser Lys Ala Met Gln Val Lys Ser Gly Gly
3335                3340                3345
Gln Asp Gln Glu Arg Lys Lys Thr Lys Arg Gly Asp Leu Tyr
3350                3355                3360
Ser Ile Gln Thr Ser Leu Ile Val Ala Ala Leu Lys Lys Met Leu
3365                3370                3375
Pro Ile Gly Leu Asn Met Cys Thr Pro Gly Asp Gln Glu Leu Ile
3380                3385                3390
Ser Leu Ala Lys Ser Arg Tyr Ser Tyr Arg Asp Thr Asp Glu Glu
3395                3400                3405
Val Lys Glu His Leu Arg Asn Asn Leu His Leu Gln Glu Lys Ser
3410                3415                3420
Asp Asp Pro Ala Val Lys Trp Gln Leu Asn Leu Tyr Lys Asp Val
3425                3430                3435
Leu Lys Ser Glu Glu Pro Ser Asn Pro Glu Lys Thr Val Glu Arg
3440                3445                3450
Val Gln Arg Ile Ser Ala Ala Val Phe His Leu Glu Gln Val Glu
3455                3460                3465
Gln Pro Leu Arg Ser Lys Lys Ala Val Trp His Lys Leu Leu Ser
3470                3475                3480
Lys Gln Arg Lys Arg Ala Val Val Ala Cys Phe Arg Met Ala Pro
3485                3490                3495
Leu Tyr Asn Leu Pro Arg His Arg Ser Ile Asn Leu Phe Leu His
3500                3505                3510
Gly Tyr Gln Arg Phe Trp Ile Glu Thr Glu Glu Tyr Ser Phe Glu
3515                3520                3525
Glu Lys Leu Val Gln Asp Leu Ala Lys Ser Pro Lys Val Glu Glu
3530                3535                3540
Glu Glu Glu Glu Glu Met Glu Lys Gln Pro Asp Pro Leu His Gln
3545                3550                3555
Ile Ile Leu His Phe Ser Arg Asn Ala Leu Thr Glu Arg Ser Lys
3560                3565                3570
Leu Glu Asp Asp Pro Leu Tyr Thr Ser Tyr Ser Ser Met Met Ala
3575                3580                3585
Lys Ser Cys Gln Ser Gly Glu Asp Glu Glu Glu Asp Lys Glu
3590                3595                3600
Lys Thr Phe Glu Glu Lys Glu Met Glu Lys Gln Lys Thr Leu Tyr
3605                3610                3615
Gln Gln Ala Arg Leu His Glu Arg Gly Ala Ala Glu Met Val Leu
3620                3625                3630
Gln Met Ile Ser Ala Ser Lys Gly Glu Met Ser Pro Met Val Val
3635                3640                3645
Glu Thr Leu Lys Leu Gly Ile Ala Ile Leu Asn Gly Gly Asn Ala
3650                3655                3660
Gly Val Gln Gln Lys Met Leu Asp Tyr Leu Lys Val Lys Lys Asp
3665                3670                3675
Ala Gly Phe Phe Gln Ser Leu Ser Gly Leu Met Gln Ser Cys Ser
```

-continued

```
              3680              3685              3690

Val Leu Asp Leu Asn Ala Phe Glu Arg Gln Asn Lys Ala Glu Gly
        3695                3700                3705

Leu Gly Met Val Thr Glu Glu Gly Thr Leu Ile Val Arg Glu Arg
        3710                3715                3720

Gly Glu Lys Val Leu Gln Asn Asp Glu Phe Thr Arg Asp Leu Phe
        3725                3730                3735

Arg Phe Leu Gln Leu Leu Cys Glu Gly His Asn Ser Asp Phe Gln
        3740                3745                3750

Asn Phe Leu Arg Thr Gln Met Gly Asn Thr Thr Thr Val Asn Val
        3755                3760                3765

Ile Ile Ser Thr Val Asp Tyr Leu Leu Arg Leu Gln Glu Ser Ile
        3770                3775                3780

Ser Asp Phe Tyr Trp Tyr Tyr Ser Gly Lys Asp Ile Ile Asp Glu
        3785                3790                3795

Ser Gly Gln His Asn Phe Ser Lys Ala Leu Ala Val Thr Lys Gln
        3800                3805                3810

Ile Phe Asn Ser Leu Thr Glu Tyr Ile Gln Gly Pro Cys Ile Gly
        3815                3820                3825

Asn Gln Gln Ser Leu Ala His Ser Arg Leu Trp Asp Ala Val Val
        3830                3835                3840

Gly Phe Leu His Val Phe Ala Asn Met Gln Met Lys Leu Ser Gln
        3845                3850                3855

Asp Ser Ser Gln Ile Glu Leu Leu Lys Glu Leu Leu Asp Leu Leu
        3860                3865                3870

Gln Asp Met Val Val Met Leu Leu Ser Leu Leu Glu Gly Asn Val
        3875                3880                3885

Val Asn Gly Thr Ile Gly Lys Gln Met Val Asp Thr Leu Val Glu
        3890                3895                3900

Ser Ser Thr Asn Val Glu Met Ile Leu Lys Phe Phe Asp Met Phe
        3905                3910                3915

Leu Lys Leu Lys Asp Leu Thr Ser Ser Asp Thr Phe Lys Glu Tyr
        3920                3925                3930

Asp Pro Asp Gly Lys Gly Ile Ile Ser Lys Lys Glu Phe Gln Lys
        3935                3940                3945

Ala Met Glu Gly Gln Lys Gln Tyr Thr Gln Ser Glu Ile Asp Phe
        3950                3955                3960

Leu Leu Ser Cys Ala Glu Ala Asp Glu Asn Asp Met Phe Asn Tyr
        3965                3970                3975

Ile Asp Phe Val Asp Arg Phe His Glu Pro Ala Lys Asp Ile Gly
        3980                3985                3990

Phe Asn Val Ala Val Leu Leu Thr Asn Leu Ser Glu His Met Pro
        3995                4000                4005

Asn Asp Ser Arg Leu Lys Cys Leu Leu Asp Pro Ala Glu Ser Val
        4010                4015                4020

Leu Asn Tyr Phe Glu Pro Tyr Leu Gly Arg Ile Glu Ile Met Gly
        4025                4030                4035

Gly Ala Lys Lys Ile Glu Arg Val Tyr Phe Glu Ile Ser Glu Ser
        4040                4045                4050

Ser Arg Thr Gln Trp Glu Lys Pro Gln Val Lys Glu Ser Lys Arg
        4055                4060                4065

Gln Phe Ile Phe Asp Val Val Asn Glu Gly Gly Glu Gln Glu Lys
        4070                4075                4080
```

-continued

```
Met Glu Leu Phe Val Asn Phe Cys Glu Asp Thr Ile Phe Glu Met
4085                4090                4095

Gln Leu Ala Ser Gln Ile Ser Glu Ser Asp Ser Ala Asp Arg Pro
4100                4105                4110

Glu Glu Glu Glu Gly Asp Glu Glu Ser Ser Tyr Val Leu Glu Ile
4115                4120                4125

Asn Gly Glu Glu Glu Asp Lys Ser Phe Glu Ser Ala Ser Ala
4130                4135                4140

Phe Ala Met Ala Cys Ala Ser Leu Lys Arg Asn Ile Thr Asn Leu
4145                4150                4155

Leu Arg Lys Ala Thr Leu Lys Asn Leu Arg Lys Gln Tyr Arg Asn
4160                4165                4170

Val Lys Lys Met Thr Ala Lys Glu Leu Val Lys Val Phe Phe Ser
4175                4180                4185

Phe Phe Trp Met Leu Phe Val Gly Leu Phe Gln Leu Phe Phe Thr
4190                4195                4200

Ile Val Gly Gly Ile Phe Gln Ile Leu Trp Ser Thr Val Phe Gly
4205                4210                4215

Gly Gly Leu Val Glu Gly Ala Lys Asn Ile Arg Val Thr Lys Ile
4220                4225                4230

Leu Gly Asp Met Pro Asp Pro Thr Gln Phe Gly Ile His Asp Asp
4235                4240                4245

Ala Met Glu Ala Glu Arg Ala Glu Val Ala Glu Ala Gly Ile Thr
4250                4255                4260

Thr Glu Leu Val His Phe Val Lys Gly Glu Arg Gly Asp Thr Glu
4265                4270                4275

Leu Met Ser Asp Leu Phe Gly Leu His Pro Lys Lys Glu Gly Gly
4280                4285                4290

Val Lys His Gly Pro Glu Val Gly Leu Gly Asp Leu Ser Glu Ile
4295                4300                4305

Ile Gly Lys Asp Glu Pro Pro Thr Leu Glu Ser Thr Val Arg Lys
4310                4315                4320

Lys Arg Lys Ala Gln Ala Ala Glu Thr Lys Ala Glu His Glu Ala
4325                4330                4335

Glu Gly Lys Val Glu Ser Glu Lys Ala Asp Leu Glu Asp Gly Glu
4340                4345                4350

Lys Glu Asp Lys Ala Lys Glu Glu Glu Arg Ala Glu Tyr Leu Trp
4355                4360                4365

Ala Glu Val Thr Lys Lys Lys Lys Arg Arg Arg Gly Gln Lys Val
4370                4375                4380

Glu Lys Pro Glu Ala Phe Met Ala Asn Phe Phe Lys Gly Leu Glu
4385                4390                4395

Ile Tyr Gln Thr Lys Leu Leu His Tyr Leu Ala Arg Asn Phe Tyr
4400                4405                4410

Asn Leu Arg Phe Leu Ala Leu Phe Val Ala Phe Ala Ile Asn Phe
4415                4420                4425

Ile Leu Leu Phe Tyr Lys Val Thr Glu Glu Pro Leu Glu Glu Glu
4430                4435                4440

Thr Glu Asp Val Ala Asn Leu Trp Asn Ser Leu Asn Asp Glu Glu
4445                4450                4455

Glu Glu Glu Ala Met Val Phe Phe Val Leu Gln Glu Ser Thr Gly
4460                4465                4470
```

-continued

```
Tyr Met Ala Pro Thr Leu Arg Ala Leu Ala Val His Thr Ile
4475              4480                4485

Ile Ser Leu Val Cys Val Val Gly Tyr Tyr Cys Leu Lys Val Pro
4490              4495                4500

Leu Val Val Phe Lys Arg Glu Lys Glu Ile Ala Arg Lys Leu Glu
4505              4510                4515

Phe Asp Gly Leu Tyr Ile Thr Glu Gln Pro Ser Glu Asp Asp Ile
4520              4525                4530

Lys Gly Gln Trp Asp Arg Leu Val Ile Asn Thr Pro Ser Phe Pro
4535              4540                4545

His Asn Tyr Trp Asp Lys Phe Val Lys Arg Lys Val Ile Asn Lys
4550              4555                4560

Tyr Gly Asp Leu Tyr Gly Ala Glu Arg Ile Ala Glu Leu Leu Gly
4565              4570                4575

Leu Asp Lys Asn Ala Leu Asp Phe Ser Pro Val Glu Glu Thr Thr
4580              4585                4590

Ala Glu Ala Ala Ser Leu Val Ser Trp Leu Ser Ser Ile Asp Met
4595              4600                4605

Lys Tyr His Ile Trp Lys Leu Gly Val Val Phe Thr Asp Asn Ser
4610              4615                4620

Phe Leu Tyr Leu Ala Trp Tyr Thr Thr Met Ser Val Leu Gly His
4625              4630                4635

Tyr Asn Asn Phe Phe Ala Ala His Leu Leu Asp Ile Ala Met
4640              4645                4650

Gly Phe Lys Thr Leu Arg Thr Ile Leu Ser Ser Val Thr His Asn
4655              4660                4665

Gly Lys Gln Leu Val Leu Thr Val Gly Leu Leu Ala Val Val Val
4670              4675                4680

Tyr Leu Tyr Thr Val Val Ala Phe Asn Phe Phe Arg Lys Phe Tyr
4685              4690                4695

Asn Lys Ser Glu Asp Asp Asp Glu Pro Asp Met Lys Cys Asp Asp
4700              4705                4710

Met Met Thr Cys Tyr Leu Phe His Met Tyr Val Gly Val Arg Ala
4715              4720                4725

Gly Gly Gly Ile Gly Asp Glu Ile Glu Asp Pro Ala Gly Asp Pro
4730              4735                4740

Tyr Glu Met Tyr Arg Ile Val Phe Asp Ile Thr Phe Phe Phe Phe
4745              4750                4755

Val Ile Val Ile Leu Leu Ala Ile Ile Gln Gly Leu Ile Ile Asp
4760              4765                4770

Ala Phe Gly Glu Leu Arg Asp Gln Gln Glu Gln Val Arg Glu Asp
4775              4780                4785

Met Glu Thr Lys Cys Phe Ile Cys Gly Ile Gly Asn Asp Tyr Phe
4790              4795                4800

Asp Thr Thr Pro His Gly Phe Glu Thr His Thr Leu Gln Glu His
4805              4810                4815

Asn Leu Ala Asn Tyr Leu Phe Phe Leu Met Tyr Leu Ile Asn Lys
4820              4825                4830

Asp Glu Thr Glu His Thr Gly Gln Glu Ser Tyr Val Trp Lys Met
4835              4840                4845

Tyr Gln Glu Arg Cys Trp Asp Phe Phe Pro Ala Gly Asp Cys Phe
4850              4855                4860

Arg Lys Gln Tyr Glu Asp Gln Leu Gly
```

-continued

```
            4865                4870
```

<210> SEQ ID NO 4
<211> LENGTH: 5037
<212> TYPE: PRT
<213> ORGANISM: Oryctolagus cuniculus

<400> SEQUENCE: 4

```
Met Gly Asp Gly Gly Glu Gly Glu Asp Glu Val Gln Phe Leu Arg Thr
1               5                   10                  15

Asp Asp Glu Val Val Leu Gln Cys Ser Ala Thr Val Leu Lys Glu Gln
                20                  25                  30

Leu Lys Leu Cys Leu Ala Ala Glu Gly Phe Gly Asn Arg Leu Cys Phe
            35                  40                  45

Leu Glu Pro Thr Ser Asn Ala Gln Asn Val Pro Pro Asp Leu Ala Ile
        50                  55                  60

Cys Cys Phe Thr Leu Glu Gln Ser Leu Ser Val Arg Ala Leu Gln Glu
65                  70                  75                  80

Met Leu Ala Asn Thr Val Glu Ala Gly Val Glu Ser Ser Gln Gly Gly
                85                  90                  95

Gly His Arg Thr Leu Leu Tyr Gly His Ala Ile Leu Leu Arg His Ala
                100                 105                 110

His Ser Arg Met Tyr Leu Ser Cys Leu Thr Thr Ser Arg Ser Met Thr
            115                 120                 125

Asp Lys Leu Ala Phe Asp Val Gly Leu Gln Glu Asp Ala Thr Gly Glu
        130                 135                 140

Ala Cys Trp Trp Thr Met His Pro Ala Ser Lys Gln Arg Ser Glu Gly
145                 150                 155                 160

Glu Lys Val Arg Val Gly Asp Asp Leu Ile Leu Val Ser Val Ser Ser
                165                 170                 175

Glu Arg Tyr Leu His Leu Ser Thr Ala Ser Gly Glu Leu Gln Val Asp
            180                 185                 190

Ala Ser Phe Met Gln Thr Leu Trp Asn Met Asn Pro Ile Cys Ser Cys
        195                 200                 205

Cys Glu Glu Gly Tyr Val Thr Gly Gly His Val Leu Arg Leu Phe His
    210                 215                 220

Gly His Met Asp Glu Cys Leu Thr Ile Ser Ala Ala Asp Ser Asp Asp
225                 230                 235                 240

Gln Arg Arg Leu Val Tyr Tyr Glu Gly Gly Ala Val Cys Thr His Ala
                245                 250                 255

Arg Ser Leu Trp Arg Leu Glu Pro Leu Arg Ile Ser Trp Ser Gly Ser
            260                 265                 270

His Leu Arg Trp Gly Gln Pro Leu Arg Ile Arg His Val Thr Thr Gly
        275                 280                 285

Arg Tyr Leu Ala Leu Thr Glu Asp Gln Gly Leu Val Val Val Asp Ala
    290                 295                 300

Cys Lys Ala His Thr Lys Ala Thr Ser Phe Cys Phe Arg Val Ser Lys
305                 310                 315                 320

Glu Lys Leu Asp Thr Ala Pro Lys Arg Asp Val Glu Gly Met Gly Pro
                325                 330                 335

Pro Glu Ile Lys Tyr Gly Glu Ser Leu Cys Phe Val Gln His Val Ala
            340                 345                 350

Ser Gly Leu Trp Leu Thr Tyr Ala Ala Pro Asp Pro Lys Ala Leu Arg
        355                 360                 365
```

-continued

Leu Gly Val Leu Lys Lys Ala Ile Leu His Gln Glu Gly His Met
370                 375                 380

Asp Asp Ala Leu Phe Leu Thr Arg Cys Gln Gln Glu Glu Ser Gln Ala
385                     390                 395                 400

Ala Arg Met Ile His Ser Thr Ala Gly Leu Tyr Asn Gln Phe Ile Lys
                405                 410                 415

Gly Leu Asp Ser Phe Ser Gly Lys Pro Arg Gly Ser Gly Pro Pro Ala
            420                 425                 430

Gly Pro Ala Leu Pro Ile Glu Ala Val Ile Leu Ser Leu Gln Asp Leu
            435                 440                 445

Ile Gly Tyr Phe Glu Pro Pro Ser Glu Glu Leu Gln His Glu Glu Lys
    450                 455                 460

Gln Ser Lys Leu Arg Ser Leu Arg Asn Arg Gln Ser Leu Phe Gln Glu
465                 470                 475                 480

Glu Gly Met Leu Ser Leu Val Leu Asn Cys Ile Asp Arg Leu Asn Val
                485                 490                 495

Tyr Thr Thr Ala Ala His Phe Ala Glu Tyr Ala Gly Glu Glu Ala Ala
                500                 505                 510

Glu Ser Trp Lys Glu Ile Val Asn Leu Leu Tyr Glu Leu Leu Ala Ser
            515                 520                 525

Leu Ile Arg Gly Asn Arg Ala Asn Cys Ala Leu Phe Ser Thr Asn Leu
530                 535                 540

Asp Trp Val Val Ser Lys Leu Asp Arg Leu Glu Ala Ser Ser Gly Ile
545                 550                 555                 560

Leu Glu Val Leu Tyr Cys Val Leu Ile Glu Ser Pro Glu Val Leu Asn
                565                 570                 575

Ile Ile Gln Glu Asn His Ile Lys Ser Ile Ser Leu Leu Asp Lys
            580                 585                 590

His Gly Arg Asn His Lys Val Leu Asp Val Leu Cys Ser Leu Cys Val
            595                 600                 605

Cys Asn Gly Val Ala Val Arg Ser Asn Gln Asp Leu Ile Thr Glu Asn
610                 615                 620

Leu Leu Pro Gly Arg Glu Leu Leu Leu Gln Thr Asn Leu Ile Asn Tyr
625                 630                 635                 640

Val Thr Ser Ile Arg Pro Asn Ile Phe Val Gly Arg Ala Glu Gly Ser
                645                 650                 655

Thr Gln Tyr Gly Lys Trp Tyr Phe Glu Val Met Val Asp Glu Val Val
            660                 665                 670

Pro Phe Leu Thr Ala Gln Ala Thr His Leu Arg Val Gly Trp Ala Leu
    675                 680                 685

Thr Glu Gly Tyr Ser Pro Tyr Pro Gly Gly Gly Glu Gly Trp Gly Gly
690                 695                 700

Asn Gly Val Gly Asp Asp Leu Tyr Ser Tyr Gly Phe Asp Gly Leu His
705                 710                 715                 720

Leu Trp Thr Gly His Val Ala Arg Pro Val Thr Ser Pro Gly Gln His
                725                 730                 735

Leu Leu Ala Pro Glu Asp Val Val Ser Cys Cys Leu Asp Leu Ser Val
            740                 745                 750

Pro Ser Ile Ser Phe Arg Ile Asn Gly Cys Pro Val Gln Gly Val Phe
        755                 760                 765

Glu Ala Phe Asn Leu Asp Gly Leu Phe Phe Pro Val Val Ser Phe Ser
770                 775                 780

Ala Gly Val Lys Val Arg Phe Leu Leu Gly Gly Arg His Gly Glu Phe

-continued

```
            785                 790                 795                 800
    Lys Phe Leu Pro Pro Pro Gly Tyr Ala Pro Cys His Glu Ala Val Leu
                        805                 810                 815
    Pro Arg Glu Arg Leu Arg Leu Glu Pro Ile Lys Glu Tyr Arg Arg Glu
                    820                 825                 830
    Gly Pro Arg Gly Pro His Leu Val Gly Pro Ser Arg Cys Leu Ser His
                    835                 840                 845
    Thr Asp Phe Val Pro Cys Pro Val Asp Thr Val Gln Ile Val Leu Pro
                850                 855                 860
    Pro His Leu Glu Arg Ile Arg Glu Lys Leu Ala Glu Asn Ile His Glu
    865                 870                 875                 880
    Leu Trp Ala Leu Thr Arg Ile Glu Gln Gly Trp Thr Tyr Gly Pro Val
                        885                 890                 895
    Arg Asp Asp Asn Lys Arg Leu His Pro Cys Leu Val Asn Phe His Ser
                    900                 905                 910
    Leu Pro Glu Pro Glu Arg Asn Tyr Asn Leu Gln Met Ser Gly Glu Thr
                    915                 920                 925
    Leu Lys Thr Leu Leu Ala Leu Gly Cys His Val Gly Met Ala Asp Glu
                930                 935                 940
    Lys Ala Glu Asp Asn Leu Lys Lys Thr Lys Leu Pro Lys Thr Tyr Met
    945                 950                 955                 960
    Met Ser Asn Gly Tyr Lys Pro Ala Pro Leu Asp Leu Ser His Val Arg
                        965                 970                 975
    Leu Thr Pro Ala Gln Thr Thr Leu Val Asp Arg Leu Ala Glu Asn Gly
                    980                 985                 990
    His Asn Val Trp Ala Arg Asp Arg  Val Ala Gln Gly Trp  Ser Tyr Ser
                    995                 1000                1005
    Ala Val  Gln Asp Ile Pro Ala  Arg Arg Asn Pro Arg  Leu Val Pro
        1010                1015                1020
    Tyr Arg  Leu Leu Asp Glu Ala  Thr Lys Arg Ser Asn  Arg Asp Ser
        1025                1030                1035
    Leu Cys  Gln Ala Val Arg Thr  Leu Leu Gly Tyr Gly  Tyr Asn Ile
        1040                1045                1050
    Glu Pro  Pro Asp Gln Glu Pro  Ser Gln Val Glu Asn  Gln Ser Arg
        1055                1060                1065
    Trp Asp  Arg Val Arg Ile Phe  Arg Ala Glu Lys Ser  Tyr Thr Val
        1070                1075                1080
    Gln Ser  Gly Arg Trp Tyr Phe  Glu Phe Glu Ala Val  Thr Thr Gly
        1085                1090                1095
    Glu Met  Arg Val Gly Trp Ala  Arg Pro Glu Leu Arg  Pro Asp Val
        1100                1105                1110
    Glu Leu  Gly Ala Asp Glu Leu  Ala Tyr Val Phe Asn  Gly His Arg
        1115                1120                1125
    Gly Gln  Arg Trp His Leu Gly  Ser Glu Pro Phe Gly  Arg Pro Trp
        1130                1135                1140
    Gln Ser  Gly Asp Val Val Gly  Cys Met Ile Asp Leu  Thr Glu Asn
        1145                1150                1155
    Thr Ile  Ile Phe Thr Leu Asn  Gly Glu Val Leu Met  Ser Asp Ser
        1160                1165                1170
    Gly Ser  Glu Thr Ala Phe Arg  Glu Ile Glu Ile Gly  Asp Gly Phe
        1175                1180                1185
    Leu Pro  Val Cys Ser Leu Gly  Pro Gly Gln Val Gly  His Leu Asn
        1190                1195                1200
```

-continued

```
Leu Gly Gln Asp Val Ser Ser Leu Arg Phe Phe Ala Ile Cys Gly
    1205                1210                1215
Leu Gln Glu Gly Phe Glu Pro Phe Ala Ile Asn Met Gln Arg Pro
    1220                1225                1230
Val Thr Thr Trp Phe Ser Lys Ser Leu Pro Gln Phe Glu Pro Val
    1235                1240                1245
Pro Pro Glu His Pro His Tyr Glu Val Ala Arg Met Asp Gly Thr
    1250                1255                1260
Val Asp Thr Pro Pro Cys Leu Arg Leu Ala His Arg Thr Trp Gly
    1265                1270                1275
Ser Gln Asn Ser Leu Val Glu Met Leu Phe Leu Arg Leu Ser Leu
    1280                1285                1290
Pro Val Gln Phe His Gln His Phe Arg Cys Thr Ala Gly Ala Thr
    1295                1300                1305
Pro Leu Ala Pro Pro Gly Leu Gln Pro Pro Ala Glu Asp Glu Ala
    1310                1315                1320
Arg Ala Ala Glu Pro Asp Pro Asp Tyr Glu Asn Leu Arg Arg Ser
    1325                1330                1335
Ala Gly Gly Trp Gly Glu Ala Glu Gly Gly Lys Glu Gly Thr Ala
    1340                1345                1350
Lys Glu Gly Thr Pro Gly Gly Thr Pro Gln Pro Gly Val Glu Ala
    1355                1360                1365
Gln Pro Val Arg Ala Glu Asn Glu Lys Asp Ala Thr Thr Glu Lys
    1370                1375                1380
Asn Lys Lys Arg Gly Phe Leu Phe Lys Ala Lys Lys Ala Ala Met
    1385                1390                1395
Met Thr Gln Pro Pro Ala Thr Pro Ala Leu Pro Arg Leu Pro His
    1400                1405                1410
Asp Val Val Pro Ala Asp Asn Arg Asp Asp Pro Glu Ile Ile Leu
    1415                1420                1425
Asn Thr Thr Thr Tyr Tyr Tyr Ser Val Arg Val Phe Ala Gly Gln
    1430                1435                1440
Glu Pro Ser Cys Val Trp Val Gly Trp Val Thr Pro Asp Tyr His
    1445                1450                1455
Gln His Asp Met Asn Phe Asp Leu Ser Lys Val Arg Ala Val Thr
    1460                1465                1470
Val Thr Met Gly Asp Glu Gln Gly Asn Val His Ser Ser Leu Lys
    1475                1480                1485
Cys Ser Asn Cys Tyr Met Val Trp Gly Gly Asp Phe Val Ser Pro
    1490                1495                1500
Gly Gln Gln Gly Arg Ile Ser His Thr Asp Leu Val Ile Gly Cys
    1505                1510                1515
Leu Val Asp Leu Ala Thr Gly Leu Met Thr Phe Thr Ala Asn Gly
    1520                1525                1530
Lys Glu Ser Asn Thr Phe Phe Gln Val Glu Pro Asn Thr Lys Leu
    1535                1540                1545
Phe Pro Ala Val Phe Val Leu Pro Thr His Gln Asn Val Ile Gln
    1550                1555                1560
Phe Glu Leu Gly Lys Gln Lys Asn Ile Met Pro Leu Ser Ala Ala
    1565                1570                1575
Met Phe Leu Ser Glu Arg Lys Asn Pro Ala Pro Gln Cys Pro Pro
    1580                1585                1590
```

-continued

```
Arg Leu Glu Val Gln Met Leu Met Pro Val Ser Trp Ser Arg Met
1595                1600                1605

Pro Asn His Phe Leu Gln Val Glu Thr Arg Arg Ala Gly Glu Arg
1610                1615                1620

Leu Gly Trp Ala Val Gln Cys Gln Asp Pro Leu Thr Met Met Ala
1625                1630                1635

Leu His Ile Pro Glu Glu Asn Arg Cys Met Asp Ile Leu Glu Leu
1640                1645                1650

Ser Glu Arg Leu Asp Leu Gln Arg Phe His Ser His Thr Leu Arg
1655                1660                1665

Leu Tyr Arg Ala Val Cys Ala Leu Gly Asn Asn Arg Val Ala His
1670                1675                1680

Ala Leu Cys Ser His Val Asp Gln Ala Gln Leu Leu His Ala Leu
1685                1690                1695

Glu Asp Ala His Leu Pro Gly Pro Leu Arg Ala Gly Tyr Tyr Asp
1700                1705                1710

Leu Leu Ile Ser Ile His Leu Glu Ser Ala Cys Arg Ser Arg Arg
1715                1720                1725

Ser Met Leu Ser Glu Tyr Ile Val Pro Leu Thr Pro Glu Thr Arg
1730                1735                1740

Ala Ile Thr Leu Phe Pro Pro Gly Arg Lys Gly Gly Asn Ala Arg
1745                1750                1755

Arg His Gly Leu Pro Gly Val Gly Val Thr Thr Ser Leu Arg Pro
1760                1765                1770

Pro His His Phe Ser Pro Pro Cys Phe Val Ala Ala Leu Pro Ala
1775                1780                1785

Ala Gly Val Ala Glu Ala Pro Ala Arg Leu Ser Pro Ala Ile Pro
1790                1795                1800

Leu Glu Ala Leu Arg Asp Lys Ala Leu Arg Met Leu Gly Glu Ala
1805                1810                1815

Val Arg Asp Gly Gly Gln His Ala Arg Asp Pro Val Gly Gly Ser
1820                1825                1830

Val Glu Phe Gln Phe Val Pro Val Leu Lys Leu Val Ser Thr Leu
1835                1840                1845

Leu Val Met Gly Ile Phe Gly Asp Glu Asp Val Lys Gln Ile Leu
1850                1855                1860

Lys Met Ile Glu Pro Glu Val Phe Thr Glu Glu Glu Glu Glu Glu
1865                1870                1875

Glu Glu Glu Glu Glu Glu Glu Glu Glu Glu Glu Asp Glu Glu
1880                1885                1890

Glu Lys Glu Glu Asp Glu Glu Glu Glu Glu Lys Glu Asp Ala Glu
1895                1900                1905

Lys Glu Glu Glu Glu Ala Pro Glu Gly Glu Lys Glu Asp Leu Glu
1910                1915                1920

Glu Gly Leu Leu Gln Met Lys Leu Pro Glu Ser Val Lys Leu Gln
1925                1930                1935

Met Cys Asn Leu Leu Glu Tyr Phe Cys Asp Gln Glu Leu Gln His
1940                1945                1950

Arg Val Glu Ser Leu Ala Ala Phe Ala Glu Arg Tyr Val Asp Lys
1955                1960                1965

Leu Gln Ala Asn Gln Arg Ser Arg Tyr Ala Leu Leu Met Arg Ala
1970                1975                1980

Phe Thr Met Ser Ala Ala Glu Thr Ala Arg Arg Thr Arg Glu Phe
```

-continued

```
        1985                1990                1995
Arg Ser Pro Pro Gln Glu Gln Ile Asn Met Leu Leu His Phe Lys
        2000                2005                2010

Asp Glu Ala Asp Glu Glu Asp Cys Pro Leu Pro Glu Asp Ile Arg
        2015                2020                2025

Gln Asp Leu Gln Asp Phe His Gln Asp Leu Leu Ala His Cys Gly
        2030                2035                2040

Ile Gln Leu Glu Gly Glu Glu Glu Pro Glu Glu Glu Thr Ser
        2045                2050                2055

Leu Ser Ser Arg Leu Arg Ser Leu Leu Glu Thr Val Arg Leu Val
        2060                2065                2070

Lys Lys Lys Glu Glu Lys Pro Glu Glu Glu Leu Pro Ala Glu Glu
        2075                2080                2085

Lys Lys Pro Gln Ser Leu Gln Glu Leu Val Ser His Met Val Val
        2090                2095                2100

Arg Trp Ala Gln Glu Asp Tyr Val Gln Ser Pro Glu Leu Val Arg
        2105                2110                2115

Ala Met Phe Ser Leu Leu His Arg Gln Tyr Asp Gly Leu Gly Glu
        2120                2125                2130

Leu Leu Arg Ala Leu Pro Arg Ala Tyr Thr Ile Ser Pro Ser Ser
        2135                2140                2145

Val Glu Asp Thr Met Ser Leu Leu Glu Cys Leu Gly Gln Ile Arg
        2150                2155                2160

Ser Leu Leu Ile Val Gln Met Gly Pro Gln Glu Glu Asn Leu Met
        2165                2170                2175

Ile Gln Ser Ile Gly Asn Ile Met Asn Asn Lys Val Phe Tyr Gln
        2180                2185                2190

His Pro Asn Leu Met Arg Ala Leu Gly Met His Glu Thr Val Met
        2195                2200                2205

Glu Val Met Val Asn Val Leu Gly Gly Gly Glu Thr Lys Glu Ile
        2210                2215                2220

Arg Phe Pro Lys Met Val Thr Ser Cys Cys Arg Phe Leu Cys Tyr
        2225                2230                2235

Phe Cys Arg Ile Ser Arg Gln Asn Gln Arg Ser Met Phe Asp His
        2240                2245                2250

Leu Ser Tyr Leu Leu Glu Asn Ser Gly Ile Gly Leu Gly Met Gln
        2255                2260                2265

Gly Ser Thr Pro Leu Asp Val Ala Ala Ala Ser Val Ile Asp Asn
        2270                2275                2280

Asn Glu Leu Ala Leu Ala Leu Gln Glu Gln Asp Leu Glu Lys Val
        2285                2290                2295

Val Ser Tyr Leu Ala Gly Cys Gly Leu Gln Ser Cys Pro Met Leu
        2300                2305                2310

Leu Ala Lys Gly Tyr Pro Asp Ile Gly Trp Asn Pro Cys Gly Gly
        2315                2320                2325

Glu Arg Tyr Leu Asp Phe Leu Arg Phe Ala Val Phe Val Asn Gly
        2330                2335                2340

Glu Ser Val Glu Glu Asn Ala Asn Val Val Val Arg Leu Leu Ile
        2345                2350                2355

Arg Lys Pro Glu Cys Phe Gly Pro Ala Leu Arg Gly Glu Gly Gly
        2360                2365                2370

Ser Gly Leu Leu Ala Ala Ile Glu Glu Ala Ile Arg Ile Ser Glu
        2375                2380                2385
```

-continued

| | | | | | | | | | | |
|---|---|---|---|---|---|---|---|---|---|---|
| Asp | Pro | Ala | Arg | Asp | Gly | Pro | Gly | Val | Arg | Arg | Asp | Arg | Arg | Arg |
| | 2390 | | | | 2395 | | | | 2400 | |
| Glu | His | Phe | Gly | Glu | Glu | Pro | Pro | Glu | Asn | Arg | Val | His | Leu |
| | 2405 | | | | 2410 | | | | 2415 | |
| Gly | His | Ala | Ile | Met | Ser | Phe | Tyr | Ala | Ala | Leu | Ile | Asp | Leu | Leu |
| | 2420 | | | | 2425 | | | | 2430 | |
| Gly | Arg | Cys | Ala | Pro | Glu | Met | His | Leu | Ile | Gln | Ala | Gly | Lys | Gly |
| | 2435 | | | | 2440 | | | | 2445 | |
| Glu | Ala | Leu | Arg | Ile | Arg | Ala | Ile | Leu | Arg | Ser | Leu | Val | Pro | Leu |
| | 2450 | | | | 2455 | | | | 2460 | |
| Asp | Asp | Leu | Val | Gly | Ile | Ile | Ser | Leu | Pro | Leu | Gln | Ile | Pro | Thr |
| | 2465 | | | | 2470 | | | | 2475 | |
| Leu | Gly | Lys | Asp | Gly | Ala | Leu | Val | Gln | Pro | Lys | Met | Ser | Ala | Ser |
| | 2480 | | | | 2485 | | | | 2490 | |
| Phe | Val | Pro | Asp | His | Lys | Ala | Ser | Met | Val | Leu | Phe | Leu | Asp | Arg |
| | 2495 | | | | 2500 | | | | 2505 | |
| Val | Tyr | Gly | Ile | Glu | Asn | Gln | Asp | Phe | Leu | Leu | His | Val | Leu | Asp |
| | 2510 | | | | 2515 | | | | 2520 | |
| Val | Gly | Phe | Leu | Pro | Asp | Met | Arg | Ala | Ala | Ala | Ser | Leu | Asp | Thr |
| | 2525 | | | | 2530 | | | | 2535 | |
| Ala | Thr | Phe | Ser | Thr | Thr | Glu | Met | Ala | Leu | Ala | Leu | Asn | Arg | Tyr |
| | 2540 | | | | 2545 | | | | 2550 | |
| Leu | Cys | Leu | Ala | Val | Leu | Pro | Leu | Ile | Thr | Lys | Cys | Ala | Pro | Leu |
| | 2555 | | | | 2560 | | | | 2565 | |
| Phe | Ala | Gly | Thr | Glu | His | Arg | Ala | Ile | Met | Val | Asp | Ser | Met | Leu |
| | 2570 | | | | 2575 | | | | 2580 | |
| His | Thr | Val | Tyr | Arg | Leu | Ser | Arg | Gly | Arg | Ser | Leu | Thr | Lys | Ala |
| | 2585 | | | | 2590 | | | | 2595 | |
| Gln | Arg | Asp | Val | Ile | Glu | Asp | Cys | Leu | Met | Ala | Leu | Cys | Arg | Tyr |
| | 2600 | | | | 2605 | | | | 2610 | |
| Ile | Arg | Pro | Ser | Met | Leu | Gln | His | Leu | Leu | Arg | Arg | Leu | Val | Phe |
| | 2615 | | | | 2620 | | | | 2625 | |
| Asp | Val | Pro | Ile | Leu | Asn | Glu | Phe | Ala | Lys | Met | Pro | Leu | Lys | Leu |
| | 2630 | | | | 2635 | | | | 2640 | |
| Leu | Thr | Asn | His | Tyr | Glu | Arg | Cys | Trp | Lys | Tyr | Tyr | Cys | Leu | Pro |
| | 2645 | | | | 2650 | | | | 2655 | |
| Thr | Gly | Trp | Ala | Asn | Phe | Gly | Val | Thr | Ser | Glu | Glu | Leu | His |
| | 2660 | | | | 2665 | | | | 2670 | |
| Leu | Thr | Arg | Lys | Leu | Phe | Trp | Gly | Ile | Phe | Asp | Ser | Leu | Ala | His |
| | 2675 | | | | 2680 | | | | 2685 | |
| Lys | Lys | Tyr | Asp | Gln | Glu | Leu | Tyr | Arg | Met | Ala | Met | Pro | Cys | Leu |
| | 2690 | | | | 2695 | | | | 2700 | |
| Cys | Ala | Ile | Ala | Gly | Ala | Leu | Pro | Pro | Asp | Tyr | Val | Asp | Ala | Ser |
| | 2705 | | | | 2710 | | | | 2715 | |
| Tyr | Ser | Ser | Lys | Ala | Glu | Lys | Lys | Ala | Thr | Val | Asp | Ala | Glu | Gly |
| | 2720 | | | | 2725 | | | | 2730 | |
| Asn | Phe | Asp | Pro | Arg | Pro | Val | Glu | Thr | Leu | Asn | Val | Ile | Ile | Pro |
| | 2735 | | | | 2740 | | | | 2745 | |
| Glu | Lys | Leu | Asp | Ser | Phe | Ile | Asn | Lys | Phe | Ala | Glu | Tyr | Thr | His |
| | 2750 | | | | 2755 | | | | 2760 | |
| Glu | Lys | Trp | Ala | Phe | Asp | Lys | Ile | Gln | Asn | Asn | Trp | Ser | Tyr | Gly |
| | 2765 | | | | 2770 | | | | 2775 | |

-continued

```
Glu Asn Val Asp Glu Glu Leu Lys Thr His Pro Met Leu Arg Pro
    2780            2785            2790

Tyr Lys Thr Phe Ser Glu Lys Asp Lys Glu Ile Tyr Arg Trp Pro
    2795            2800            2805

Ile Lys Glu Ser Leu Lys Ala Met Ile Ala Trp Glu Trp Thr Ile
    2810            2815            2820

Glu Lys Ala Arg Glu Gly Glu Glu Arg Thr Glu Lys Lys Lys
    2825            2830            2835

Thr Arg Lys Ile Ser Gln Thr Ala Gln Thr Tyr Asp Pro Arg Glu
    2840            2845            2850

Gly Tyr Asn Pro Gln Pro Pro Asp Leu Ser Gly Val Thr Leu Ser
    2855            2860            2865

Arg Glu Leu Gln Ala Met Ala Glu Gln Leu Ala Glu Asn Tyr His
    2870            2875            2880

Asn Thr Trp Gly Arg Lys Lys Lys Gln Glu Leu Glu Ala Lys Gly
    2885            2890            2895

Gly Gly Thr His Pro Leu Leu Val Pro Tyr Asp Thr Leu Thr Ala
    2900            2905            2910

Lys Glu Lys Ala Arg Asp Arg Glu Lys Ala Gln Glu Leu Leu Lys
    2915            2920            2925

Phe Leu Gln Met Asn Gly Tyr Ala Val Thr Arg Gly Leu Lys Asp
    2930            2935            2940

Met Glu Leu Asp Thr Ser Ser Ile Glu Lys Arg Phe Ala Phe Gly
    2945            2950            2955

Phe Leu Gln Gln Leu Leu Arg Trp Met Asp Ile Ser Gln Glu Phe
    2960            2965            2970

Ile Ala His Leu Glu Ala Val Val Ser Ser Gly Arg Val Glu Lys
    2975            2980            2985

Ser Pro His Glu Gln Glu Ile Lys Phe Phe Ala Lys Ile Leu Leu
    2990            2995            3000

Pro Leu Ile Asn Gln Tyr Phe Thr Asn His Cys Leu Tyr Phe Leu
    3005            3010            3015

Ser Thr Pro Ala Lys Val Leu Gly Ser Gly Gly His Ala Ser Asn
    3020            3025            3030

Lys Glu Lys Glu Met Ile Thr Ser Leu Phe Cys Lys Leu Ala Ala
    3035            3040            3045

Leu Val Arg His Arg Val Ser Leu Phe Gly Thr Asp Ala Pro Ala
    3050            3055            3060

Val Val Asn Cys Leu His Ile Leu Ala Arg Ser Leu Asp Ala Arg
    3065            3070            3075

Thr Val Met Lys Ser Gly Pro Glu Ile Val Lys Ala Gly Leu Arg
    3080            3085            3090

Ser Phe Phe Glu Ser Ala Ser Glu Asp Ile Glu Lys Met Val Glu
    3095            3100            3105

Asn Leu Arg Leu Gly Lys Val Ser Gln Ala Arg Thr Gln Val Lys
    3110            3115            3120

Gly Val Gly Gln Asn Leu Thr Tyr Thr Thr Val Ala Leu Leu Pro
    3125            3130            3135

Val Leu Thr Thr Leu Phe Gln His Ile Ala Gln His Gln Phe Gly
    3140            3145            3150

Asp Asp Val Ile Leu Asp Asp Val Gln Val Ser Cys Tyr Arg Thr
    3155            3160            3165

Leu Cys Ser Ile Tyr Ser Leu Gly Thr Thr Lys Asn Thr Tyr Val
```

-continued

|  | 3170 |  |  |  | 3175 |  |  |  | 3180 |  |  |
| --- | --- | --- | --- | --- | --- | --- | --- | --- | --- | --- | --- |
| Glu | Lys | Leu | Arg | Pro | Ala | Leu | Gly | Glu | Cys | Leu | Ala | Arg | Leu | Ala |
|  | 3185 |  |  |  | 3190 |  |  |  | 3195 |  |  |
| Ala | Ala | Met | Pro | Val | Ala | Phe | Leu | Glu | Pro | Gln | Leu | Asn | Glu | Tyr |
|  | 3200 |  |  |  | 3205 |  |  |  | 3210 |  |  |
| Asn | Ala | Cys | Ser | Val | Tyr | Thr | Thr | Lys | Ser | Pro | Arg | Glu | Arg | Ala |
|  | 3215 |  |  |  | 3220 |  |  |  | 3225 |  |  |
| Ile | Leu | Gly | Leu | Pro | Asn | Ser | Val | Glu | Met | Cys | Pro | Asp | Ile |
|  | 3230 |  |  |  | 3235 |  |  |  | 3240 |  |  |
| Pro | Val | Leu | Asp | Arg | Leu | Met | Ala | Asp | Ile | Gly | Gly | Leu | Ala | Glu |
|  | 3245 |  |  |  | 3250 |  |  |  | 3255 |  |  |
| Ser | Gly | Ala | Arg | Tyr | Thr | Glu | Met | Pro | His | Val | Ile | Glu | Ile | Thr |
|  | 3260 |  |  |  | 3265 |  |  |  | 3270 |  |  |
| Leu | Pro | Met | Leu | Cys | Ser | Tyr | Leu | Pro | Arg | Trp | Trp | Glu | Arg | Gly |
|  | 3275 |  |  |  | 3280 |  |  |  | 3285 |  |  |
| Pro | Glu | Ala | Pro | Pro | Ala | Leu | Pro | Ala | Gly | Ala | Pro | Pro | Pro |
|  | 3290 |  |  |  | 3295 |  |  |  | 3300 |  |  |
| Cys | Thr | Ala | Val | Thr | Ser | Asp | His | Leu | Asn | Ser | Leu | Leu | Gly | Asn |
|  | 3305 |  |  |  | 3310 |  |  |  | 3315 |  |  |
| Ile | Leu | Arg | Ile | Ile | Val | Asn | Asn | Leu | Gly | Ile | Asp | Glu | Ala | Thr |
|  | 3320 |  |  |  | 3325 |  |  |  | 3330 |  |  |
| Trp | Met | Lys | Arg | Leu | Ala | Val | Phe | Ala | Gln | Pro | Ile | Val | Ser | Arg |
|  | 3335 |  |  |  | 3340 |  |  |  | 3345 |  |  |
| Ala | Arg | Pro | Glu | Leu | Leu | His | Ser | His | Phe | Ile | Pro | Thr | Ile | Gly |
|  | 3350 |  |  |  | 3355 |  |  |  | 3360 |  |  |
| Arg | Leu | Arg | Lys | Arg | Ala | Gly | Lys | Val | Val | Ala | Glu | Glu | Glu | Gln |
|  | 3365 |  |  |  | 3370 |  |  |  | 3375 |  |  |
| Leu | Arg | Leu | Glu | Ala | Lys | Ala | Glu | Ala | Glu | Gly | Glu | Leu | Leu |
|  | 3380 |  |  |  | 3385 |  |  |  | 3390 |  |  |
| Val | Arg | Asp | Glu | Phe | Ser | Val | Leu | Cys | Arg | Asp | Leu | Tyr | Ala | Leu |
|  | 3395 |  |  |  | 3400 |  |  |  | 3405 |  |  |
| Tyr | Pro | Leu | Leu | Ile | Arg | Tyr | Val | Asp | Asn | Asn | Arg | Ala | His | Trp |
|  | 3410 |  |  |  | 3415 |  |  |  | 3420 |  |  |
| Leu | Thr | Glu | Pro | Asn | Ala | Asn | Ala | Glu | Glu | Leu | Phe | Arg | Met | Val |
|  | 3425 |  |  |  | 3430 |  |  |  | 3435 |  |  |
| Gly | Glu | Ile | Phe | Ile | Tyr | Trp | Ser | Lys | Ser | His | Asn | Phe | Lys | Arg |
|  | 3440 |  |  |  | 3445 |  |  |  | 3450 |  |  |
| Glu | Glu | Gln | Asn | Phe | Val | Val | Gln | Asn | Glu | Ile | Asn | Asn | Met | Ser |
|  | 3455 |  |  |  | 3460 |  |  |  | 3465 |  |  |
| Phe | Leu | Thr | Ala | Asp | Ser | Lys | Ser | Lys | Met | Ala | Lys | Ala | Gly | Asp |
|  | 3470 |  |  |  | 3475 |  |  |  | 3480 |  |  |
| Ala | Gln | Ser | Gly | Gly | Ser | Asp | Gln | Glu | Arg | Thr | Lys | Lys | Lys | Arg |
|  | 3485 |  |  |  | 3490 |  |  |  | 3495 |  |  |
| Arg | Gly | Asp | Arg | Tyr | Ser | Val | Gln | Thr | Ser | Leu | Ile | Val | Ala | Thr |
|  | 3500 |  |  |  | 3505 |  |  |  | 3510 |  |  |
| Leu | Lys | Lys | Met | Leu | Pro | Ile | Gly | Leu | Asn | Met | Cys | Ala | Pro | Thr |
|  | 3515 |  |  |  | 3520 |  |  |  | 3525 |  |  |
| Asp | Gln | Asp | Leu | Ile | Met | Leu | Ala | Lys | Thr | Arg | Tyr | Ala | Leu | Lys |
|  | 3530 |  |  |  | 3535 |  |  |  | 3540 |  |  |
| Asp | Thr | Asp | Glu | Glu | Val | Arg | Glu | Phe | Leu | Gln | Asn | Asn | Leu | His |
|  | 3545 |  |  |  | 3550 |  |  |  | 3555 |  |  |
| Leu | Gln | Gly | Lys | Val | Glu | Gly | Ser | Pro | Ser | Leu | Arg | Trp | Gln | Met |
|  | 3560 |  |  |  | 3565 |  |  |  | 3570 |  |  |

-continued

```
Ala Leu Tyr Arg Gly Leu Pro Gly Arg Glu Glu Asp Ala Asp Asp
    3575                3580                3585

Pro Glu Lys Ile Val Arg Arg Val Gln Glu Val Ser Ala Val Leu
    3590                3595                3600

Tyr His Leu Glu Gln Thr Glu His Pro Tyr Lys Ser Lys Lys Ala
    3605                3610                3615

Val Trp His Lys Leu Leu Ser Lys Gln Arg Arg Arg Ala Val Val
    3620                3625                3630

Ala Cys Phe Arg Met Thr Pro Leu Tyr Asn Leu Pro Thr His Arg
    3635                3640                3645

Ala Cys Asn Met Phe Leu Glu Ser Tyr Lys Ala Ala Trp Ile Leu
    3650                3655                3660

Thr Glu Asp His Ser Phe Glu Asp Arg Met Ile Asp Asp Leu Ser
    3665                3670                3675

Lys Ala Gly Glu Gln Glu Glu Glu Glu Glu Val Glu Glu Lys
    3680                3685                3690

Lys Pro Asp Pro Leu His Gln Leu Val Leu His Phe Ser Arg Thr
    3695                3700                3705

Ala Leu Thr Glu Lys Ser Lys Leu Asp Glu Asp Tyr Leu Tyr Met
    3710                3715                3720

Ala Tyr Ala Asp Ile Met Ala Lys Ser Cys His Leu Glu Glu Gly
    3725                3730                3735

Gly Glu Asn Gly Glu Ala Glu Glu Glu Val Glu Val Ser Phe
    3740                3745                3750

Glu Glu Lys Glu Met Glu Lys Gln Arg Leu Leu Tyr Gln Gln Ser
    3755                3760                3765

Arg Leu His Thr Arg Gly Ala Ala Glu Met Val Leu Gln Met Ile
    3770                3775                3780

Ser Ala Cys Lys Gly Glu Thr Gly Ala Met Val Ser Ser Thr Leu
    3785                3790                3795

Lys Leu Gly Ile Ser Ile Leu Asn Gly Gly Asn Ala Glu Val Gln
    3800                3805                3810

Gln Lys Met Leu Asp Tyr Leu Lys Asp Lys Lys Glu Val Gly Phe
    3815                3820                3825

Phe Gln Ser Ile Gln Ala Leu Met Gln Thr Cys Ser Val Leu Asp
    3830                3835                3840

Leu Asn Ala Phe Glu Arg Gln Asn Lys Ala Glu Gly Leu Gly Met
    3845                3850                3855

Val Asn Glu Asp Gly Thr Val Ile Asn Arg Gln Asn Gly Glu Lys
    3860                3865                3870

Val Met Ala Asp Asp Glu Phe Thr Gln Asp Leu Phe Arg Phe Leu
    3875                3880                3885

Gln Leu Leu Cys Glu Gly His Asn Asn Asp Phe Gln Asn Tyr Leu
    3890                3895                3900

Arg Thr Gln Thr Gly Asn Thr Thr Thr Ile Asn Ile Ile Ile Cys
    3905                3910                3915

Thr Val Asp Tyr Leu Leu Arg Leu Gln Glu Ser Ile Ser Asp Phe
    3920                3925                3930

Tyr Trp Tyr Tyr Ser Gly Lys Asp Val Ile Glu Glu Gln Gly Lys
    3935                3940                3945

Arg Asn Phe Ser Lys Ala Met Ser Val Ala Lys Gln Val Phe Asn
    3950                3955                3960
```

-continued

Ser Leu Thr Glu Tyr Ile Gln Gly Pro Cys Thr Gly Asn Gln Gln
    3965            3970            3975

Ser Leu Ala His Ser Arg Leu Trp Asp Ala Val Val Gly Phe Leu
    3980            3985            3990

His Val Phe Ala His Met Met Met Lys Leu Ala Gln Asp Ser Ser
    3995            4000            4005

Gln Ile Glu Leu Leu Lys Glu Leu Leu Asp Leu Gln Lys Asp Met
    4010            4015            4020

Val Val Met Leu Leu Ser Leu Leu Glu Gly Asn Val Val Asn Gly
    4025            4030            4035

Met Ile Ala Arg Gln Met Val Asp Met Leu Val Glu Ser Ser Ser
    4040            4045            4050

Asn Val Glu Met Ile Leu Lys Phe Phe Asp Met Phe Leu Lys Leu
    4055            4060            4065

Lys Asp Ile Val Gly Ser Glu Ala Phe Gln Asp Tyr Val Thr Asp
    4070            4075            4080

Pro Arg Gly Leu Ile Ser Lys Lys Asp Phe Gln Lys Ala Met Asp
    4085            4090            4095

Ser Gln Lys Gln Phe Thr Gly Pro Glu Ile Gln Phe Leu Leu Ser
    4100            4105            4110

Cys Ser Glu Ala Asp Glu Asn Glu Met Ile Asn Phe Glu Glu Phe
    4115            4120            4125

Ala Asn Arg Phe Gln Glu Pro Ala Arg Asp Ile Gly Phe Asn Val
    4130            4135            4140

Ala Val Leu Leu Thr Asn Leu Ser Glu His Val Pro His Asp Pro
    4145            4150            4155

Arg Leu Arg Asn Phe Leu Glu Leu Ala Glu Ser Ile Leu Glu Tyr
    4160            4165            4170

Phe Arg Pro Tyr Leu Gly Arg Ile Glu Ile Met Gly Ala Ser Arg
    4175            4180            4185

Arg Ile Glu Arg Ile Tyr Phe Glu Ile Ser Glu Thr Asn Arg Ala
    4190            4195            4200

Gln Trp Glu Met Pro Gln Val Lys Glu Ser Lys Arg Gln Phe Ile
    4205            4210            4215

Phe Asp Val Val Asn Glu Gly Gly Glu Ala Glu Lys Met Glu Leu
    4220            4225            4230

Phe Val Ser Phe Cys Glu Asp Thr Ile Phe Glu Met Gln Ile Ala
    4235            4240            4245

Ala Gln Ile Ser Glu Pro Glu Gly Glu Pro Glu Ala Asp Glu Asp
    4250            4255            4260

Glu Gly Met Gly Glu Ala Ala Ala Glu Gly Ala Glu Glu Gly Ala
    4265            4270            4275

Ala Gly Ala Glu Gly Ala Ala Gly Thr Val Ala Ala Gly Ala Thr
    4280            4285            4290

Ala Arg Leu Ala Ala Ala Ala Arg Ala Leu Arg Gly Leu Ser
    4295            4300            4305

Tyr Arg Ser Leu Arg Arg Arg Val Arg Arg Leu Arg Arg Leu Thr
    4310            4315            4320

Ala Arg Glu Ala Ala Thr Ala Leu Ala Ala Leu Leu Trp Ala Val
    4325            4330            4335

Val Ala Arg Ala Gly Ala Ala Gly Ala Gly Ala Ala Ala Gly Ala
    4340            4345            4350

Leu Arg Leu Leu Trp Gly Ser Leu Phe Gly Gly Gly Leu Val Glu

-continued

|     |     |     |     |     |     |     |     |     |     |     |     |
|-----|-----|-----|-----|-----|-----|-----|-----|-----|-----|-----|-----|
|     |     |     | 4355 |     |     | 4360 |     |     | 4365 |     |     |
| Gly | Ala | Lys | Lys | Val | Thr | Val | Thr | Glu | Leu | Leu | Ala | Gly | Met | Pro |
|     | 4370 |     |     |     | 4375 |     |     |     | 4380 |     |     |
| Asp | Pro | Thr | Ser | Asp | Glu | Val | His | Gly | Glu | Gln | Pro | Ala | Gly | Pro |
|     | 4385 |     |     |     | 4390 |     |     |     | 4395 |     |     |
| Gly | Gly | Asp | Ala | Asp | Gly | Ala | Gly | Glu | Gly | Gly | Glu | Gly | Asp |
|     | 4400 |     |     |     | 4405 |     |     |     | 4410 |     |     |
| Ala | Ala | Glu | Gly | Asp | Gly | Asp | Glu | Glu | Val | Ala | Gly | His | Glu | Ala |
|     | 4415 |     |     |     | 4420 |     |     |     | 4425 |     |     |
| Gly | Pro | Gly | Gly | Ala | Glu | Gly | Val | Val | Ala | Val | Ala | Asp | Gly | Gly |
|     | 4430 |     |     |     | 4435 |     |     |     | 4440 |     |     |
| Pro | Phe | Arg | Pro | Glu | Gly | Ala | Gly | Gly | Leu | Gly | Asp | Met | Gly | Asp |
|     | 4445 |     |     |     | 4450 |     |     |     | 4455 |     |     |
| Thr | Thr | Pro | Ala | Glu | Pro | Pro | Thr | Pro | Glu | Gly | Ser | Pro | Ile | Leu |
|     | 4460 |     |     |     | 4465 |     |     |     | 4470 |     |     |
| Lys | Arg | Lys | Leu | Gly | Val | Asp | Gly | Glu | Glu | Glu | Leu | Val | Pro |
|     | 4475 |     |     |     | 4480 |     |     |     | 4485 |     |     |
| Glu | Pro | Glu | Pro | Glu | Pro | Glu | Pro | Glu | Pro | Glu | Lys | Ala | Asp | Glu |
|     | 4490 |     |     |     | 4495 |     |     |     | 4500 |     |     |
| Glu | Asn | Gly | Glu | Lys | Glu | Glu | Val | Pro | Glu | Ala | Pro | Pro | Glu | Pro |
|     | 4505 |     |     |     | 4510 |     |     |     | 4515 |     |     |
| Pro | Lys | Lys | Ala | Pro | Pro | Ser | Pro | Pro | Ala | Lys | Lys | Glu | Glu | Ala |
|     | 4520 |     |     |     | 4525 |     |     |     | 4530 |     |     |
| Gly | Gly | Ala | Gly | Met | Glu | Phe | Trp | Gly | Glu | Leu | Glu | Val | Gln | Arg |
|     | 4535 |     |     |     | 4540 |     |     |     | 4545 |     |     |
| Val | Lys | Phe | Leu | Asn | Tyr | Leu | Ser | Arg | Asn | Phe | Tyr | Thr | Leu | Arg |
|     | 4550 |     |     |     | 4555 |     |     |     | 4560 |     |     |
| Phe | Leu | Ala | Leu | Phe | Leu | Ala | Phe | Ala | Ile | Asn | Phe | Ile | Leu | Leu |
|     | 4565 |     |     |     | 4570 |     |     |     | 4575 |     |     |
| Phe | Tyr | Lys | Val | Ser | Asp | Ser | Pro | Pro | Gly | Glu | Asp | Asp | Met | Glu |
|     | 4580 |     |     |     | 4585 |     |     |     | 4590 |     |     |
| Gly | Ser | Ala | Ala | Gly | Asp | Leu | Ala | Gly | Ala | Gly | Ser | Gly | Gly | Gly |
|     | 4595 |     |     |     | 4600 |     |     |     | 4605 |     |     |
| Ser | Gly | Trp | Gly | Ser | Gly | Ala | Gly | Glu | Glu | Ala | Glu | Gly | Asp | Glu |
|     | 4610 |     |     |     | 4615 |     |     |     | 4620 |     |     |
| Asp | Glu | Asn | Met | Val | Tyr | Tyr | Phe | Leu | Glu | Glu | Ser | Thr | Gly | Tyr |
|     | 4625 |     |     |     | 4630 |     |     |     | 4635 |     |     |
| Met | Glu | Pro | Ala | Leu | Trp | Cys | Leu | Ser | Leu | Leu | His | Thr | Leu | Val |
|     | 4640 |     |     |     | 4645 |     |     |     | 4650 |     |     |
| Ala | Phe | Leu | Cys | Ile | Ile | Gly | Tyr | Asn | Cys | Leu | Lys | Val | Pro | Leu |
|     | 4655 |     |     |     | 4660 |     |     |     | 4665 |     |     |
| Val | Ile | Phe | Lys | Arg | Glu | Lys | Glu | Leu | Ala | Arg | Lys | Leu | Glu | Phe |
|     | 4670 |     |     |     | 4675 |     |     |     | 4680 |     |     |
| Asp | Gly | Leu | Tyr | Ile | Thr | Glu | Gln | Pro | Gly | Asp | Asp | Asp | Val | Lys |
|     | 4685 |     |     |     | 4690 |     |     |     | 4695 |     |     |
| Gly | Gln | Trp | Asp | Arg | Leu | Val | Leu | Asn | Thr | Pro | Ser | Phe | Pro | Ser |
|     | 4700 |     |     |     | 4705 |     |     |     | 4710 |     |     |
| Asn | Tyr | Trp | Asp | Lys | Phe | Val | Lys | Arg | Lys | Val | Leu | Asp | Lys | His |
|     | 4715 |     |     |     | 4720 |     |     |     | 4725 |     |     |
| Gly | Asp | Ile | Phe | Gly | Arg | Glu | Arg | Ile | Ala | Glu | Leu | Leu | Gly | Met |
|     | 4730 |     |     |     | 4735 |     |     |     | 4740 |     |     |
| Asp | Leu | Ala | Ser | Leu | Glu | Ile | Thr | Ala | His | Asn | Glu | Arg | Lys | Pro |
|     | 4745 |     |     |     | 4750 |     |     |     | 4755 |     |     |

| | | | | | | | | | | |
|---|---|---|---|---|---|---|---|---|---|---|
|Asp|Pro|Pro|Pro|Gly|Leu|Leu|Thr|Trp|Leu|Met|Ser|Ile|Asp|Val|
| |4760| | | |4765| | | |4770| |

Asp Pro Pro Pro Gly Leu Leu Thr Trp Leu Met Ser Ile Asp Val
    4760            4765            4770

Lys Tyr Gln Ile Trp Lys Phe Gly Val Ile Phe Thr Asp Asn Ser
    4775            4780            4785

Phe Leu Tyr Leu Gly Trp Tyr Met Val Met Ser Leu Leu Gly His
    4790            4795            4800

Tyr Asn Asn Phe Phe Ala Ala His Leu Leu Asp Ile Ala Met
    4805            4810            4815

Gly Val Lys Thr Leu Arg Thr Ile Leu Ser Ser Val Thr His Asn
    4820            4825            4830

Gly Lys Gln Leu Val Met Thr Val Gly Leu Leu Ala Val Val Val
    4835            4840            4845

Tyr Leu Tyr Thr Val Val Ala Phe Asn Phe Phe Arg Lys Phe Tyr
    4850            4855            4860

Asn Lys Ser Glu Asp Glu Asp Glu Pro Asp Met Lys Cys Asp Asp
    4865            4870            4875

Met Met Thr Cys Tyr Leu Phe His Met Tyr Val Gly Val Arg Ala
    4880            4885            4890

Gly Gly Gly Ile Gly Asp Glu Ile Glu Asp Pro Ala Gly Asp Glu
    4895            4900            4905

Tyr Glu Leu Tyr Arg Val Val Phe Asp Ile Thr Phe Phe Phe Phe
    4910            4915            4920

Val Ile Val Ile Leu Leu Ala Ile Ile Gln Gly Leu Ile Ile Asp
    4925            4930            4935

Ala Phe Gly Glu Leu Arg Asp Gln Gln Glu Gln Val Lys Glu Asp
    4940            4945            4950

Met Glu Thr Lys Cys Phe Ile Cys Gly Ile Gly Ser Asp Tyr Phe
    4955            4960            4965

Asp Thr Thr Pro His Gly Phe Glu Thr His Thr Leu Glu Glu His
    4970            4975            4980

Asn Leu Ala Asn Tyr Met Phe Phe Leu Met Tyr Leu Ile Asn Lys
    4985            4990            4995

Asp Glu Thr Glu His Thr Gly Gln Glu Ser Tyr Val Trp Lys Met
    5000            5005            5010

Tyr Gln Glu Arg Cys Trp Asp Phe Phe Pro Ala Gly Asp Cys Phe
    5015            5020            5025

Arg Lys Gln Tyr Glu Asp Gln Leu Ser
    5030            5035

<210> SEQ ID NO 5
<211> LENGTH: 4968
<212> TYPE: PRT
<213> ORGANISM: Oryctolagus cuniculus

<400> SEQUENCE: 5

Met Ala Asp Gly Gly Glu Gly Glu Asp Glu Ile Gln Phe Leu Arg Thr
1               5                   10                  15

Asp Asp Glu Val Val Leu Gln Cys Thr Ala Thr Ile His Lys Glu Gln
                20                  25                  30

Gln Lys Leu Cys Leu Ala Ala Glu Gly Phe Gly Asn Arg Leu Cys Phe
            35                  40                  45

Leu Glu Ser Thr Ser Asn Ser Lys Asn Val Pro Pro Asp Leu Ser Ile
        50                  55                  60

Cys Thr Phe Val Leu Glu Gln Ser Leu Ser Val Arg Ala Leu Gln Glu

-continued

```
             65                  70                  75                  80
Met Leu Ala Asn Thr Val Glu Lys Ser Glu Gly Gln Val Asp Val Glu
                    85                  90                  95
Lys Trp Lys Phe Met Met Lys Thr Ala Gln Gly Gly His Arg Thr
                100                 105                 110
Leu Leu Tyr Gly His Ala Ile Leu Leu Arg His Ser Tyr Ser Gly Met
                115                 120                 125
Tyr Leu Cys Cys Leu Ser Thr Ser Arg Ser Ser Thr Asp Lys Leu Ala
        130                 135                 140
Phe Asp Val Gly Leu Gln Glu Asp Thr Thr Gly Glu Ala Cys Trp Trp
145                 150                 155                 160
Thr Ile His Pro Ala Ser Lys Gln Arg Ser Glu Gly Glu Lys Val Arg
                    165                 170                 175
Val Gly Asp Asp Leu Ile Leu Val Ser Val Ser Ser Glu Arg Tyr Leu
                180                 185                 190
His Leu Ser Tyr Gly Asn Gly Ser Leu His Val Asp Ala Ala Phe Gln
            195                 200                 205
Gln Thr Leu Trp Ser Val Ala Pro Ile Ser Ser Gly Ser Glu Ala Ala
        210                 215                 220
Gln Gly Tyr Leu Ile Gly Gly Asp Val Leu Arg Leu Leu His Gly His
225                 230                 235                 240
Met Asp Glu Cys Leu Thr Val Pro Ser Gly Glu His Gly Glu Glu Gln
                    245                 250                 255
Arg Arg Thr Val His Tyr Glu Gly Gly Ala Val Ser Val His Ala Arg
                260                 265                 270
Ser Leu Trp Arg Leu Glu Thr Leu Arg Val Ala Trp Ser Gly Ser His
            275                 280                 285
Ile Arg Trp Gly Gln Pro Phe Arg Leu Arg His Val Thr Thr Gly Lys
        290                 295                 300
Tyr Leu Ser Leu Met Glu Asp Lys Asn Leu Leu Leu Met Asp Lys Glu
305                 310                 315                 320
Lys Ala Asp Val Lys Ser Thr Ala Phe Thr Phe Arg Ser Ser Lys Glu
                    325                 330                 335
Lys Leu Asp Gly Gly Val Arg Lys Glu Val Asp Gly Met Gly Thr Ser
                340                 345                 350
Glu Ile Lys Tyr Gly Asp Ser Ile Cys Tyr Ile Gln His Val Asp Thr
            355                 360                 365
Gly Leu Trp Leu Thr Tyr Gln Ser Val Asp Val Lys Ser Val Arg Met
        370                 375                 380
Gly Ser Ile Gln Arg Lys Ala Ile Met His His Glu Gly His Met Asp
385                 390                 395                 400
Asp Gly Leu Asn Leu Ser Arg Ser Gln His Glu Glu Ser Arg Thr Ala
                    405                 410                 415
Arg Val Ile Arg Ser Thr Val Phe Leu Phe Asn Arg Phe Ile Arg Gly
                420                 425                 430
Leu Asp Ala Leu Ser Lys Lys Ala Lys Ala Ser Ser Val Asp Leu Pro
            435                 440                 445
Ile Glu Ser Val Ser Leu Ser Leu Gln Asp Leu Ile Gly Tyr Phe His
        450                 455                 460
Pro Pro Asp Glu His Leu Glu His Glu Asp Lys Gln Asn Arg Leu Arg
465                 470                 475                 480
Ala Leu Lys Asn Arg Gln Asn Leu Phe Gln Glu Glu Gly Met Ile Asn
                    485                 490                 495
```

```
Leu Val Leu Glu Cys Ile Asp Arg Leu His Val Tyr Ser Ser Ala Ala
            500                 505                 510

His Phe Ala Asp Val Ala Gly Arg Glu Ala Gly Glu Ser Trp Lys Ser
            515                 520                 525

Ile Leu Asn Ser Leu Tyr Glu Leu Leu Ala Ala Leu Ile Arg Gly Asn
            530                 535                 540

Arg Lys Asn Cys Ala Gln Phe Ser Gly Ser Leu Asp Trp Leu Ile Ser
545                 550                 555                 560

Arg Leu Glu Arg Leu Glu Ala Ser Ser Gly Ile Leu Glu Val Leu His
                565                 570                 575

Cys Val Leu Val Glu Ser Pro Glu Ala Leu Asn Ile Ile Lys Glu Gly
            580                 585                 590

His Ile Lys Ser Ile Ile Ser Leu Leu Asp Lys His Gly Arg Asn His
            595                 600                 605

Lys Val Leu Asp Val Leu Cys Ser Leu Cys Val Cys His Gly Val Ala
            610                 615                 620

Val Arg Ser Asn Gln His Leu Ile Cys Asp Asn Leu Leu Pro Gly Arg
625                 630                 635                 640

Asp Leu Leu Leu Gln Thr Arg Leu Val Asn His Val Ser Ser Met Arg
                645                 650                 655

Pro Asn Ile Phe Leu Gly Val Ser Glu Gly Ser Ala Gln Tyr Lys Lys
            660                 665                 670

Trp Tyr Tyr Glu Leu Met Val Asp His Thr Glu Pro Phe Val Thr Ala
            675                 680                 685

Glu Ala Thr His Leu Arg Val Gly Trp Ala Ser Thr Glu Gly Tyr Ser
            690                 695                 700

Pro Tyr Pro Gly Gly Gly Glu Glu Trp Gly Gly Asn Gly Val Gly Asp
705                 710                 715                 720

Asp Leu Phe Ser Tyr Gly Phe Asp Gly Leu His Leu Trp Ser Gly Cys
                725                 730                 735

Ile Ala Arg Thr Val Ser Ser Pro Asn Gln His Leu Leu Arg Thr Asp
            740                 745                 750

Asp Val Ile Ser Cys Cys Leu Asp Leu Ser Ala Pro Ser Ile Ser Phe
            755                 760                 765

Arg Ile Asn Gly Gln Pro Val Gln Gly Met Phe Glu Asn Phe Asn Ile
            770                 775                 780

Asp Gly Leu Phe Phe Pro Val Val Ser Phe Ser Ala Gly Ile Lys Val
785                 790                 795                 800

Arg Phe Leu Leu Gly Gly Arg His Gly Glu Phe Lys Phe Leu Pro Pro
                805                 810                 815

Pro Gly Tyr Ala Pro Cys Tyr Glu Ala Val Leu Pro Lys Glu Lys Leu
            820                 825                 830

Lys Val Glu His Ser Arg Glu Tyr Lys Gln Glu Arg Thr Tyr Thr Arg
            835                 840                 845

Asp Leu Leu Gly Pro Thr Val Ser Leu Thr Gln Ala Ala Phe Thr Pro
850                 855                 860

Ile Pro Val Asp Thr Ser Gln Ile Val Leu Pro Pro His Leu Glu Arg
865                 870                 875                 880

Ile Arg Glu Lys Leu Ala Glu Asn Ile His Glu Leu Trp Val Met Asn
                885                 890                 895

Lys Ile Glu Leu Gly Trp Gln Tyr Gly Pro Val Arg Asp Asp Asn Lys
            900                 905                 910
```

```
Arg Gln His Pro Cys Leu Val Glu Phe Ser Lys Leu Pro Glu Gln Glu
        915                 920                 925

Arg Asn Tyr Asn Leu Gln Met Ser Leu Glu Thr Leu Lys Thr Leu Leu
        930                 935                 940

Ala Leu Gly Cys His Val Gly Ile Ser Asp His Ala Glu Glu Lys
945                 950                 955                 960

Val Lys Lys Met Lys Leu Pro Lys Asn Tyr Gln Leu Thr Ser Gly Tyr
                965                 970                 975

Lys Pro Ala Pro Met Asp Leu Ser Phe Ile Lys Leu Thr Pro Ser Gln
                980                 985                 990

Glu Ala Met Val Asp Lys Leu Ala Glu Asn Ala His Asn Val Trp Ala
        995                1000                1005

Arg Asp Arg Ile Arg Gln Gly Trp Thr Tyr Gly Ile Gln Gln Asp
        1010                1015                1020

Val Lys Asn Arg Arg Asn Pro Arg Leu Val Pro Tyr Thr Leu Leu
        1025                1030                1035

Asp Asp Arg Thr Lys Lys Ser Asn Lys Asp Ser Leu Arg Glu Ala
        1040                1045                1050

Val Arg Thr Leu Leu Gly Tyr Gly Tyr Asn Leu Glu Ala Pro Asp
        1055                1060                1065

Gln Asp His Ala Ala Arg Ala Glu Val Cys Ser Gly Thr Gly Glu
        1070                1075                1080

Arg Phe Arg Ile Phe Arg Ala Glu Lys Thr Tyr Ala Val Lys Ala
        1085                1090                1095

Gly Arg Trp Tyr Phe Glu Phe Glu Ala Val Thr Ser Gly Asp Met
        1100                1105                1110

Arg Val Gly Trp Ser Arg Pro Gly Cys Gln Pro Asp Gln Glu Leu
        1115                1120                1125

Gly Ser Asp Glu Arg Ala Phe Ala Phe Asp Gly Phe Lys Ala Gln
        1130                1135                1140

Arg Trp His Gln Gly Asn Glu His Tyr Gly Arg Ser Trp Gln Ala
        1145                1150                1155

Gly Asp Val Val Gly Cys Met Val Asp Met Asn Glu His Thr Met
        1160                1165                1170

Met Phe Thr Leu Asn Gly Glu Ile Leu Leu Asp Asp Ser Gly Ser
        1175                1180                1185

Glu Leu Ala Phe Lys Asp Phe Asp Val Gly Asp Gly Phe Ile Pro
        1190                1195                1200

Val Cys Ser Leu Gly Val Ala Gln Val Gly Arg Met Asn Phe Gly
        1205                1210                1215

Lys Asp Val Ser Thr Leu Lys Tyr Phe Thr Ile Cys Gly Leu Gln
        1220                1225                1230

Glu Gly Tyr Glu Pro Phe Ala Val Asn Thr Asn Arg Asp Ile Thr
        1235                1240                1245

Met Trp Leu Ser Lys Arg Leu Pro Gln Phe Leu Gln Val Pro Ser
        1250                1255                1260

Asn His Glu His Ile Glu Val Thr Arg Ile Asp Gly Thr Ile Asp
        1265                1270                1275

Ser Ser Pro Cys Leu Lys Val Thr Gln Lys Ser Phe Gly Ser Gln
        1280                1285                1290

Asn Ser Asn Thr Asp Ile Met Phe Tyr Arg Leu Ser Met Pro Ile
        1295                1300                1305

Glu Cys Ala Glu Val Phe Ser Lys Thr Val Pro Gly Gly Leu Pro
```

-continued

```
            1310                1315                1320
Gly Ala Gly Leu Phe Gly Pro Lys Asn Asp Leu Glu Asp Tyr Asp
1325                1330                1335
Ala Asp Ser Asp Phe Glu Val Leu Met Lys Thr Ala His Gly His
1340                1345                1350
Leu Val Pro Asp Arg Val Asp Lys Asp Lys Glu Thr Thr Lys Ala
1355                1360                1365
Glu Phe Asn Asn His Lys Asp Tyr Ala Gln Glu Lys Pro Ser Arg
1370                1375                1380
Leu Lys Gln Arg Phe Leu Arg Arg Thr Lys Pro Asp Tyr Ser
1385                1390                1395
Thr Ser His Ser Ala Arg Leu Thr Glu Asp Val Leu Ala Asp Asp
1400                1405                1410
Arg Asp Asp Tyr Asp Phe Leu Met Gln Thr Ser Thr Tyr Tyr Tyr
1415                1420                1425
Ser Val Arg Ile Phe Pro Gly Gln Glu Pro Ala Asn Val Trp Val
1430                1435                1440
Gly Trp Ile Thr Ser Asp Phe His Gln Tyr Asp Thr Gly Phe Asp
1445                1450                1455
Leu Asp Arg Val Arg Thr Val Thr Val Thr Leu Gly Asp Glu Lys
1460                1465                1470
Gly Lys Val His Glu Ser Ile Lys Arg Ser Asn Cys Tyr Met Val
1475                1480                1485
Cys Ala Gly Glu Ser Met Ser Pro Gly Gln Gly Arg Asn Asn Asn
1490                1495                1500
Gly Leu Glu Ile Gly Cys Val Val Asp Ala Ala Ser Gly Leu Leu
1505                1510                1515
Thr Phe Ile Ala Asn Gly Lys Glu Leu Ser Thr Tyr Tyr Gln Val
1520                1525                1530
Glu Pro Ser Thr Lys Leu Phe Pro Ala Val Phe Ala Gln Ala Thr
1535                1540                1545
Ser Pro Asn Val Phe Gln Phe Glu Leu Gly Arg Ile Lys Asn Val
1550                1555                1560
Met Pro Leu Ser Ala Gly Leu Phe Lys Ser Glu His Lys Asn Pro
1565                1570                1575
Val Pro Gln Cys Pro Pro Arg Leu His Val Gln Phe Leu Ser His
1580                1585                1590
Val Leu Trp Ser Arg Met Pro Asn Gln Phe Leu Lys Val Asp Val
1595                1600                1605
Ser Arg Ile Ser Glu Arg Gln Gly Trp Leu Val Gln Cys Leu Asp
1610                1615                1620
Pro Leu Gln Phe Met Ser Leu His Ile Pro Glu Glu Asn Arg Ser
1625                1630                1635
Val Asp Ile Leu Glu Leu Thr Glu Gln Glu Glu Leu Leu Lys Phe
1640                1645                1650
His Tyr His Thr Leu Arg Leu Tyr Ser Ala Val Cys Ala Leu Gly
1655                1660                1665
Asn His Arg Val Ala His Ala Leu Cys Ser His Val Asp Glu Pro
1670                1675                1680
Gln Leu Leu Tyr Ala Ile Glu Asn Lys Tyr Met Pro Gly Leu Leu
1685                1690                1695
Arg Thr Gly Tyr Tyr Asp Leu Leu Ile Asp Ile His Leu Ser Ser
1700                1705                1710
```

```
Tyr Ala Thr Ala Arg Leu Met Met Asn Asn Glu Phe Ile Val Pro
    1715            1720                1725

Met Thr Glu Glu Thr Lys Ser Ile Thr Leu Phe Pro Asp Glu Asn
    1730            1735                1740

Lys Lys His Gly Leu Pro Gly Ile Gly Leu Ser Thr Ser Leu Arg
    1745            1750                1755

Pro Arg Met Gln Phe Ser Ser Pro Ser Phe Val Ser Ile Asn Asn
    1760            1765                1770

Glu Cys Tyr Gln Tyr Ser Pro Glu Phe Pro Leu Asp Ile Leu Lys
    1775            1780                1785

Ala Lys Thr Ile Gln Met Leu Thr Glu Ala Val Lys Glu Gly Ser
    1790            1795                1800

Leu His Ala Arg Asp Pro Val Gly Gly Thr Thr Glu Phe Leu Phe
    1805            1810                1815

Val Pro Leu Ile Lys Leu Phe Tyr Thr Leu Leu Ile Met Gly Ile
    1820            1825                1830

Phe His Asn Glu Asp Leu Arg His Ile Leu Gln Leu Ile Glu Pro
    1835            1840                1845

Ser Val Phe Lys Asp Ala Ala Thr Pro Glu Glu Glu Gly Asp Thr
    1850            1855                1860

Leu Glu Glu Glu Pro Ser Val Glu Asp Thr Lys Leu Glu Gly Ala
    1865            1870                1875

Gly Glu Glu Glu Ala Lys Met Gly Lys Arg Pro Lys Glu Gly Leu
    1880            1885                1890

Leu Gln Met Lys Leu Pro Glu Pro Val Lys Leu Gln Met Cys Leu
    1895            1900                1905

Leu Leu Gln Tyr Leu Cys Asp Cys Gln Val Arg His Arg Ile Glu
    1910            1915                1920

Ala Ile Val Ala Phe Ser Asp Asp Phe Val Ala Lys Leu Gln Asp
    1925            1930                1935

Asn Gln Arg Phe Arg Tyr Asn Glu Val Met Gln Ala Leu Asn Met
    1940            1945                1950

Ser Ala Ala Leu Thr Ala Arg Lys Thr Lys Glu Phe Arg Ser Pro
    1955            1960                1965

Pro Gln Glu Gln Ile Asn Met Leu Leu Asn Phe Lys Asp Asp Lys
    1970            1975                1980

Ser Glu Cys Pro Cys Pro Glu Glu Ile Arg Asp Gln Leu Leu Asp
    1985            1990                1995

Phe His Glu Asp Leu Met Thr His Cys Gly Ile Glu Leu Asp Glu
    2000            2005                2010

Asp Gly Ser Leu Asp Gly Asn Ser Asp Leu Thr Ile Arg Gly Arg
    2015            2020                2025

Leu Leu Ser Leu Val Glu Lys Val Thr Tyr Leu Lys Lys Lys Gln
    2030            2035                2040

Thr Glu Lys Pro Val Glu Ser Asp Ser Arg Lys Ser Ser Thr Leu
    2045            2050                2055

Gln Gln Leu Ile Ser Glu Thr Met Val Arg Trp Ala Gln Glu Ser
    2060            2065                2070

Val Ile Glu Asp Pro Glu Leu Val Arg Ala Met Phe Val Leu Leu
    2075            2080                2085

His Arg Gln Tyr Asp Gly Ile Gly Gly Leu Val Arg Ala Leu Pro
    2090            2095                2100
```

-continued

| | | | | | | | | | |
|---|---|---|---|---|---|---|---|---|---|
| Lys | Thr | Tyr | Thr | Ile | Asn | Gly | Val | Ser | Val | Glu | Asp | Thr | Ile | Asn |
| | | | | 2105 | | | 2110 | | | | 2115 | | | |
| Leu | Leu | Ala | Ser | Leu | Gly | Gln | Ile | Arg | Ser | Leu | Leu | Ser | Val | Arg |
| 2120 | | | | | 2125 | | | | 2130 | | | | | |
| Met | Gly | Lys | Glu | Glu | Lys | Leu | Met | Ile | Arg | Gly | Leu | Gly | Asp |
| 2135 | | | | | 2140 | | | | 2145 | | | | |
| Ile | Met | Asn | Asn | Lys | Val | Phe | Tyr | Gln | His | Pro | Asn | Leu | Met | Arg |
| 2150 | | | | | 2155 | | | | 2160 | | | | | |

Lys Thr Tyr Thr Ile Asn Gly Val Ser Val Glu Asp Thr Ile Asn
                    2105            2110              2115

Leu Leu Ala Ser Leu Gly Gln Ile Arg Ser Leu Leu Ser Val Arg
2120                2125                2130

Met Gly Lys Glu Glu Lys Leu Met Ile Arg Gly Leu Gly Asp
2135                2140                2145

Ile Met Asn Asn Lys Val Phe Tyr Gln His Pro Asn Leu Met Arg
2150                2155                2160

Ala Leu Gly Met His Glu Thr Val Met Glu Val Met Val Asn Val
2165                2170                2175

Leu Gly Gly Gly Glu Ser Lys Glu Ile Thr Phe Pro Lys Met Val
2180                2185                2190

Ala Asn Cys Cys Arg Phe Leu Cys Tyr Phe Cys Arg Ile Ser Arg
2195                2200                2205

Gln Asn Gln Lys Ala Met Phe Asp His Leu Ser Tyr Leu Leu Glu
2210                2215                2220

Asn Ser Ser Val Gly Leu Ala Ser Pro Ala Met Arg Gly Ser Thr
2225                2230                2235

Pro Leu Asp Val Ala Ala Ala Ser Val Met Asp Asn Asn Glu Leu
2240                2245                2250

Ala Leu Ala Leu Arg Glu Pro Asp Leu Glu Lys Val Val Arg Tyr
2255                2260                2265

Leu Ala Gly Cys Gly Leu Gln Ser Cys Gln Met Leu Val Ser Lys
2270                2275                2280

Gly Tyr Pro Asp Ile Gly Trp Asn Pro Val Glu Gly Glu Arg Tyr
2285                2290                2295

Leu Asp Phe Leu Arg Phe Ala Val Phe Cys Asn Gly Glu Ser Val
2300                2305                2310

Glu Glu Asn Ala Asn Val Val Val Arg Leu Leu Ile Arg Arg Pro
2315                2320                2325

Glu Cys Phe Gly Pro Ala Leu Arg Gly Glu Gly Gly Asn Gly Leu
2330                2335                2340

Leu Ala Ala Met Glu Glu Ala Ile Lys Ile Ala Glu Asp Pro Ser
2345                2350                2355

Arg Asp Gly Pro Ser Pro Thr Ser Gly Ser Ser Lys Thr Leu Asp
2360                2365                2370

Thr Glu Glu Glu Asp Asp Thr Ile His Met Gly Asn Ala Ile
2375                2380                2385

Met Thr Phe Tyr Ala Ala Leu Ile Asp Leu Leu Gly Arg Cys Ala
2390                2395                2400

Pro Glu Met His Leu Ile His Ala Gly Lys Gly Glu Ala Ile Arg
2405                2410                2415

Ile Arg Ser Ile Leu Arg Ser Leu Ile Pro Leu Gly Asp Leu Val
2420                2425                2430

Gly Val Ile Ser Ile Ala Phe Gln Met Pro Thr Ile Ala Lys Asp
2435                2440                2445

Gly Asn Val Val Glu Pro Asp Met Ser Ala Gly Phe Cys Pro Asp
2450                2455                2460

His Lys Ala Ala Met Val Leu Phe Leu Asp Arg Val Tyr Gly Ile
2465                2470                2475

Glu Val Gln Asp Phe Leu Leu His Leu Leu Glu Val Gly Phe Leu
2480                2485                2490

Pro Asp Leu Arg Ala Ala Ala Ser Leu Asp Thr Ala Ala Leu Ser

-continued

```
              2495                2500                 2505
    Ala Thr Asp Met Ala Leu Ala  Leu Asn Arg Tyr Leu  Cys Thr Ala
              2510                2515                 2520
    Val Leu Pro Leu Leu Thr Arg  Cys Ala Pro Leu Phe  Ala Gly Thr
              2525                2530                 2535
    Glu His His Ala Ser Leu Ile  Asp Ser Leu Leu His  Thr Val Tyr
              2540                2545                 2550
    Arg Leu Ser Lys Gly Cys Ser  Leu Thr Lys Ala Gln  Arg Asp Ser
              2555                2560                 2565
    Ile Glu Val Cys Leu Leu Ser  Ile Cys Gly Gln Leu  Arg Pro Ser
              2570                2575                 2580
    Met Met Gln His Leu Leu Arg  Arg Leu Val Phe Asp  Val Pro Leu
              2585                2590                 2595
    Leu Asn Glu His Ala Lys Met  Pro Leu Lys Leu Leu  Thr Asn His
              2600                2605                 2610
    Tyr Glu Arg Cys Trp Lys Tyr  Tyr Cys Leu Pro Gly  Gly Trp Gly
              2615                2620                 2625
    Asn Phe Gly Ala Ala Ser Glu  Glu Glu Leu His Leu  Ser Arg Lys
              2630                2635                 2640
    Leu Phe Trp Gly Ile Phe Asp  Ala Leu Ser Gln Lys  Lys Tyr Glu
              2645                2650                 2655
    Gln Glu Leu Phe Lys Leu Ala  Leu Pro Cys Leu Ser  Ala Val Ala
              2660                2665                 2670
    Gly Ala Leu Pro Pro Asp Tyr  Met Glu Ser Asn Tyr  Val Ser Met
              2675                2680                 2685
    Met Glu Lys Gln Ser Ser Met  Asp Ser Glu Gly Asn  Phe Asn Pro
              2690                2695                 2700
    Gln Pro Val Asp Thr Ser Asn  Ile Ile Pro Glu Lys  Leu Glu
              2705                2710                 2715
    Tyr Phe Ile Asn Lys Tyr Ala  Glu His Ser His Asp  Lys Trp Ser
              2720                2725                 2730
    Met Asp Lys Leu Ala Asn Gly  Trp Ile Tyr Gly Glu  Ile Tyr Ser
              2735                2740                 2745
    Asp Ser Ser Lys Ile Gln Pro  Leu Met Lys Pro Tyr  Lys Leu Leu
              2750                2755                 2760
    Ser Glu Lys Glu Lys Glu Ile  Tyr Arg Trp Pro Ile  Lys Glu Ser
              2765                2770                 2775
    Leu Lys Thr Met Leu Ala Trp  Gly Trp Arg Ile Glu  Arg Thr Arg
              2780                2785                 2790
    Glu Gly Asp Ser Met Ala Leu  Tyr Asn Arg Thr Arg  Arg Ile Ser
              2795                2800                 2805
    Gln Thr Ser Gln Val Ser Val  Asp Ala Ala His Gly  Tyr Ser Pro
              2810                2815                 2820
    Arg Ala Ile Asp Met Ser Asn  Val Thr Leu Ser Arg  Asp Leu His
              2825                2830                 2835
    Ala Met Ala Glu Met Met Ala  Glu Asn Tyr His Asn  Ile Trp Ala
              2840                2845                 2850
    Lys Lys Lys Lys Leu Glu Leu  Glu Ser Lys Gly Gly  Gly Asn His
              2855                2860                 2865
    Pro Leu Leu Val Pro Tyr Asp  Thr Leu Thr Ala Lys  Glu Lys Ala
              2870                2875                 2880
    Lys Asp Arg Glu Lys Ala Gln  Asp Ile Leu Lys Phe  Leu Gln Ile
              2885                2890                 2895
```

-continued

```
Asn Gly Tyr Ala Val Ser Arg Gly Phe Lys Asp Leu Glu Leu Asp
    2900            2905            2910

Thr Pro Ser Ile Glu Lys Arg Phe Ala Tyr Ser Phe Leu Gln Gln
    2915            2920            2925

Leu Ile Arg Tyr Val Asp Glu Ala His Gln Tyr Ile Leu Glu Phe
    2930            2935            2940

Asp Gly Gly Ser Arg Ser Lys Gly Glu His Phe Pro Tyr Glu Gln
    2945            2950            2955

Glu Ile Lys Phe Phe Ala Lys Val Val Leu Pro Leu Ile Asp Gln
    2960            2965            2970

Tyr Phe Lys Asn His Arg Leu Tyr Phe Leu Ser Ala Ala Ser Arg
    2975            2980            2985

Pro Leu Cys Ser Gly Gly His Ala Ser Asn Lys Glu Lys Glu Met
    2990            2995            3000

Val Thr Ser Leu Phe Cys Lys Leu Gly Val Leu Val Arg His Arg
    3005            3010            3015

Ile Ser Leu Phe Gly Asn Asp Ala Thr Ser Ile Val Asn Cys Leu
    3020            3025            3030

His Ile Leu Gly Gln Thr Leu Asp Ala Arg Thr Val Met Lys Thr
    3035            3040            3045

Gly Leu Glu Ser Val Lys Ser Ala Leu Arg Ala Phe Leu Asp Asn
    3050            3055            3060

Ala Ala Glu Asp Leu Glu Lys Thr Met Glu Asn Leu Lys Gln Gly
    3065            3070            3075

Gln Phe Thr His Thr Arg Asn Gln Pro Arg Gly Val Thr Gln Ile
    3080            3085            3090

Ile Asn Tyr Thr Thr Val Ala Leu Leu Pro Met Leu Ser Ser Leu
    3095            3100            3105

Phe Glu His Ile Gly Gln His Gln Phe Gly Glu Asp Leu Ile Leu
    3110            3115            3120

Glu Asp Val Gln Val Ser Cys Tyr Arg Ile Leu Thr Ser Leu Tyr
    3125            3130            3135

Ala Leu Gly Thr Ser Lys Ser Ile Tyr Val Glu Arg Gln Arg Ser
    3140            3145            3150

Ala Leu Gly Glu Cys Leu Ala Ala Phe Ala Gly Ala Phe Pro Val
    3155            3160            3165

Ala Phe Leu Glu Thr His Leu Asn Lys His Asn Ile Tyr Ser Ile
    3170            3175            3180

Tyr Asn Thr Lys Ser Ser Arg Glu Arg Ala Ala Leu Ser Leu Pro
    3185            3190            3195

Ala Asn Val Glu Asp Val Cys Pro Asn Ile Pro Ser Leu Glu Lys
    3200            3205            3210

Leu Met Glu Glu Ile Val Glu Leu Ala Glu Ser Gly Ile Arg Tyr
    3215            3220            3225

Thr Gln Met Pro His Val Met Glu Val Ile Leu Pro Met Leu Cys
    3230            3235            3240

Ser Tyr Met Ser Arg Trp Trp Glu His Gly Pro Glu Ser Asn Pro
    3245            3250            3255

Gly Arg Ala Glu Met Cys Cys Thr Ala Leu Asn Ser Glu His Met
    3260            3265            3270

Asn Thr Leu Leu Gly Asn Ile Leu Lys Ile Ile Tyr Asn Asn Leu
    3275            3280            3285
```

-continued

```
Gly Ile Asp Glu Gly Ala Trp Met Lys Arg Leu Ala Val Phe Ser
    3290            3295            3300
Gln Pro Ile Ile Asn Lys Val Lys Pro Gln Leu Leu Lys Thr His
    3305            3310            3315
Phe Leu Pro Leu Met Glu Lys Leu Lys Lys Lys Ala Ala Met Val
    3320            3325            3330
Val Ser Glu Glu Asp His Leu Lys Ala Glu Ala Arg Gly Asp Met
    3335            3340            3345
Ser Glu Ala Glu Leu Leu Ile Leu Asp Glu Phe Thr Thr Leu Ala
    3350            3355            3360
Arg Asp Leu Tyr Ala Phe Tyr Pro Leu Leu Ile Arg Phe Val Asp
    3365            3370            3375
Tyr Asn Arg Ala Lys Trp Leu Lys Glu Pro Thr Pro Glu Ala Glu
    3380            3385            3390
Glu Leu Phe Arg Met Val Ala Glu Val Phe Ile Tyr Trp Ser Lys
    3395            3400            3405
Ser His Asn Phe Lys Arg Glu Glu Gln Asn Phe Val Val Gln Asn
    3410            3415            3420
Glu Ile Asn Asn Met Ser Phe Leu Ile Thr Asp Thr Lys Ser Lys
    3425            3430            3435
Met Ser Lys Ala Ala Val Ser Asp Gln Glu Arg Lys Lys Met Lys
    3440            3445            3450
Arg Lys Gly Asp Arg Tyr Ser Met Gln Thr Ser Leu Ile Val Ala
    3455            3460            3465
Ala Leu Lys Arg Leu Leu Pro Ile Gly Leu Asn Ile Cys Ala Pro
    3470            3475            3480
Gly Asp Gln Glu Leu Ile Ala Leu Ala Lys Asn Arg Phe Ser Leu
    3485            3490            3495
Lys Asp Thr Glu Asp Glu Val Arg Asp Ile Ile Arg Asn Asn Ile
    3500            3505            3510
His Leu Gln Gly Lys Leu Glu Asp Pro Ala Ile Arg Trp Gln Met
    3515            3520            3525
Ala Leu Tyr Lys Asp Leu Pro Asn Arg Thr Glu Glu Thr Ser Asp
    3530            3535            3540
Pro Glu Lys Thr Val Glu Arg Val Leu Asp Ile Ala Asn Val Leu
    3545            3550            3555
Phe His Leu Glu Gln Lys Ser Lys Phe Ile Gly Arg Arg Tyr Tyr
    3560            3565            3570
Asn Leu Val Glu His Pro Gln Arg Ser Lys Lys Ala Val Trp His
    3575            3580            3585
Lys Leu Leu Ser Lys Gln Arg Lys Arg Ala Val Val Ala Cys Phe
    3590            3595            3600
Arg Met Ala Pro Leu Tyr Asn Leu Pro Arg His Arg Ala Val Asn
    3605            3610            3615
Leu Phe Leu Gln Gly Tyr Glu Lys Ser Trp Ile Glu Thr Glu Glu
    3620            3625            3630
His Tyr Phe Glu Asp Lys Leu Ile Glu Asp Leu Ala Lys Pro Gly
    3635            3640            3645
Ala Glu Pro Pro Glu Glu Asp Glu Val Thr Lys Arg Val Asp Pro
    3650            3655            3660
Leu His Gln Leu Ile Leu Leu Phe Ser Arg Thr Ala Leu Thr Glu
    3665            3670            3675
Lys Cys Lys Leu Glu Glu Asp Phe Leu Tyr Met Ala Tyr Ala Asp
```

-continued

|  | 3680 |  |  |  | 3685 |  |  |  | 3690 |  |  |
|---|---|---|---|---|---|---|---|---|---|---|---|
| Ile | Met | Ala | Lys | Ser | Cys | His | Asp | Glu | Glu | Asp | Asp | Gly | Glu |
|  | 3695 |  |  |  | 3700 |  |  |  | 3705 |  |  |

Glu Glu Val Lys Ser Phe Glu Glu Lys Glu Met Glu Lys Gln Lys
    3710                3715                3720

Leu Leu Tyr Gln Gln Ala Arg Leu His Asp Arg Gly Ala Ala Glu
    3725                3730                3735

Met Val Leu Gln Thr Ile Ser Ala Ser Lys Gly Glu Thr Gly Pro
    3740                3745                3750

Met Val Ala Ala Thr Leu Lys Leu Gly Ile Ala Ile Leu Asn Gly
    3755                3760                3765

Gly Asn Ser Thr Val Gln Gln Lys Met Leu Asp Tyr Leu Lys Glu
    3770                3775                3780

Lys Lys Asp Val Gly Phe Phe Gln Ser Leu Ala Gly Leu Met Gln
    3785                3790                3795

Ser Cys Ser Val Leu Asp Leu Asn Ala Phe Glu Arg Gln Asn Lys
    3800                3805                3810

Ala Glu Gly Leu Gly Met Val Thr Glu Glu Gly Ser Gly Glu Lys
    3815                3820                3825

Val Leu Gln Asp Asp Glu Phe Thr Cys Asp Leu Phe Arg Phe Leu
    3830                3835                3840

Gln Leu Leu Cys Glu Gly His Asn Ser Asp Phe Gln Asn Tyr Leu
    3845                3850                3855

Arg Thr Gln Thr Gly Asn Asn Thr Thr Val Asn Ile Ile Ile Ser
    3860                3865                3870

Thr Val Asp Tyr Leu Leu Arg Val Gln Glu Ser Ile Ser Asp Phe
    3875                3880                3885

Tyr Trp Tyr Tyr Ser Gly Lys Asp Val Ile Asp Glu Gln Gly Gln
    3890                3895                3900

Arg Asn Phe Ser Lys Ala Ile Gln Val Ala Lys Gln Val Phe Asn
    3905                3910                3915

Thr Leu Thr Glu Tyr Ile Gln Gly Pro Cys Thr Gly Asn Gln Gln
    3920                3925                3930

Ser Leu Ala His Ser Arg Leu Trp Asp Ala Val Val Gly Phe Leu
    3935                3940                3945

His Val Phe Ala His Met Gln Met Lys Leu Ser Gln Asp Ser Ser
    3950                3955                3960

Gln Ile Glu Leu Leu Lys Glu Leu Met Asp Leu Gln Lys Asp Met
    3965                3970                3975

Val Val Met Leu Leu Ser Met Leu Glu Gly Asn Val Val Asn Gly
    3980                3985                3990

Thr Ile Gly Lys Gln Met Val Asp Met Leu Val Glu Ser Ser Asn
    3995                4000                4005

Asn Val Glu Met Ile Leu Lys Phe Phe Asp Met Phe Leu Lys Leu
    4010                4015                4020

Lys Asp Leu Thr Ser Ser Asp Thr Phe Lys Glu Tyr Asp Pro Asp
    4025                4030                4035

Gly Lys Gly Ile Ile Ser Lys Arg Asp Phe His Lys Ala Met Glu
    4040                4045                4050

Ser His Lys His Tyr Thr Gln Ser Glu Thr Glu Phe Leu Leu Ser
    4055                4060                4065

Cys Ala Glu Thr Asp Glu Asn Glu Thr Leu Asp Tyr Glu Glu Phe
    4070                4075                4080

-continued

```
Val Lys Arg Phe His Glu Pro Ala Lys Asp Ile Gly Phe Asn Val
4085                4090                4095

Ala Val Leu Leu Thr Asn Leu Ser Glu His Met Pro Asn Glu Thr
4100                4105                4110

Arg Leu Gln Thr Phe Leu Glu Leu Ala Glu Ser Val Leu Asn Tyr
4115                4120                4125

Phe Gln Pro Phe Leu Gly Arg Ile Glu Ile Met Gly Ser Ala Lys
4130                4135                4140

Arg Ile Glu Arg Val Tyr Phe Glu Ile Ser Glu Ser Ser Arg Thr
4145                4150                4155

Gln Trp Glu Lys Pro Gln Val Lys Glu Ser Lys Arg Gln Phe Ile
4160                4165                4170

Phe Asp Val Val Asn Glu Gly Gly Glu Lys Glu Lys Met Glu Leu
4175                4180                4185

Phe Val Asn Phe Cys Glu Asp Thr Ile Phe Glu Met Gln Leu Ala
4190                4195                4200

Ala Gln Ile Ser Glu Ser Asp Leu Asn Glu Arg Ser Ala Asn Lys
4205                4210                4215

Glu Glu Ser Glu Lys Glu Arg Pro Glu Glu Gln Gly Pro Lys Met
4220                4225                4230

Gly Phe Phe Ser Val Leu Thr Val Arg Ser Ala Leu Phe Ala Leu
4235                4240                4245

Arg Tyr Asn Ile Leu Thr Leu Met Arg Met Leu Ser Leu Lys Ser
4250                4255                4260

Leu Lys Lys Gln Met Lys Lys Met Lys Lys Met Thr Val Lys Asp
4265                4270                4275

Met Val Thr Ala Phe Phe Ser Ser Tyr Trp Ser Ile Phe Met Thr
4280                4285                4290

Leu Leu His Phe Val Ala Ser Val Phe Arg Gly Phe Phe Arg Ile
4295                4300                4305

Val Cys Ser Leu Leu Leu Gly Gly Ser Leu Val Glu Gly Ala Lys
4310                4315                4320

Lys Ile Lys Val Ala Glu Leu Leu Ala Asn Met Pro Asp Pro Thr
4325                4330                4335

Gln Asp Glu Val Arg Gly Asp Gly Glu Glu Gly Glu Arg Lys Pro
4340                4345                4350

Met Glu Thr Thr Leu Pro Ser Glu Asp Leu Thr Asp Leu Lys Glu
4355                4360                4365

Leu Thr Glu Glu Ser Asp Leu Leu Ser Asp Ile Phe Gly Leu Asp
4370                4375                4380

Leu Lys Arg Glu Gly Gly Gln Tyr Lys Leu Ile Pro His Asn Pro
4385                4390                4395

Asn Ala Gly Leu Ser Asp Leu Met Ser Asn Pro Val Leu Ile Pro
4400                4405                4410

Glu Glu Gln Glu Lys Phe Gln Glu Gln Lys Thr Lys Glu Glu Glu
4415                4420                4425

Lys Glu Glu Lys Glu Glu Thr Lys Ser Glu Pro Glu Lys Ala Glu
4430                4435                4440

Gly Glu Asp Gly Glu Lys Glu Glu Lys Val Lys Glu Asp Lys Gly
4445                4450                4455

Lys Gln Lys Leu Arg Gln Leu His Thr His Arg Tyr Gly Glu Pro
4460                4465                4470
```

-continued

| | | | | | | | | | | |
|---|---|---|---|---|---|---|---|---|---|---|
| Glu | Val | Pro | Glu | Ser | Ala | Phe | Trp | Lys | Lys | Ile | Ile | Ala | Tyr | Gln |
| 4475 | | | | 4480 | | | | | 4485 | | | | | |
| Gln | Lys | Leu | Leu | Asn | Tyr | Phe | Ala | Arg | Asn | Phe | Tyr | Asn | Met | Arg |
| 4490 | | | | | 4495 | | | | | 4500 | | | | |
| Met | Leu | Ala | Leu | Phe | Val | Ala | Phe | Ala | Ile | Asn | Phe | Ile | Leu | Leu |
| 4505 | | | | | 4510 | | | | | 4515 | | | | |
| Phe | Tyr | Lys | Val | Ser | Thr | Ser | Ser | Val | Val | Glu | Gly | Lys | Glu | Leu |
| 4520 | | | | | 4525 | | | | | 4530 | | | | |
| Pro | Ser | Arg | Ser | Thr | Ser | Glu | Asn | Ala | Lys | Val | Thr | Thr | Ser | Leu |
| 4535 | | | | | 4540 | | | | | 4545 | | | | |
| Asp | Ser | Ser | Ser | His | Arg | Ile | Ile | Ala | Val | His | Tyr | Val | Leu | Glu |
| 4550 | | | | | 4555 | | | | | 4560 | | | | |
| Glu | Ser | Ser | Gly | Tyr | Met | Glu | Pro | Thr | Leu | Arg | Ile | Leu | Ala | Ile |
| 4565 | | | | | 4570 | | | | | 4575 | | | | |
| Leu | His | Thr | Val | Ile | Ser | Phe | Phe | Cys | Ile | Ile | Gly | Tyr | Tyr | Cys |
| 4580 | | | | | 4585 | | | | | 4590 | | | | |
| Leu | Lys | Val | Pro | Leu | Val | Ile | Phe | Lys | Arg | Glu | Lys | Glu | Val | Ala |
| 4595 | | | | | 4600 | | | | | 4605 | | | | |
| Arg | Lys | Leu | Glu | Phe | Asp | Gly | Leu | Tyr | Ile | Thr | Glu | Gln | Pro | Ser |
| 4610 | | | | | 4615 | | | | | 4620 | | | | |
| Glu | Asp | Asp | Ile | Lys | Gly | Gln | Trp | Asp | Arg | Leu | Val | Ile | Asn | Thr |
| 4625 | | | | | 4630 | | | | | 4635 | | | | |
| Gln | Ser | Phe | Pro | Asn | Asn | Tyr | Trp | Asp | Lys | Phe | Val | Lys | Arg | Lys |
| 4640 | | | | | 4645 | | | | | 4650 | | | | |
| Val | Met | Asp | Lys | Tyr | Gly | Glu | Phe | Tyr | Gly | Arg | Asp | Arg | Ile | Ser |
| 4655 | | | | | 4660 | | | | | 4665 | | | | |
| Glu | Leu | Leu | Gly | Met | Asp | Lys | Ala | Ala | Leu | Asp | Phe | Ser | Asp | Ala |
| 4670 | | | | | 4675 | | | | | 4680 | | | | |
| Arg | Glu | Lys | Lys | Lys | Pro | Lys | Lys | Asp | Ser | Ser | Leu | Ser | Ala | Val |
| 4685 | | | | | 4690 | | | | | 4695 | | | | |
| Leu | Asn | Ser | Ile | Asp | Val | Lys | Tyr | Gln | Met | Trp | Lys | Leu | Gly | Val |
| 4700 | | | | | 4705 | | | | | 4710 | | | | |
| Val | Phe | Thr | Asp | Asn | Ser | Phe | Leu | Tyr | Leu | Ala | Trp | Tyr | Met | Thr |
| 4715 | | | | | 4720 | | | | | 4725 | | | | |
| Met | Ser | Ile | Leu | Gly | His | Tyr | Asn | Asn | Phe | Phe | Phe | Ala | Ala | His |
| 4730 | | | | | 4735 | | | | | 4740 | | | | |
| Leu | Leu | Asp | Ile | Ala | Met | Gly | Phe | Lys | Thr | Leu | Arg | Thr | Ile | Leu |
| 4745 | | | | | 4750 | | | | | 4755 | | | | |
| Ser | Ser | Val | Thr | His | Asn | Gly | Lys | Gln | Leu | Val | Leu | Thr | Val | Gly |
| 4760 | | | | | 4765 | | | | | 4770 | | | | |
| Leu | Leu | Ala | Val | Val | Val | Tyr | Leu | Tyr | Thr | Val | Val | Ala | Phe | Asn |
| 4775 | | | | | 4780 | | | | | 4785 | | | | |
| Phe | Phe | Arg | Lys | Phe | Tyr | Asn | Lys | Ser | Glu | Asp | Gly | Asp | Thr | Pro |
| 4790 | | | | | 4795 | | | | | 4800 | | | | |
| Asp | Met | Lys | Cys | Asp | Asp | Met | Leu | Thr | Cys | Tyr | Met | Phe | His | Met |
| 4805 | | | | | 4810 | | | | | 4815 | | | | |
| Tyr | Val | Gly | Val | Arg | Ala | Gly | Gly | Gly | Ile | Gly | Asp | Glu | Ile | Glu |
| 4820 | | | | | 4825 | | | | | 4830 | | | | |
| Asp | Pro | Ala | Gly | Asp | Glu | Tyr | Glu | Ile | Tyr | Arg | Ile | Ile | Phe | Asp |
| 4835 | | | | | 4840 | | | | | 4845 | | | | |
| Ile | Thr | Phe | Phe | Phe | Phe | Val | Ile | Val | Ile | Leu | Leu | Ala | Ile | Ile |
| 4850 | | | | | 4855 | | | | | 4860 | | | | |
| Gln | Gly | Leu | Ile | Ile | Asp | Ala | Phe | Gly | Glu | Leu | Arg | Asp | Gln | Gln |

-continued

```
                    4865               4870               4875

Glu Gln Val Lys Glu Asp Met Glu Thr Lys Cys Phe Ile Cys Gly
        4880               4885               4890

Ile Gly Asn Asp Tyr Phe Asp Thr Val Pro His Gly Phe Glu Thr
    4895               4900               4905

His Thr Leu Gln Glu His Asn Leu Ala Asn Tyr Leu Phe Phe Leu
        4910               4915               4920

Met Tyr Leu Ile Asn Lys Asp Glu Thr Glu His Thr Gly Gln Glu
    4925               4930               4935

Ser Tyr Val Trp Lys Met Tyr Gln Glu Arg Cys Trp Glu Phe Phe
        4940               4945               4950

Pro Ala Gly Asp Cys Phe Arg Lys Gln Tyr Glu Asp Gln Leu Asn
    4955               4960               4965

<210> SEQ ID NO 6
<211> LENGTH: 9
<212> TYPE: DNA
<213> ORGANISM: Homo sapiens

<400> SEQUENCE: 6 gagccatgg                                                               9

<210> SEQ ID NO 7
<211> LENGTH: 10
<212> TYPE: DNA
<213> ORGANISM: Homo sapiens

<400> SEQUENCE: 7
ccagccatgg                                                              10

<210> SEQ ID NO 8
<211> LENGTH: 25
<212> TYPE: DNA
<213> ORGANISM: Artificial Sequence
<220> FEATURE:
<223> OTHER INFORMATION: oligonucleotide

<400> SEQUENCE: 8
agtggataaa cttgcagaaa atgca                                             25

<210> SEQ ID NO 9
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 9
tggggagctg ctgatcacca ataaa                                             25

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
ttgatgaatc tggacagcac                                                   20

<210> SEQ ID NO 11
<211> LENGTH: 20
```

```
-continued

<212> TYPE: DNA
<213> ORGANISM: Artificial Sequence
<220> FEATURE:
<223> OTHER INFORMATION: oligonucleotide primer

<400> SEQUENCE: 11
acgtgttaga aattgcgggt                                              20
```

HUMAN TYPE 3 RYANODINE RECEPTOR PROTEIN AND DNA MOLECULES CODING THEREFOR

CROSS-REFERENCE TO RELATED APPLICATIONS

This application is the National Stage of International Application No. PCT/EP98/02926 filed May 18, 1998, which claims priority to German Patent Application No. 197 22 317.6, filed May 28, 1997.

BACKGROUND OF THE INVENTION

The invention relates to nucleic acids and protein of the type 3 human ryanodine receptor (hRyR3), chimeric ryanodine receptors with parts of the human receptor and processes for preparing these proteins. The invention further relates to the detection of ryanodine receptors in human tissues for diagnosing pathological conditions and methods of identifying activators or inhibitors of hRyR3.

Cytoplasmic calcium plays an important part in cell activation, the release of neurotransmitters, muscle contraction and other biological processes. It is increased by the effect of extracellular calcium resulting from voltage-activated and other ion channels and by the calcium release from intracellular supplies. At present, two intracellular calcium release channels are known, the inositol 1,4,5-triphosphate receptors (IP3R) and the ryanodine receptors (RyR). The release of calcium by IP3R starts from a ubiquitous mechanism which has been described for numerous cells. By contrast, three types of RyR-mRNA, namely RyR1, RyR2 and RyR3 are expressed tissue-specifically; RyR1 primarily in the skeletal muscle, RyR2 in the heart muscle and brain and RyR3 in the brain and smooth muscle. In the brain, the RyR3 is strongly expressed only in very limited areas such as the hippocampus, Nucleus caudatus, Corpus callosum and thalamus. The RyR3 is also expressed in non-excitable cells such as human T-lymphocytes. It has been postulated that RyR3 has a part to play in cell proliferation (Hakamata, Y. et al. FEBS Lett., 352 (1994), 206–210). For RyR1 and RyR2 it has been shown that, in the excitation contraction coupling of skeletal and heart muscle, voltage-activated calcium channels activate the RyR1 in the skeletal muscle and presumably also in neurones directly, whereas the calcium of the voltage-activated channels is a trigger for the opening of RyR2 in heart muscle (calcium-induced release of calcium). The function of RyR3 is subject to a series of speculations. Although calcium appears to be an important physiological ligand of RyR3, there are some indications that the calcium-induced release of calcium differs from that of other RyR. It is assumed that an endogenous RyR3 is responsible for the substantially lower calcium sensitivity of the remaining calcium release activity of RyR1-deficient murine muscle cells. RyR3 is demonstrably insensitive to caffeine in some cases, caffeine being the substance primarily used for RyR activation. Since RyR3 is expressed in non-excitable cells which have virtually no voltage activated calcium channels, it appears possible that RyR3 is regulated by different mechanism from the other RyR. RyR3-deficient mutant mice exhibit increased locomotor activity. The cDNA sequences of RyR1, RyR2 and for rabbit-RyR3 (rRyR3) are already known whereas the nucleic acid sequence of RyR3 in humans (hRyR3) has not yet been investigated.

In spite of a plethora of bits of information regarding RyR3, its molecular physiological properties, its significance in pathological conditions and methods of evaluating possible inhibitors and activators of its activity are substantially or even totally unknown. In addition, the transfer of the currently available information from tests with isolated RyR3 of non-human origin to humans is accompanied by considerable uncertainty.

BRIEF DESCRIPTION OF THE DRAWINGS

FIG. 1 compares the amino acid sequence of the RyR isoforms by aligning the derived amino acid sequence of human RyR3 (SEQ ID NO: 2) (at the top) with rabbit RyR3 (SEQ ID NO: 3) (upper middle), rabbit RyR1 (SEQ ID NO: 4) (lower middle) and rabbit RyR2 (SEQ ID NO: 5) (bottom). Four identical groups in the same position are framed with solid lines whereas sequences of four identical or conserved groups are framed with broken lines. The amino groups are numbered, starting from the initiating methionine. The presumed transmembrane segments M1 to M4 are shown; the ends of each segment were determined by comparison with rabbit RyR3. Four repeating sequences which occur in tandem pairs are indicated by arrows.

FIG. 2 shows the reaction of chimeric human RyR3 in dyspedic myotubes from RyR1-deficient (dyspedic) mice to caffeine.

A, diagrammatic representation of the structure of chimeric RyR from rabbit RyR2 (open rectangle) and human RyR3 (solid rectangle).

Figure 3:
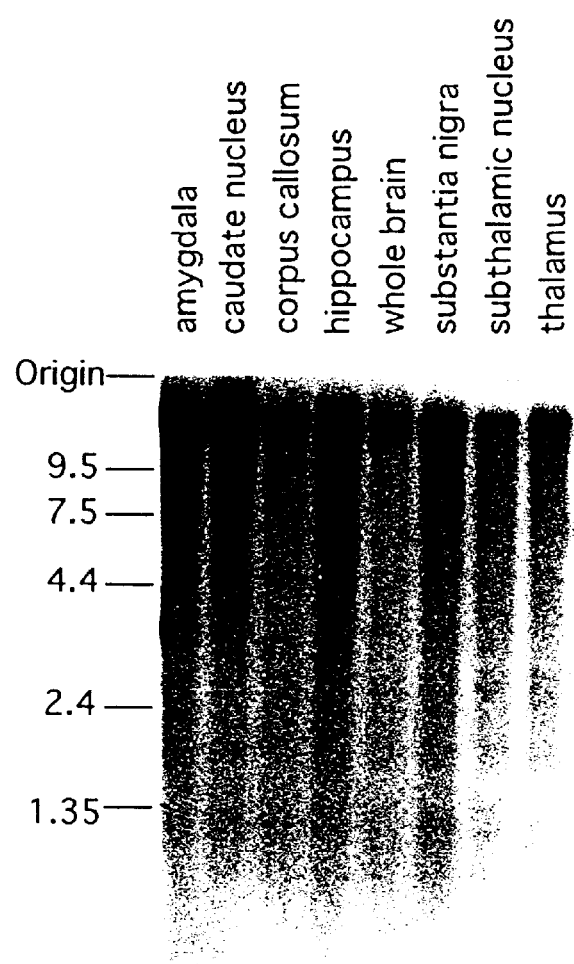

B, intracellular calcium signal as a reaction to caffeine in dyspedic myotubes which express chimeric human RyR3. (a) Non-injected dyspedic myotubes do not react to 1 mM caffeine (n=20). (b) Dyspedic myotubes into which chimeric human RyR3-cDNA has been injected react to 1 mM caffeine (n =5 out of 20). The path of the base line is possibly caused by the fading of the dye, FIG. 3 shows the distribution of human RyR3 in the human brain by Northern blot analysis of various regions of the brain with cDNA probes for human RyR3-mRNAs. 2 mg of poly(A)$^+$ RNA were used in each case. Autoradiography was carried out at −70° C. over 7 days using an intensifying screen.

Figure 4:
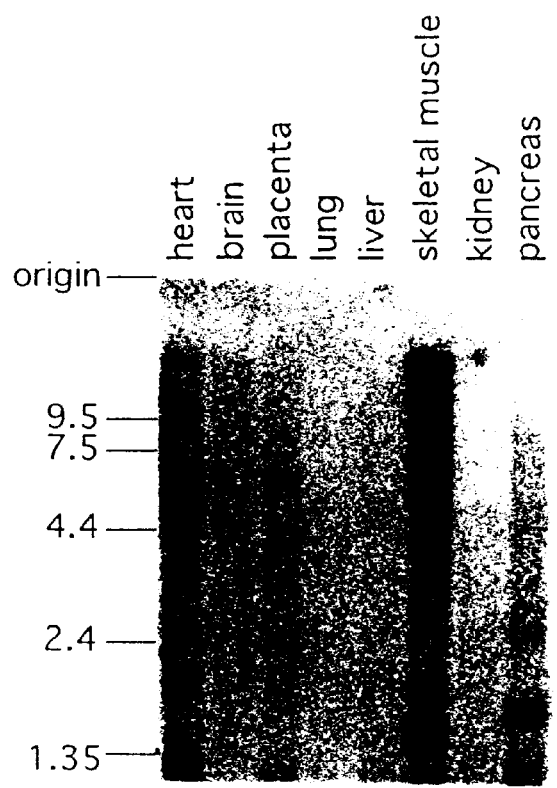

FIG. 4 shows the expression of human RyR3 by Northern blot analysis of different human tissues with cDNA probes for human RyR3-mRNAs. 2 mg of poly(A)$^+$ RNA were used in each case. The autoradiography was carried out at −70° C. over 7 days with an intensifying screen.

Figure 5:
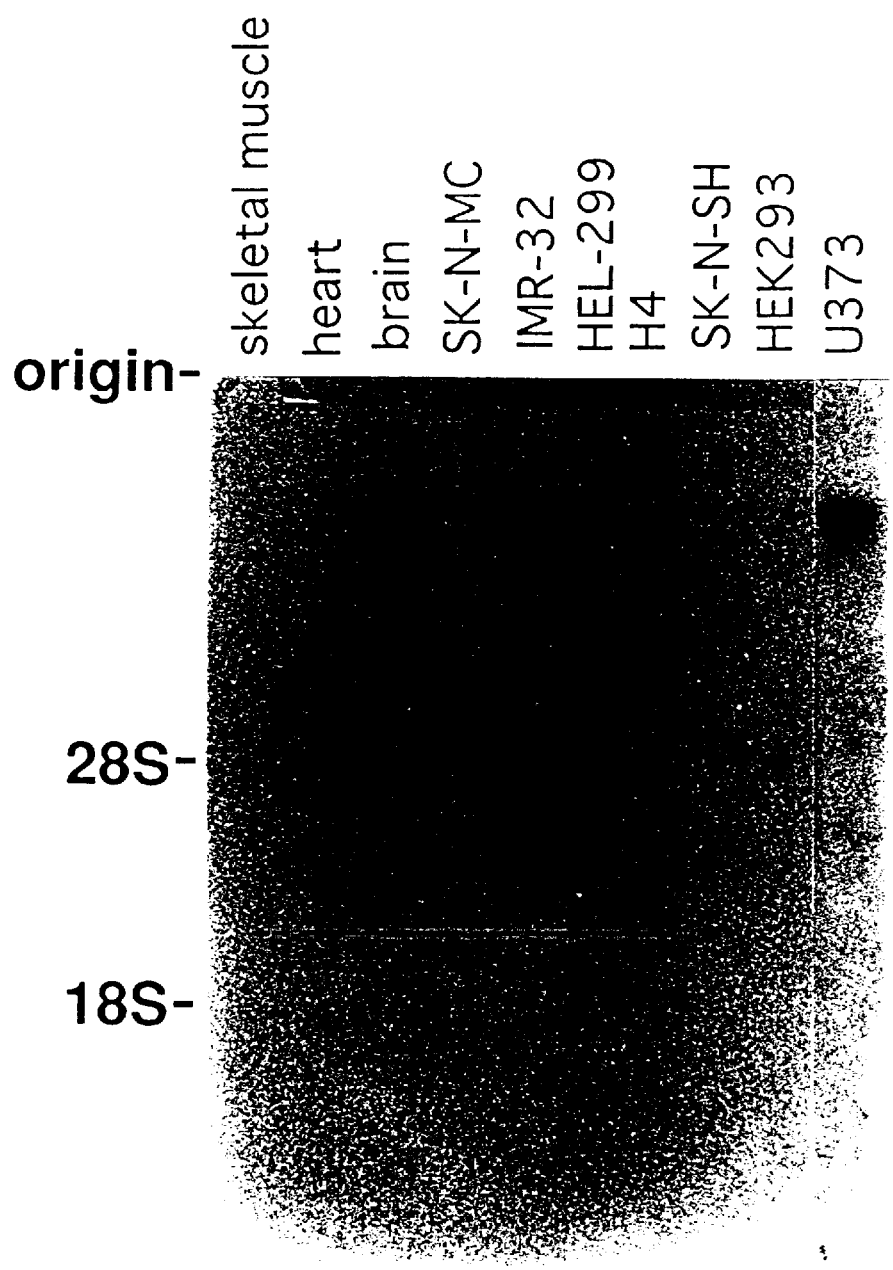

FIG. 5 shows the distribution of human RyR3 in human cell lines by Northern blot analysis of human RyR-mRNA expression in rabbit skeleton muscle, rabbit heart, rabbit whole brain and human cell lines such as neuroblastoma (SK-N-MC, IMR-32), lung fibroblasts (HEL-299), neuroglyoma (H4), neuroblastoma (SK-N-SH), embryonic kidney cells (HEK293) and astrocytorna (U373) with cDNA probes for human RyR3-mRNAs. 20 mg of total RNA were used in each case. The autoradiography was carried out at −70° C. over 4 days with an intensifying screen.

Figure 6:
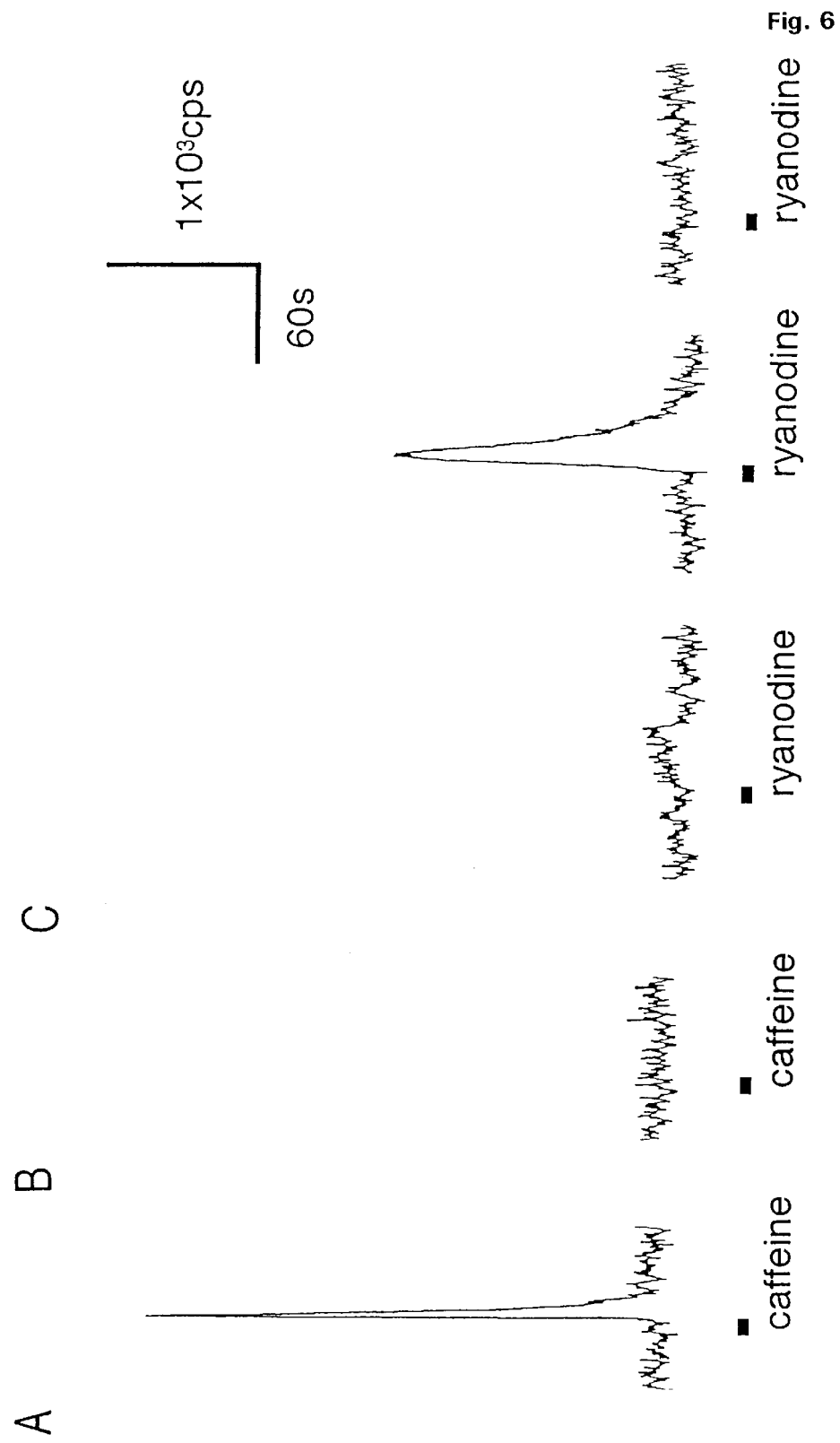

FIG. 6 shows the increase in intracellular calcium in U373 cells after the addition of caffeine and ryanodine. A: CHO cells transfected with rabbit RyR2-cDNA (Maeda, A. et al., Anal. Biochem. 242, (1996), 58–66) show a clear increase in intracellular calcium as a reaction to caffeine (n=11 out of 11). B: Caffeine produces no effect in U373 cells (n=7). C: Ryanodine triggers temporary calcium fluctuations (n=2 out of 4). Some cells do not react to the addition of ryanodine (n=2 out of 4). The uneven reaction probably cannot be put down to the ryanodine receptor not reaching the activity site as recently described (Penner, R. et al., FEBS Lett. 259, (1989), 217–221). The time of addition of caffeine and ryanodine receptor is marked by small bars.

FIG. 7 shows the amino acid sequence (SEQ ID NO:2) of human ryanodine receptor derived from the DNA sequence (SEQ ID NO:1).

FIG. 8 shows the DNA sequence (SEQ ID NO:1) of the human ryanodine receptor.

The problem of the present invention was to provide the nucleic acid sequence of the type 3 human ryanodine receptor, its amino acid sequence and to determine structural and physiological peculiarities which distinguish hRyR3 from all the other RyR.

This problem is solved by the present invention within the scope of the specification and claims by providing polypeptides which are characterised in that they have an amino acid sequence which is at least 90% identical with that of the rabbit ryanodine receptor of type 3 (rRyR3). In one particular embodiment the present invention relates to polypeptides which are characterised in that their amino acid sequence is approximately 96% identical with that of rRyR3.

In a special embodiment the present invention relates to the type 3 human ryanodine receptor (hRyR3) having the amino acid sequence shown in FIG. 7 (SEQ ID NO: 2).

The polypeptides and functional derivatives of hRyR3 prepared make it possible for the first time to compare human RyR3 with RyR types of other species and point out any differences. The polypeptides prepared according to the invention include the human RyR3 and its "functional derivatives".

The term "functional derivative" which is at the basis of the present invention denotes, according to the invention, a component with the biological activity which is substantially similar to the biological activity of native hRyR3. The biological capability relates both to the binding ability of inhibitors and activators such as caffeine and also other physiological ligands of the native receptor and the release of intracellular calcium. However, a "functional derivative" also includes parts of hRyR the biological properties of which have been modified by fragments of other proteins such as other RyR, for example. In one particular embodiment reference is made to the example of a chimeric receptor made up of hRyR3 and rRyR2. The term "functional derivatives" is intended to include "fragments", "variants" and "chemical derivatives". The term "fragment" relates to any polypeptide which is smaller in shape compared with the native receptor and has at least one binding site for a ligand of hRyR. A "variant" comprises molecules which are essentially derived from native hRyR3 in function and structure, such as allelic forms, for example. Consequently, the term "variant" includes the molecules which have a similar activity but a different amino acid sequence, for example. A chemical derivative includes additional chemical groups which are not normally part of the molecule. These groups may strengthen or weaken the biological activity of the molecule, for example.

One aspect of the present invention relates to chimeric polypeptides which are characterised in that they contain, in addition to at least one fragment of the type 3 human ryanodine receptor (hRyR3), at least one other fragment of another polypeptide.

In a particular embodiment the present invention relates to chimeric polypeptides which are characterised in that they contain, in addition to a fragment of hRyR3, at least one other fragment from the family of the non-human ryanodine receptors.

In a special embodiment the present invention relates to chimeric polypeptides which are characterised in that they contain, in addition to a fragment of hRyR3, at least one fragment of the rabbit type 2 ryanodine receptor (rRyR2). In another particular embodiment the present invention relates to a chimeric polypeptide which is characterised in that, in the region of amino acid 1300 of the hRyR3, it contains a fragment of rRyR2 which imparts a high sensitivity to calcium and caffeine.

Based on the calcium releasing activity of RyR3, which is lower than that of other RyR types, measurement of calcium release by known activators such as caffeine is inaccurate or even impossible. This is of great importance for identifying possible inhibitors or activators of the biological activity of RyR3. It has now been found, surprisingly, that a chimeric polypeptide which has a higher sensitivity to calcium or caffeine can be prepared from a fragment of RyR of type 3 and another protein. In one particular embodiment a chimeric polypeptide is prepared from a section of hRyR3 and a non-human section, such as a fragment of rabbit rRyR2, for example. Surprisingly, it has been found that replacing the hRyR3 in the region of amino acid 1300 by a part of the rRyR2 imparts greater sensitivity to caffeine or calcium. This increased calcium or caffeine sensitivity then enables the skilled person to evaluate activators and inhibitors by their effect on the intracellular calcium content in highly sensitive test systems, e.g. in vivo cell systems.

In another aspect the present invention relates to nucleic acids which code for the polypeptides according to the invention with the biological activity of the native hRyR3. Nucleic acids include both DNA and RNA. All nucleic acids according to the invention are characterised in that they hybridise with a nucleic acid corresponding to the polypeptide sequences according to the invention under stringent conditions. Under stringent conditions, DNA sequences hybridise with more than 85% homology and preferably with a homology of more than 90%. The skilled man in the field of molecular biology takes stringent conditions to refer to hybridisation conditions as described for example in "Molecular Cloning, A Laboratory Manual, $2^{nd}$ Ed., Sambrook, Fritsch, Maniatis; Cold Spring Harbor Press, 1989" and "Haymes,. B. D. et al., Nucleic Acid Hybridisation, a Practical Approach, IRL Press, Washington, D.C. (1985)".

In another preferred embodiment these DNA molecules code for chimeric polypeptides which contain, in addition to a part of hRyR3, at least one other DNA fragment which may be obtained for example from the family of the ryanodine receptors. In one particular embodiment a nucleic acid for a chimeric polypeptide is prepared from a fragment of hRyR3, the region of which around amino acid 1300 has been replaced by a fragment of rabbit RyR2.

In another particular embodiment the invention comprises all the nucleic acid sequences needed for recombinant preparation of the polypeptides according to the invention. The sequences thus include all additional sequences which are needed for recombinant preparation of the polypeptides, such as vector and host nucleic acids.

In an additional aspect the present invention provides a process for preparing the polypeptides according to the invention which is characterised in that a nucleic acid according to the invention is introduced into a cell or a cell-free in vitro translation system. The process is further characterised in that the nucleic acid may be part of an expression vector. Suitable expression vectors, cells, cell-free in vitro translation systems and the necessary methods of preparing the polypeptides are known to the skilled person in the field of molecular biology.

According to yet another aspect the present invention relates to the use of the polypeptides and/or nucleic acids according to the invention as pharmaceuticals or as ingredients of a pharmaceutical substance, or the use of the polypeptides and/or nucleic acids for preparing a pharmaceutical substance for treating diseases associated with hRyR3. However, the invention also relates to nucleic acids as a pharmaceutical substance or as an ingredient of a pharmaceutical substance which is complementary to the nucleic acid of one of the proteins according to the invention. Such complementary nucleic acids are known to the skilled person under the name "antisense" nucleic acids and their therapeutic importance is well known to those skilled in the art.

An additional aspect of the present invention concerns processes for detecting the polypeptides according to the invention and their nucleic acids. The polypeptides according to the invention make it possible for the first time to provide highly specific immunological methods of detecting these polypeptides in low concentrations. In one particular embodiment the invention relates to processes for detecting the polypeptides according to the invention which are characterised in that the polypeptide is detected immunologically. Immunological methods such as the preparation, purification and use of monoclonal and polyclonal antibodies for quantitative and qualitative highly specific detection of peptides are known to the skilled person from the prior art. In addition, the invention relates in another particular embodiment to the molecular-biological detection of the nucleic acid coding for the polypeptides. Molecular-biological detection is best known to the skilled person in the field of molecular biology and includes inter alia hybridisation and PCR (Polymerase Chain Reaction) methods. In one particular embodiment the method of detecting a nucleic acid according to the invention is characterised in that a nucleic acid complementary to this nucleic acid or to part of this nucleic acid is used for hybridisation.

According to another aspect the present invention relates to the use of the prepared polypeptides and/or nucleic acids for determining possible inhibitors and activators of hRyR3. Consequently, the present invention also includes methods of identifying activators and/or inhibitors of hRyR3 in vitro and/or in vivo, which are characterised in that a nucleic acid according to the invention is introduced into a cell or a cell-free system and expressed, the expression product is exposed to a potential inhibitor or activator and the ion flux mediated by the expression product is measured. The term in vitro relates to cell-free systems while the term in vivo relates to cell systems. In one particular embodiment, activators and/or inhibitors are introduced into cell-free systems enclosed by a membrane, which express the polypeptides according to the invention and, after the addition of potential activators and inhibitors, the change in the ion concentration in the membrane-surrounded chamber is determined. In one particular embodiment the present invention for the first time provides a system in vivo which makes it possible to detect activators and inhibitors of hRyR3 in isolated cells by the expression of the polypeptides according to the invention in RyR-deficient cells. Methods of expressing polypeptides in cells and cell-free systems using the corresponding nucleic acid are known to the skilled person from the prior art. Apart from the expression of the polypeptides according to the invention in cells or cell-free systems, in one quite particular embodiment the invention also relates to the injection of the polypeptides into these cells and systems for identifying inhibitors and/or activators using the methods described above. Potential inhibitors and activators are identified by detecting the changed influence of the expression product on the cell.

The altered influence of the peptide or expression product can be measured by means of the ion flux determined or by the change in the ion concentration in the membrane-surrounded chamber. Generally, the concentration of intracellular calcium ions is measured. One test design used for a process of this kind for determining activators or inhibitors consists, for example, of a cell system or cell-free system expressing hRyR3 which has no or only slight endogenous ryanodine receptor activity, and wherein a measurable change in the ion concentration is detected within the cell system or membrane-enclosed chamber after the addition of potential inhibitors or activators. Systems for detecting activators and inhibitors are already known for RyR1 and RyR2.

In another additional aspect the present invention relates to the detection of the polypeptides according to the invention and/or the hRyR3 for diagnosing pathologically altered tissues. In another aspect of the present invention the polypeptides and/or nucleic acids according to the invention may be used for preparing a diagnostic agent which makes it possible to carry out a process for diagnosing pathological conditions, e.g. the overexpression or deficiency in hRyR3 in tissues, which is characterised in that the presence, overexpression or deficiency in one of the polypeptides according to the invention is detected. According to one particular embodiment the invention relates to processes for diagnosing pathological conditions by immunological detection of the polypeptides according to the invention by antibody binding. By a pathological condition of a tissue is meant any deviation from normal physiological conditions, as found in the majority of clearly healthy tissue. Overexpression of or deficiency in the polypeptides according to the invention in tissues and cells may be detected both by immunological methods and by molecular biological detection of the nucleic acid coding for the polypeptides. In one particular embodiment the present invention therefore relates to processes for diagnosing pathological conditions which are characterised in that the nucleic acid coding for the polypeptide according to the invention is detected. Corresponding molecular biological detection is well known to those skilled in the art in the field of molecular biology and includes inter alia hybridisation processes and PCR (Polymerase Chain Reaction) techniques. In addition, the invention, by providing the nucleic acid sequence of hRyR3, enables the skilled person for the first time to prepare highly specific hRyR3 hybridisation probes with which the presence or absence of nucleic acids of hRyR3 in the tissues can be detected. Highly specific probes for detecting hRyR3 by PCR (Polymerase Chain Reaction) can now also be developed. As a result, pathological conditions in the tissues can be detected by molecular biological methods.

In a preferred embodiment the sequence and molecular physiological characterisation of the cDNA sequence of the native peptide of hRyR3 according to the invention is disclosed hereinafter. The cDNA sequence was identified and characterised by molecular biological methods of hybridisation known to the skilled person and subsequent sequencing of a number of overlapping cDNA clones (see Example 1). The primary structure of the native polypeptide according to the invention was determined by comparing the corresponding reading frame of the amino acid sequence of rabbit RyR3 (Hakamata, Y. et al. FEBS Lett. 312 (1992), 229–235). The amino acid sequence of the native polypeptide is 4866 amino acids long and corresponds to a molecular weight of 551046 Da. FIG. 1 (SEQ ID NO:2) shows the amino acid sequence of hRyR3 derived from cDNA. The nucleotide sequence GAGCCATGG (SEQ ID NO: 6) in the region around the translational initiation codon corresponds well to the consensus initiation sequence CCA(G)CCATGG (SEQ ID NO: 7) (Kozack M. Nucleic. Acids. Res. 12 (1984), 857–872). The 3'-non-coding region is 873 nucleotides long (without the poly (da)-region); the polyadenylation signal AATAAA (Goeddel, D. V. et al. Nature 290 (1981), 20–26) is located 21 nucleotides upstream of the poly (da)-region. A comparison of the amino acid sequences shows more than 90% (about 96%) identity between hRyR3/rRyR3 and more than 60% identity between hRyR3/rRyR2 (about 69%) and hRyR3/RyR1 (about 67%). The hydropathicity profile of hRyR3 is comparable with those of rabbit rRyR3, rRyR2, rRyR1 and human RyR1 in so far as there is no hydrophobic amino terminal sequence present indicating a signal sequence and provided that the remaining regions are primarily hydrophilic and that there are four strongly hydrophobic segments (designated M1, M2, M3 and M4) in the carboxy-terminal end. The carboxy-terminal region in the vicinity of the M3- and M4-segments is particularly well conserved in all RyR. There are also clear differences. Thus, for example, a region of about 100 amino acids is missing both from hRyR3 and from rRyR3 in the vicinity of amino acid 1300; in this region RyR2 has an EF-hand consensus sequence (Moncrief, N. D. J. Mol. Evol. 30 (1990), 522–562) (in the region of amino acids 1336–1347) and a nucleotide binding consensus sequence GXGXXG (Wierenga, R. K. Nature 302 (1983), 842–844) (amino acid groups 1324–1329) (Nakai, J. et al. FEBS Lett. 271 (1990), 169–177). Furthermore, the region directly before the M1 segment in which there is a divergence between hRyR3 and rRyR3 is also different. hRyR3 has four repeating sequences in two tandem pairs (amino acid groups 841–954, 955–1070, 2600–2711 and 2712–2791). Potential ligand binding sites can be determined by means of proposed consensus amino acid sequences. A sequence resembling the motif of the EF hand (Moncrief, N. D. J. Mol. Evol. 30 (1990), 522–562) is detectable in amino acid groups 3928–3939, a region which is relatively well conserved in rRyR3, RyR2 and RyR1. In addition, a potential calmodulin binding site (amino acids 3465–3476), consisting of an amphipathic helix with two groups of positive charges separated by a hydrophobic region (Blumenthal, D. K. Proc. Natl. Acad. Sci. U.S.A. 82 (1985), 3187–3191), is particularly well conserved in rRyR3, rRyR2 and rRyR1. The molecule has four copies of the nucleotide binding consensus sequence GXGXXG (Wierenga, R. K. Nature 302 (1983), 842–844) (amino acid groups 697–702, 699–704, 1135–1140, 2235–2240 and 2524–2529), of which amino acids 2235–2240 are well conserved in rRyR3, rRyR2 and rRyR3. Using the consensus sequence RXXS/T produces 21 potential phosphorylation sites for $Ca^{2+}$/calmodulin-dependent protein kinases, four of which (serine group 2707 and the threonine groups 130, 290 and 4150) are conserved in rRyR3, rRyR2 and rRyR3. There are two potential cAMP-dependent phosphorylation sites (threonine groups 1244 and 4158), defined as KRXXS/T or RRXS/T (Kemp, B. E. and Pearson R. B. Trends. Biochem. Sci. 15 (1990), 342–346), which are not, however, conserved in rRyR. All these potential binding sites are arranged on the presumably cytoplasmic side, corresponding to the transmembrane topology model (Takeshima, H. et al. Nature 339 (1989), 439–445). Arginine group 613 or 614, the replacement of which by cysteine in RyR1 is associated with malignant hyperthermia (MH) in pigs and humans, is conserved in all three types of RyR. It is now possible to make quantitative and qualitative statements as to its molecular properties by comparing the primary structure of hRyR3 with other ryanodine receptors. A knowledge of the primary structure of the native protein also offers the skilled person in the field of protein chemistry the possibility of designing structural and binding models which will be helpful in explaining the physiological function and in detecting possible inhibitors and activators of this receptor.

Up till now, functional examination of RyR3 has not provided any direct evidence of its operation as a calcium releasing channel. In one particular embodiment of the present invention, the functional recombinant expression of hRyR3 by myotubes from mice without the skeletal muscle isoform of RyR (Nakai, J. et al. Nature 380 (1996), 72–75) has now been shown for the first time. The expression of Wild-type hRyR3 in myotubes from RyR1-deficient (dyspedic) mice by injecting cDNA into the nuclei is possible but is difficult to detect with caffeine owing to an endogenous caffeine reaction of the dyspedic myotubes, as the difference between the caffeine reaction of uninjected myotubes and of myotubes injected with RyR3 cDNA is very indistinct (10 mM caffeine). This result was not unexpected as hRyR3 in human T-lymphocytes shows no caffeine reaction either (Hakamata, Y. et al. Febbs Lett. 352 (1994), 206–210). It is assumed that caffeine acts on the RyR by increasing the calcium sensitivity. Consequently, the problem of imparting a greater calcium sensitivity to the RyR3 has been solved in an inventive manner. Based on the assumption that the missing region around amino acid group 1300 contains the region which determines calcium sensitivity, it is possible to produce a chimeric RyR molecule in which the missing region is replaced by a sequence of RyR2 which has a high calcium sensitivity. One third of a chimeric molecule of RyR of this kind may consist of the rRyR2 amino acid sequence in the N-terminus while two thirds may consist of the hRyR3 sequence in the C-terminus (FIG. 2A). FIG. 2B shows a caffeine reaction of the chimeric RyR expressed in dyspedic myotubes. The chimeric RyR reacts with 1 mM of caffeine (FIG. 2B, n=5 out of 20). On the other hand, non-injected dyspedic myotubes showed no reaction whatsoever to 1 mM of caffeine (FIG. 2B, n=0 out of 20). This shows for the first time that chimeric RyR may form intracellular calcium channels which react to caffeine.

Based on the prediction of the structure of the RyR amino acid sequence, the channel-forming region of the RyR is located in the C-terminal tenth of the RyR molecules (Takeshima, H. et al. Nature 339 (1989), 439–445; Nakai, J. et al. FEBS Lett. 271 (1990), 169–177; Hakamata, Y. et al. FEBS Lett. 312 (1992), 229–235; Zorzato, F. et al. J. Biol. Chem. 265 (1990), 2244–2256). It is to be assumed that the C-terminal two thirds of hRyR3 contain the calcium release channel activity and that the N-terminal third of the RyR sequence contains a region which determines the caffeine and/or calcium sensitivity.

One particular embodiment of the present invention relates to the detection of hRyR3 in tissues. This can be done using hRyR3-specific probes and Northern blot analysis of mRNA from various human tissues. It can be shown that even though a weak signal for RNA can be observed in the brain as a whole, a section of RNA about 16 kb in size hybridises with hRyR-cDNA probes in relatively large amounts in restricted areas of the brain such as the Nucleus caudatus, amygdala and hippocampus and in rather smaller amounts in the Corpus callosum, Substantia nigra and thalamus (FIG. 3). The limited distribution of RyR3 in the human brain leads to the following assumptions. It is known that the RyR is also coupled directly to L-type calcium channels in the brain. Whereas P-type and other types of calcium channels are expressed throughout the brain, the R-type calcium channel is expressed only in the very restricted regions of the brain such as the Nucleus caudatus and hippocampus (Niidome, T. et al. FEBS Lett. 308 (1992), 7–13). With the distribution of the R-type calcium channel and RyR3 being similar, it is probable that the RyR3 can interact directly with the R-type calcium channel in these regions. Since the regions of RyR3 expression also correspond roughly to the areas where the "delayed neuronal death" takes place after hypopoxia in the brain, it is probable that this type of RyR plays an important role in pathological conditions. The increased locomotor activity of RyR3-deficient mice reflects this distribution of RyR3.

In another embodiment it can be shown that even outside the brain, in the skeletal muscle, an RNA species can be detected which hybridises with hRyR3-cDNA probes (FIG. 4). The size of the RNA species of these tissues, i.e. about 16 kb, corresponds to the species in the brain. A weak signal indicates the existence of RyR3-mRNA in the heart tissue. The distribution of mRNA outside the brain differs from the rabbit, as RyR3 expression cannot be detected in rabbit skeleton muscle. Owing to the high content of RyR1-mRNA in the skeletal muscle, a small contribution by cross-hybridisation of RyR3 probes with RyR1-mRNA cannot be ruled out. In any case, mRNA from the heart led to a substantially smaller hybridisation signal, in spite of the higher homology of RyR3 with RyR2 compared with RyR1. This, together with the isolation of RyR3-cDNA from a cDNA library from the skeletal muscle indicates that RyR3 really is expressed in the heart muscle. Moreover, RyR3 can be detected in the skeletal muscle of other species such as mice, birds and frogs.

In another embodiment for detecting hRyR3 it is shown that RyR3 expression varies between the species and that the expression of RyR3 is more marked in human skeletal muscle than in other species. It is known that an acute increase in intracellular calcium in human skeletal muscle triggers malignant hyperthermia (MH) (MacLennan, D. H. and Philips, M. S. Science 256 (1992), 789–794). Although MH is associated with mutations of RyR1 (Gillard, E. F. et al. Genomics 11 (1991), 751–755), only 5% of the MH cases show a mutation in position 614 of the RyR1 gene by Arg to Cys substitution. The abundant expression of RyR3 in human skeletal muscle makes it very probable that RyR3 participates in variant forms of MH. Moreover there is the possibility that RyR3 might be implicated in other disorders of intracellular calcium regulation.

In another most particular embodiment it was therefore established that hRyR3 is present in pathological conditions in humans and can be detected in pathologically altered tissue. For this purpose, it was shown using cell lines derived from human brain tumours that the tissue-specific distribution of RyR3 in the human brain is connected with the cell-specific calcium regulation during proliferation. RyR3-mRNA is expressed in a number of human cell lines (FIG. 5). Abundant expression can be found in U373, a cell from malignant astrocytoma, weak expression in IMR-32 from malignant neuroblastoma cells and even weaker expression in H4 from malignant neuroglyoma cells. In spite of the expression of RyR2 in IMR-32, no other types of RyR can be detected in U373 or H4. The expression of RyR3 could not be detected in the neuronal cells SK-N-MC or SK-N-SH in spite of their malignance. U373 and H4 reacted to ryanodine but not to caffeine with an increase of extracellular calcium, whereas a caffeine reaction can be detected under the same conditions in RyR2-expressing CHO rabbit cells (FIG. 6). The ryanodine and caffeine reactions of U373 and H4 can also be observed in T-lymphocytes, a typical feature of RyR3 (Hakamata, Y. FEBS Lett. 352 (1994), 206–210).

EXAMPLES

1. Cloning of cDNA

5 Oligo (dT)- and random primer cDNA libraries from human brain (Nucleus caudatus) produced by Messrs. Clontech (USA) were used, which were isolated from poly(A)$^+$ RNA and cloned into λgt10 phages. Searching the cDNA libraries (~3.0×10$^5$ plaques) with the fragment PstI(9790)/EcoRI(11834) from rabbit RyR3 cDNA clone pBRR74 (9) led to λhBRR79. The cutting sites of the restriction endonucleases are indicated by figures (in brackets) which describe the 5'-terminal nucleotide originating from the cleaving: the nucleotide groups are numbered in the 5'-3'-direction starting with the first group of the ATG triplet which codes the methionine which is thought to be the initiator. Subcloning of the cDNA insert of λhBRR79 into the EcoRI cutting site of pBluescript SK(−) (Stratagene) led to phBRR79. The library was searched nine times with different probes:

| Fragment used: | Result: (positive clones) |
|---|---|
| 2.4 kb (kilobases) EcoRI (vector)/DraI(2395) from pBRR331 | λhBRR22, λhBRR61, λhBRR112 |
| 1.2 kb PmaCI(4750)/ApaI(5912) from PBRR133 (9) | λhBRR51, λhBRR52, λhBRR53 |
| 1.3 kb EcoRI(vector)/HindII (14656) from pBRR110 (9) | λhBRR91, λhBRR93 |
| 1.3 kb KpnI(6249)/HindIII (7523)from pBRR121 (9)and 1.1 kb XbaI(8405)/PstI(9494) from pBRR92 (9) | λhBRR140, λhBRR141, λhBRR411 |
| 1.0 kb EcoRI(vector)/EcoRI (13335) from λhBRR93 and 0.8 kb SpeI(10569)/EcoRI(11408) from λhBRR79 | λhBRR161 |
| 0.8 kb EcoRI(vector)/EcoRI (11815) from λhBRR161 | λhBRR407 |

Moreover, two additional clones were obtained by RT-PCR. 1 mg of poly(A)$^+$ RNA (Clontech) from human brain was incubated together with RNase H-Reverse Transcriptase from Moloney's murine leukaemia virus (Gibco BRL) with random primer. The first cDNA strand synthesised was amplified using a DNA thermal cycler (Perkin Elmer Corp.) in accordance with the manufacturer's instructions (TaKaRa LA PCR kit). After a hot start (1 min., at 94° C.) the probes were exposed to 30 cycles of 20 seconds at 98° C. and 5 minutes at 68° C. Pairs of primers for phBRR501 were synthetic 25 nucleotide oligomers of bases 2949–2973 (upper primer, AGTGGATAAACTTGCAGAAAATGCA) (SEQ ID NO:8) and 3495–3519 (lower primer, TGGGGAGCTGCTGATCACCAATAAA) (SEQ ID NO:9) of the phBRR61 and phBRR51 clones. Pairs of primers for phBRR502 were synthetic 20-nucleotide oligomers of bases 11369–11388 (upper primer TTGATGAATCTGGACAGCAC) (SEQ ID NO:10) and 12353–12372 (lower primer, ACGTGTTAGAAATTGCGGGT) (SEQ ID NO:11) of the phBRR79 and phBRR91 clones. The cDNA clones for nucleotide sequence analysis were: phBRR22 (with nucleotides 86 to 1263), phBRR61 (991–3103), phBRR501 (2949–3519), phBRR51 (3435–5253), phBRR53 (4444–7346), phBRR411 (7330–9900), phBRR79 (8358–11408), phBRR502 (11369–12372) and phBRR91 (11468–15486). All the cDNA inserts apart from phBRR501 and phBRR502 were subcloned into the EcoRI cutting site of pBluescript SK(−). The 0.6 kb HindIII(2956)/-BclI(3506) fragment of phBRR501 was subcloned into the BamHI/

HindIII cutting site and the 0.5 kb ApaI(11451)/AccI(11930) fragment of phBRR502 was subcloned into the AccI/ApaI cutting site of pBluescript SK(−). Both strands of the resulting cDNA and the PCR products of reverse transcriptase were sequenced by the dideoxy chain termination method (Sanger, F. et al., Proc.Natl.Acad.Sci. U.S.A., 74, (1977), 5463–5467).

2. Physiological Characterisation

The entire protein-coding sequence of human RyR3 was cloned into the EcoRI/NotI cutting site of pCI-neo (Promega) and resulted in hNRR9. The cDNA insert was constructed from the following fragments: EcoRI(vector)/MroI(1232) obtained from IhBRR22, MroI(1232)/HindIII (2956) from IhBRR61, HindIII(2956)/BclII(3506) from IhBRR501, BclII(3506)/PmaCI(4750) from IhBRR51, PmaCI(4750)/PstI(7339) from IhBRR53, PstI(7339)/ClaI (9559) from IhBRR411, ClaI(9559)/SpeI(10569) from IhBRR79, SpeI(10569)/ApaI(11451) from IhBRR407, ApaI (11451)/EcoRI(11815) from IhBRR502, EcoRI(11815)/EcoRI(14861) from IhBRR91. The expression plasmid of the chimeric ryanodine receptor cDNA from human RyR3 and rabbit RyR2 was constructed as follows: the SalI (vector)/PmaCI(5038) fragment was rabbit RyR2 cDNA (Nakai, J. et al. FEBS Lett. 271 (1990), 169–177) and the PmaCI(4750)/NotI(vector) fragment from human RyR3-cDNA was ligated into the SalI/NotI cutting site of pCI-neo. Cultures of myotubes from RyR1-deficient (dyspedic) mice and cDNA injection are already known (Nakai, J. et al., Nature 380, (1996), 72–75). Changes in fluorescence (dimensionless random units) were measured after loading the myotubes with fluo-3 AM (Garcia, J., and Beam, K. G., J. Gen. Physiol. 103, (1994), 107–123). Caffeine was applied by local injection using a wide-tipped pipette (10–50 mm in diameter). The washing solution used was normal Nager-Ringer solution of the following composition (mM): 145 NaCl, 5 KCl, 2 $CaCl_2$, 1 $MgCl_2$, 10 HEPES, pH 7.4 adjusted using NaOH. The temperature was 20–22° C.

3. Northern Blot Analysis

For the Northern blot analysis of human brain and other tissues, commercial Multiple Tissue Northern (MTN) blots (Clontech) were used. Each track in the MTN blots contains approximately 2 μg of poly(A)$^+$ RNA from the following regions of the brain: amygdala, Nucleus caudatus, Corpus callosum, hippocampus, whole brain, Substantia nigra, subthalamic nucleus and thalamus. Each track of the other MTN blot contains roughly 2 mg of poly(A)$^+$ RNA from the following human tissues: heart, brain, placenta, lung, liver, skeletal muscle, kidney and pancreas. Each track of the third blot contains roughly 20 mg of total RNA of the following human cell lines (Hakamata Y., et al. FEBS Lett. 312 (1992), 229–235): SK-N-MC (derived from original neuroblastoma) IMR-32 (neuroblastoma), HEL-299 (lung fibroblast), H4 (neuroglyoma), SK-N-SH (neuroblastoma), HEK-293 (embryonic kidney cell) and U373 (astrocytoma). Since the probes obtained from cDNA parts of the human ryanodine receptor produced only weak signals, the 14.9 kb NalI (vector)/NotI(vector) fragment from phNRR9 was used for the Northern blot analysis. The probe was prepared with the klenow fragment of DNA polymerase and [$^{32}$P] dCTP (Feinberg, A. P. & Vogelstein, B. Anal. Biochem. 132 (1983), 6–13) using random oligonucleotide primer. The blot was hybridised at 42° C. and washed three times with 0.3×SSC, 0.1% SDS at 50° C.

4. Determining Luminescence

The luminescence was determined using the method recently published (Maeda, A. et al., Anal. Biochem. 242, (1996), 58–66). To do this the cells (1×105 cells/vessel) were transferred into the solution of the calcium assay having the following composition (mM): 140 NaCl, 5 KCl, 1.5 $MgCl_2$, 2.5 $CaCl_2$, 5 glucose and 10 HEPES, pH 7.4 adjusted using NaOH, including 2.5 mM of coelenterazine, the intermediate substrate of aequorine, and incubated for 6 hours at 37° C. The system for measuring luminescence consisted of the spectrofluorometer CAF-110 (Jasco) (Hakamata Y. et al., FEBS Lett. 352, (1994), 206–210), which is connected to a luminescence unit PL-03 (Jasco).

The mobilisation of intracellular calcium was induced by injecting caffeine in a final concentration of 10 mM and ryanodine receptor of 100 mM. The total amount of aequorine activity was measured, after permeabilisation of the cells with digitonin, in a final concentration of 200 mg/ml. The ethanol concentration was 0.5% or less since under these conditions there is no release of calcium.

---

What is claimed is:

1. An isolated polypeptide comprising an amino acid sequence identical to SEQ ID NO:2.

2. A chimeric polypeptide comprising the C-terminal two-thirds of SEQ ID NO:2 and N-terminal one-third of an amino acid sequence selected from the group consisting of SEQ ID NO:3 and SEQ ID NO:5, wherein said C-terminal two-thirds of SEQ ID NO: 2 comprises a ryanodine calcium release channel and said N-terminal one-third of SEQ ID NO:3 and 5 comprises a region which determines caffeine and/or calcium sensitivity, and wherein said chimeric polypeptide has the activity of releasing intracellular $Ca^{2+}$.

3. The polypeptide of claim 2, comprising said N-terminal one-third of SEQ ID NO:3.

4. The polypeptide of claim 2, comprising said N-terminal one-third of SEQ ID NO:5.

5. The chimeric polypeptide according to claim 2 consisting of amino acids 1585 to 4866 of SEQ ID NO:2 and amino acids 1 to 1679 of SEQ ID NO:5.

6. An isolated nucleic acid coding for the polypeptide according to claim 1.

7. An isolated nucleic acid coding for the polypeptide according to claim 2.

8. A process for preparing a polypeptide comprising introducing the nucleic acid according to claim 6 into a cell or a cell-free in vitro translation system under conditions suitable to express the polypeptide.

9. A process for preparing a polypeptide comprising introducing the nucleic acid according to claim 7 into a cell or a cell-free in vitro translation system under conditions suitable to express the polypeptide.

10. The process according to claim 8, wherein the nucleic acid is part of an expression vector.

11. The process according to claim 9, wherein the nucleic acid is part of an expression vector.

12. A method of identifying activators and/or inhibitors of human type 3 ryanodine receptor comprising:
 (a) introducing the polypeptide of claim 1 into a cell or cell-free system, or a membrane-surrounded cell-free system;
 (b) exposing the polypeptide to a potential activator or inhibitor;
 (c) measuring the $Ca^{2+}$ flux mediated by the polypeptide or the change in $Ca^{2+}$ concentration in the cell, cell-free system or membrane-surrounded cell-free system; and
 (d) identifying said activators and/or inhibitors of human type 3 ryanodine receptor based on the change of said $Ca^{2+}$ flux or said $Ca^{2+}$ concentration as measured in step (c).

13. A method of identifying activators and/or inhibitors of human type 3 ryanodine receptor comprising:
 (a) introducing the nucleic acid of claim 6 into a cell or cell-free system, or a membrane-surrounded cell-free system and expressing said nucleic acid to produce a polypeptide;
 (b) exposing the polypeptide to a potential activator or inhibitor;
 (c) measuring the $Ca^{2+}$ flux mediated by the polypeptide or the change in $Ca^{2+}$ concentration in the cell, cell-free system or membrane-surrounded cell-free system; and
 (d) identifying said activators and/or inhibitors of human type 3 ryanodine receptor based on the change of said $Ca^{2+}$ flux or said $Ca^{2+}$ concentration as measured in step (c).

14. The method according to claim 13, wherein said nucleic acid is part of an expression vector.

15. A method of identifying activators and/or inhibitors of human type 3 ryanodine receptor comprising:
 (a) introducing the nucleic acid of claim 7 into a cell or cell-free system, or a membrane-surrounded cell-free system and expressing said nucleic acid to produce a polypeptide;
 (b) exposing the polypeptide to a potential activator or inhibitor;
 (c) measuring the $Ca^{2+}$ flux mediated by the polypeptide or the change in $Ca^{2+}$ concentration in the cell, cell-free system or membrane-surrounded cell-free system; and
 (d) identifying said activators and/or inhibitors of human type 3 ryanodine receptor based on the change of said $Ca^{2+}$ flux or said $Ca^{2+}$ concentration as measured in step (c).

16. The method according to claim 15, wherein said nucleic acid is part of an expression vector.

17. A method of identifying activators and/or inhibitors of human type 3 ryanodine receptor comprising:
 (a) introducing the polypeptide of claim 2 into a cell or cell-free system, or a membrane-surrounded cell-free system;
 (b) exposing the polypeptide to a potential activator or inhibitor;
 (c) measuring the $Ca^{2+}$ flux mediated by the polypeptide or the change in $Ca^{2+}$ concentration in the cell, cell-free system or membrane-surrounded cell-free system; and
 (d) identifying said activators and/or inhibitors of human type 3 ryanodine receptor based on the change of said $Ca^{2+}$ flux or said $Ca^{2+}$ concentration as measured in step (c).

* * * * *